US010752939B2

(12) United States Patent
Johnson et al.

(10) Patent No.: US 10,752,939 B2
(45) Date of Patent: *Aug. 25, 2020

(54) PROBES FOR IMPROVED MELT DISCRIMINATION AND MULTIPLEXING IN NUCLEIC ACID ASSAYS

(71) Applicant: LUMINEX CORPORATION, Austin, TX (US)

(72) Inventors: Scott C. Johnson, Austin, TX (US); Nicolas Arab, Austin, TX (US); Doug Whitman, Round Rock, TX (US)

(73) Assignee: LUMINEX CORPORATION, Austin, TX (US)

( * ) Notice: Subject to any disclaimer, the term of this patent is extended or adjusted under 35 U.S.C. 154(b) by 255 days.

This patent is subject to a terminal disclaimer.

(21) Appl. No.: 15/656,541

(22) Filed: Jul. 21, 2017

(65) Prior Publication Data

US 2017/0321259 A1 Nov. 9, 2017

Related U.S. Application Data

(63) Continuation of application No. 14/823,288, filed on Aug. 11, 2015, now Pat. No. 9,982,291.

(60) Provisional application No. 62/035,783, filed on Aug. 11, 2014.

(51) Int. Cl.
| *C12Q 1/68* | (2018.01) |
| *C07H 21/00* | (2006.01) |
| *C12Q 1/6818* | (2018.01) |
| *C12Q 1/6816* | (2018.01) |
| *C12Q 1/6823* | (2018.01) |

(52) U.S. Cl.
CPC ......... *C12Q 1/6818* (2013.01); *C12Q 1/6816* (2013.01); *C12Q 1/6823* (2013.01)

(58) Field of Classification Search
CPC .................................. C12Q 1/68; C07H 21/00
See application file for complete search history.

(56) References Cited

U.S. PATENT DOCUMENTS

| 6,251,600 B1 | 6/2001 | Winger et al. | |
| 6,951,722 B2 | 10/2005 | Mukai et al. | |
| 6,977,161 B2 | 12/2005 | Grenier et al. | |
| 7,422,850 B2 | 9/2008 | Marshall et al. | |
| 9,982,291 B2 * | 5/2018 | Johnson | C12Q 1/6818 |
| 2007/0020656 A1 | 1/2007 | Sorge | |
| 2009/0068643 A1 | 3/2009 | Behlke et al. | |
| 2009/0325169 A1 * | 12/2009 | Walder | C12Q 1/6844 435/6.18 |
| 2010/0167353 A1 * | 7/2010 | Walder | C12Q 1/6844 435/91.2 |
| 2011/0223585 A1 | 9/2011 | Gullber et al. | |
| 2011/0269129 A1 | 11/2011 | Gerasimova et al. | |
| 2012/0052492 A1 | 3/2012 | Li | |
| 2012/0258455 A1 * | 10/2012 | Behlke | C12Q 1/6858 435/6.11 |
| 2013/0109588 A1 | 5/2013 | Chun et al. | |
| 2014/0057269 A1 | 2/2014 | Marshal et al. | |
| 2015/0044680 A1 | 2/2015 | Whitman et al. | |
| 2015/0307917 A1 * | 10/2015 | Walder | C12Q 1/686 435/6.12 |

FOREIGN PATENT DOCUMENTS

| EP | 2307574 B1 | 9/2012 |
| EP | 2279263 B1 | 9/2013 |
| EP | 2438189 B1 | 9/2013 |
| EP | 2644707 A1 | 10/2013 |
| JP | 2007-068530 | 3/2007 |
| JP | 2009-050217 | 3/2009 |
| JP | 2010-520756 | 6/2010 |
| WO | WO 1999/001571 | 1/1999 |
| WO | WO 2008/048334 | 4/2008 |
| WO | WO 2008/063194 | 5/2008 |
| WO | WO 2008/109823 | 9/2008 |
| WO | WO 2010/036359 | 4/2010 |
| WO | WO 2011/142836 | 11/2011 |
| WO | WO 2012/024639 | 2/2012 |
| WO | WO 2013/166466 | 11/2013 |

OTHER PUBLICATIONS

Guan et al., A highly parallel microfluidic droplet method enabling single-molecule counting for digital enzyme detection. BioMicrofluidics 8 :014110-1-13 (Year: 2014).*
Hindson et al., High-Throughput Droplet Digital PCR System for Absolute Quantitation of DNA Copy Number. Analytical Chemistry 83 : 8604 (Year: 2011).*
Office Communication issued in corresponding Japanese Application No. 207-507861, dated May 30, 2019.
Bonnett, et al., "Thermodynamic basis of the enhanced specifically of structured DNA probes," *PNAS*, 96:6171, 1999.
International Search Report and Written Opinion, issued in PCT/US2015/044609, dated Dec. 29, 2015.
Invitation to Pay Additional Fees, issued in PCT/US2015/044609, dated Oct. 28, 2015.
Johnson, et al., "A third base pair for the polymerase chain reaction: inserting isoC and isoG," *Nucleic Acids Research*, 32:1937, 2004.
Livak, "Allelic discrimination using fluorogenic probes and the 5' nuclease assay," *Genetic Analysis: Biomolecular Engineering*, 14:143, 1999.

(Continued)

*Primary Examiner* — Ethan C Whisenant
(74) *Attorney, Agent, or Firm* — Parker Highlander PLLC

(57) ABSTRACT

Methods and compositions for the detection and quantification of nucleic acids are provided. In certain embodiments, methods involve the use of cleavable probes that comprise a ribonucleotide position that is susceptible to endoribonuclease (e.g., RNase H) cleavage in the presence of target nucleic acid molecules. Probes of the embodiments may also comprise non-natural nucleotide linked to a reporter and/or quenching moiety.

28 Claims, 25 Drawing Sheets

Specification includes a Sequence Listing.

(56) References Cited

OTHER PUBLICATIONS

Office Communication, issued in U.S. Appl. No. 14/823,288, dated Apr. 7, 2017.
Extended European Search Report issued in corresponding European Application No. EP 15832414, dated Mar. 13, 2018.
Harvey et al., "Characterization and applications of CataCleave probe in real-time detection assays," *Anal. Biochem.*, 333(2):246-255, 2004.
Sherrill et al., "Nucleic acid analysis using an expanded genetic alphabet to quench fluorescence," *J. Am. Chem. Soc.*, 126(14):4550-4556, 2004.
Extended Search Report and Opinion, issued in European Patent Application, Serial No. 19201668.3, dated Mar. 31, 2020.
Jacroux, et al., "Enzymatic amplification of DNA/RNA hybrid molecular beacon signaling in nucleic acid detection," *Anal. Biochem.*, 432:106-14, 2013.
Liu, et al., "A novel single nucleotide polymorphism detection of a double-stranded DNA target by a ribonucleotide-carrying molecular beacon and thermostable RNase HII," *Anal. Biochem.*, 398:83-92, 2010.

* cited by examiner

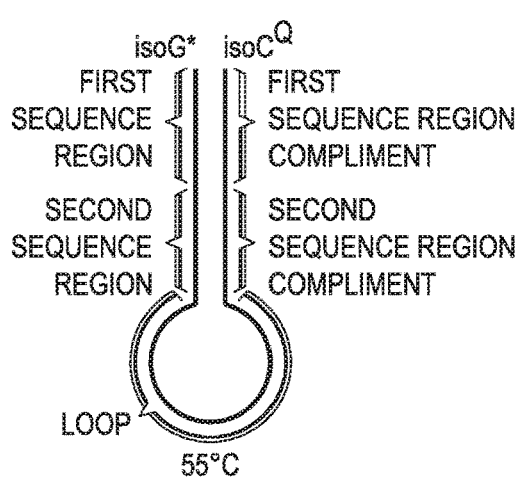 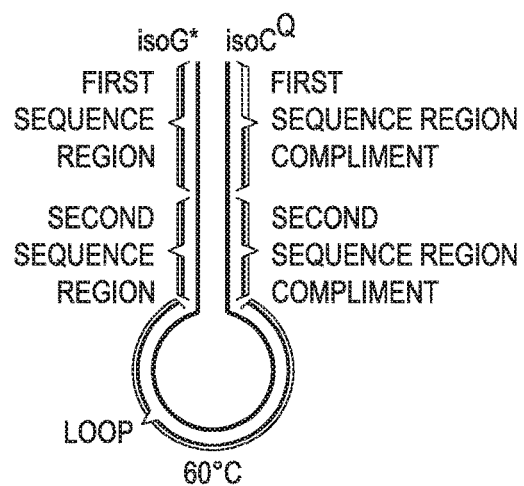
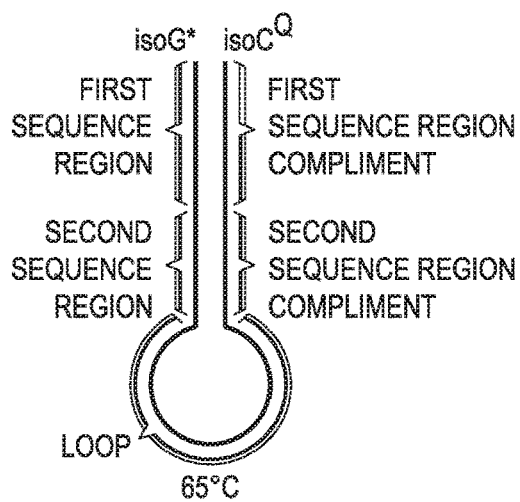 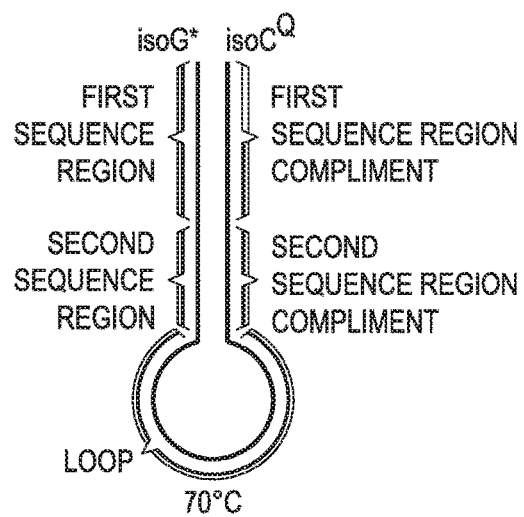
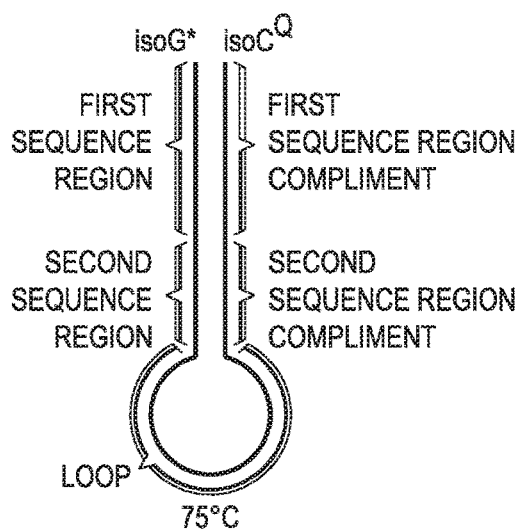 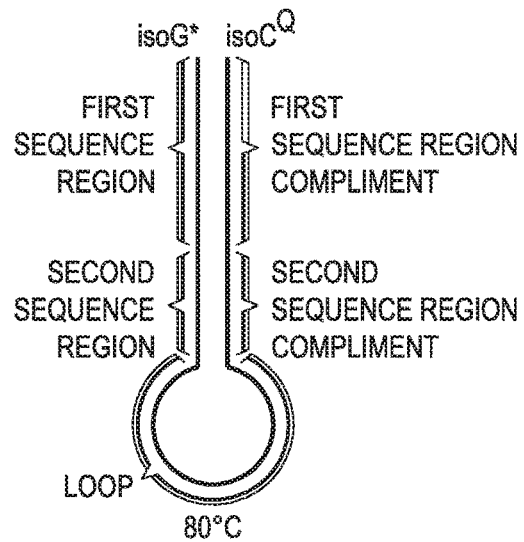
FIG. 1B

| CONSTRUCT | PROBE 5'-3' | STEM (bp) | B-B" (bp) | C-C" (bp) | LOOP (bp) | ΔG (kcal.mole-1) | Tm STEM LOOP (°C) |
|---|---|---|---|---|---|---|---|
| RTx-1 | ATATCAGTC*ATTG*CCCAAAACCG*CAAT*GAC | 8 | 3 | 5 | 7 | -1.27 | 64.8 |
| RTx-2 | ATATCAGTC*ATTG*CCCAAAAAACCG*CAAT*GAC | 8 | 3 | 5 | 12 | -1.06 | 63.6 |
| RTx-3 | ATATCAGTC*TTG*CCCAAACCG*CAA*GAC | 7 | 3 | 4 | 7 | -0.87 | 63.3 |
| RTx-4 | ATATCAGTC*TTG*CCCAAAAAACCG*CAA*GAC | 7 | 3 | 4 | 12 | -0.66 | 62 |
| RTx-5 | ATATCAGTCAA*TTG*CCCAAACCG*CAATT*GAC | 9 | 4 | 5 | 7 | -1.62 | 65.7 |
| RTx-6 | ATATCAGTCAA*TTG*CCCAAAAAACCG*CAATT*GAC | 9 | 4 | 5 | 12 | -1.41 | 64.6 |
| RTx-7 | ATATCAGTCA*GTG*CCCAAACC*CACTT*GAC | 8 | 4 | 4 | 7 | -0.93 | 62.9 |
| RTx-8 | ATATCAGTCA*GTG*CCCAAAAAACC*CACTT*GAC | 8 | 4 | 4 | 12 | -0.72 | 61.8 |
| RTx-9 | ATATCAGGTC*AG*CCCAAACC*CT*GACC | 6 | 5 | 1 | 7 | -0.26 | 59.8 |
| RTx-10 | ATATCAGTC*TG*CCCAAACCG*CAG*AC | 6 | 3 | 3 | 7 | -0.53 | 61.7 |
| RTx-11 | ATATCAGTC*CG*GCCAAACCG*CG*AC | 5 | 3 | 2 | 7 | -0.5 | 62 |

FIG. 2

| PROBE CONSTRUCT | SEQUENCE | STEM (bp) | LOOP (bp) | ΔG (kcal/mole) | Tm STEM LOOP (°C) |
|---|---|---|---|---|---|
| RTx2-20 | /56-FAM/T/iMe-isodC/ATATCAGTC*ATT*GCCCAAAAAAAAAAAC *GCAAT*GACrCATGAGACAGTATAGCGCTGA/3SpC3/ | 3 | 20 | -0.42 | 60.2 |
| RTx-2 | /56-FAM/T/iMe-isodC/ATATCAGTC*ATT*GCCCAAAAAACC *GCAAT*GACrCATGAGACAGTATAGCGCTGA/3SpC3/ | 3 / 5 | 12 | -1.06 | 63.6 |
| RTx-2b | /56-FAM/T/iMe-isodC/ATATCAGTC*ATGT*GCCCAAAAAACC *GCACAT*GACrCATGAGACAGTATAGCGCTGA/3SpC3/ | 3 / 6 | 12 | -2.28 | 68.7 |
| RTx-2c | /56-FAM/T/iMe-isodC/ATATCAGTC*ATT*TGCCCAAAAAACC *GCAAAT*GACrCATGAGACAGTATAGCGCTGA/3SpC3/ | 3 / 6 | 12 | -1.41 | 64.6 |
| RTx-6 | /56-FAM/T/iMe-isodC/ATATCAGTC*ATT*GCCCAAAAAACC *GCAAT*TGACrCATGAGACAGTATAGCGCTGA/3SpC3/ | 4 / 5 | 12 | -1.41 | 64.6 |
| RTx-2-12AT-1 | /56-FAM/T/iMe-isodC/ATATCAGTC*ATT*GACCAAAAAACC T*CAAT*GACrCATGAGACAGTATAGCGCTGA/3SpC3/ | 3 / 5 | 12 | 0.09 | 57.5 |
| RTx-2-12AT-2 | /56-FAM/T/iMe-isodC/ATATCAGTC*ATGT*ACCCAAAAAACC *GTACAT*GACrCATGAGACAGTATAGCGCTGA/3SpC3/ | 3 / 5 | 12 | 0.54 | 55.1 |
| RTx-2-12AT-3 | /56-FAM/T/iMe-isodC/ATATCAGTC*ATGT*ACCCAAAAAACC *GTACAT*GACrCATGAGACAGTATAGCGCTGA/3SpC3/ | 3 / 6 | 12 | -0.68 | 61.3 |
| RTx-2-12AT-4 | /56-FAM/T/iMe-isodC/ATATCAGTC*ATTGT*ACCCAAAAAACC *GTACAAT*GACrCATGAGACAGTATAGCGCTGA/3SpC3/ | 3 / 7 | 12 | -1.03 | 62.4 |
| RTx-8-12AT-3 | /56-FAM/T/iMe-isodC/ATATCAGTCA*ATGT*GCCCAAAAAAAAA AAAAACCG*CACAT*TGACrCATGAGACAGTATAGCGCTGA/3SpC3/ | 4 / 6 | 20 | -1.99 | 66.4 |

FIG. 3

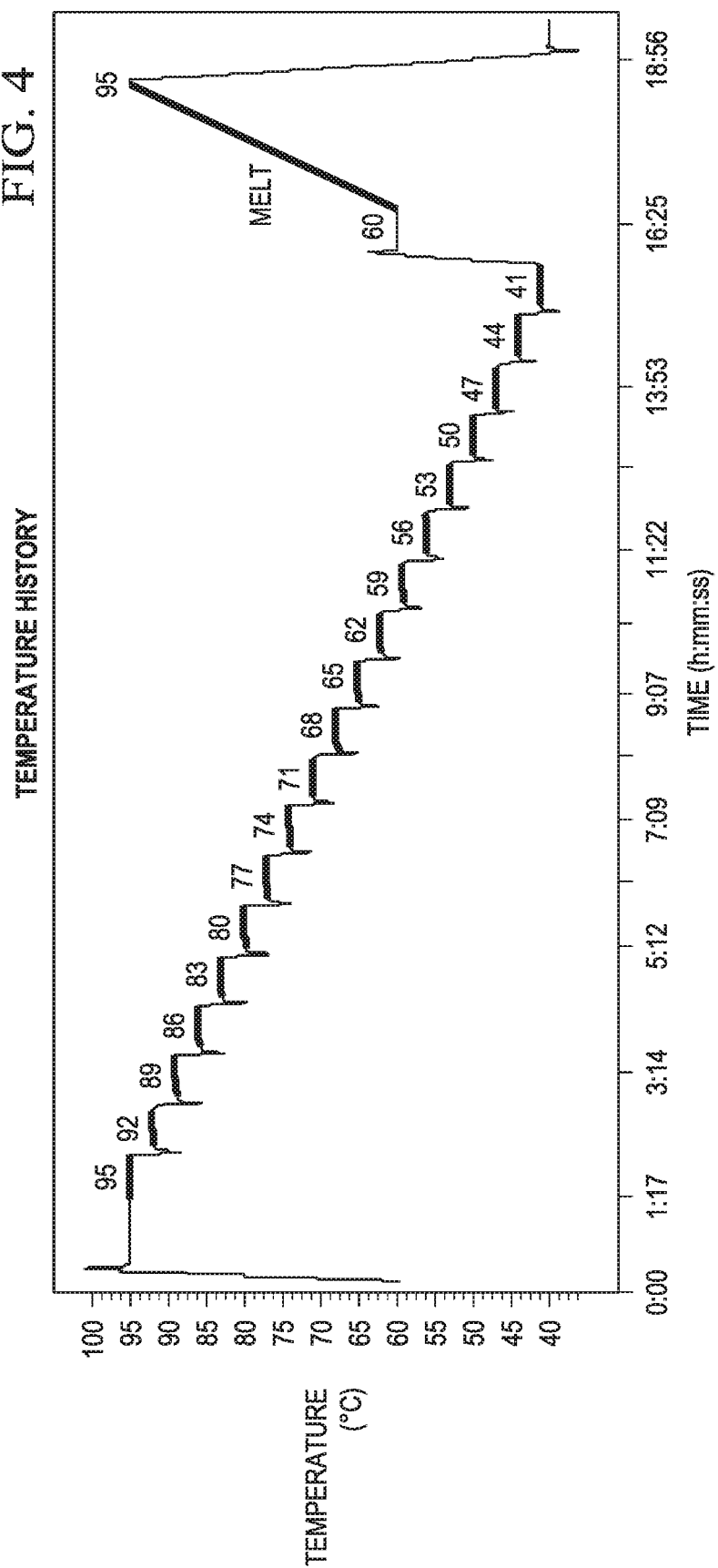

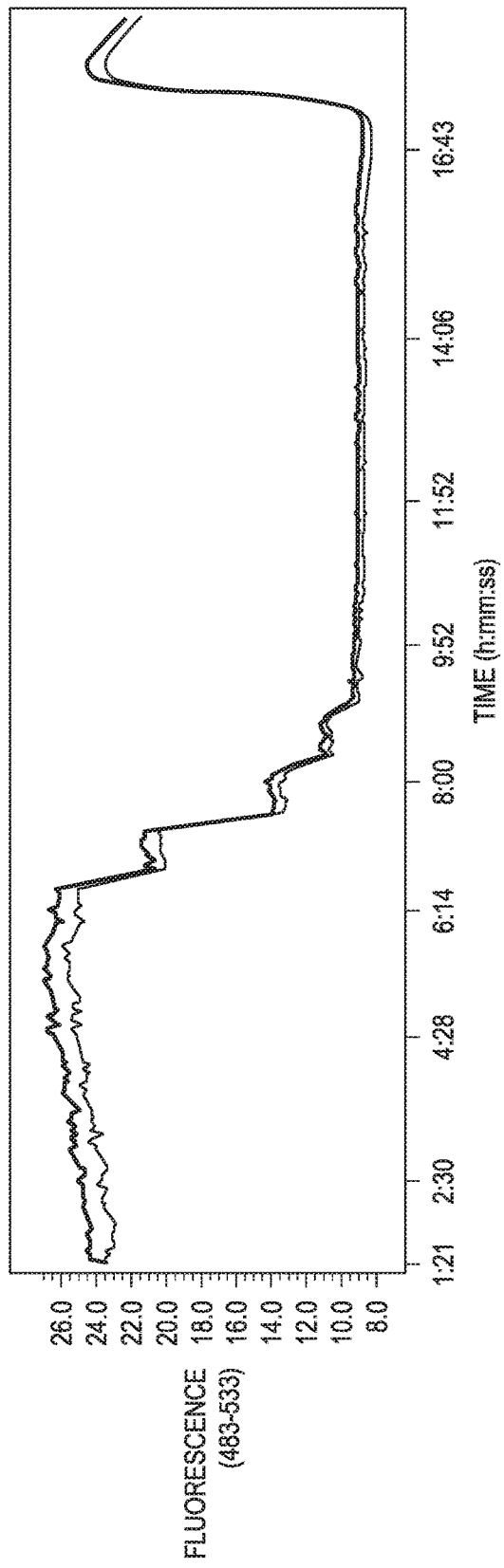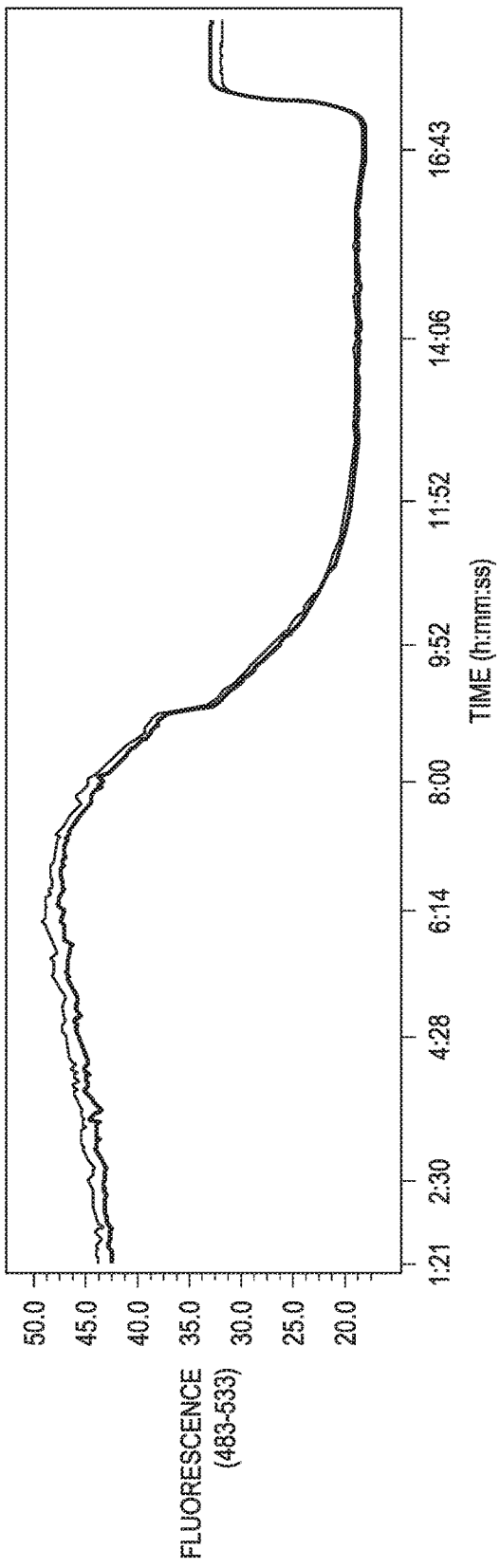

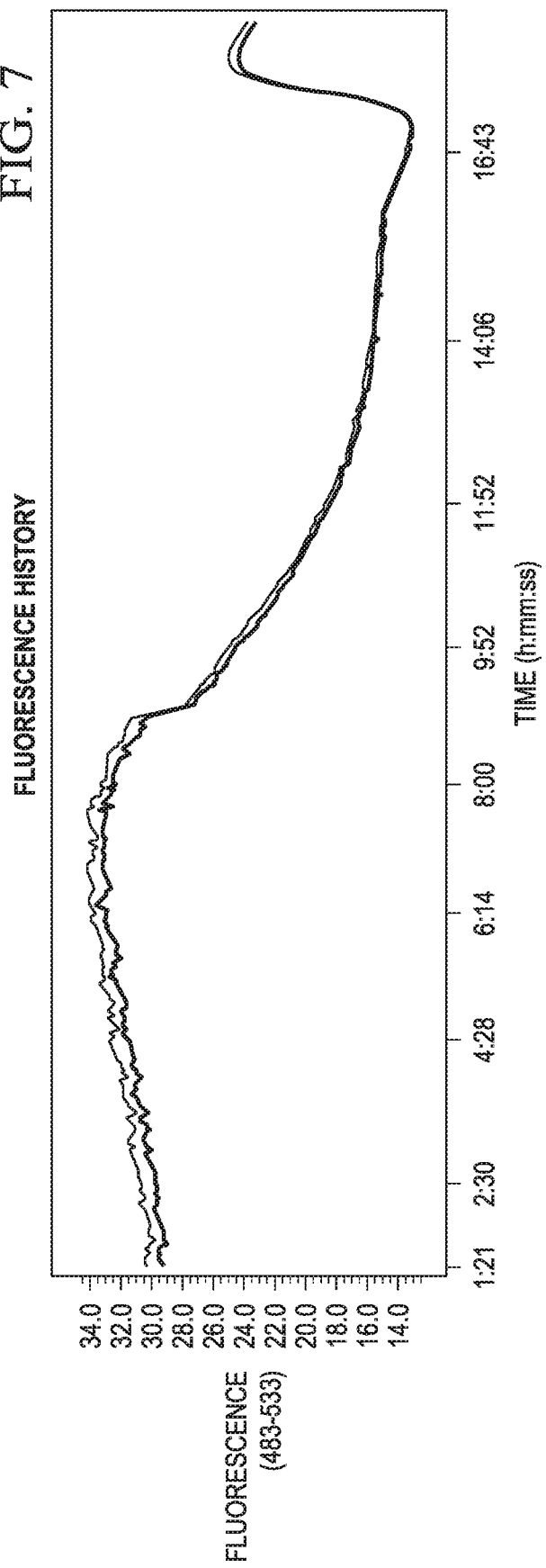

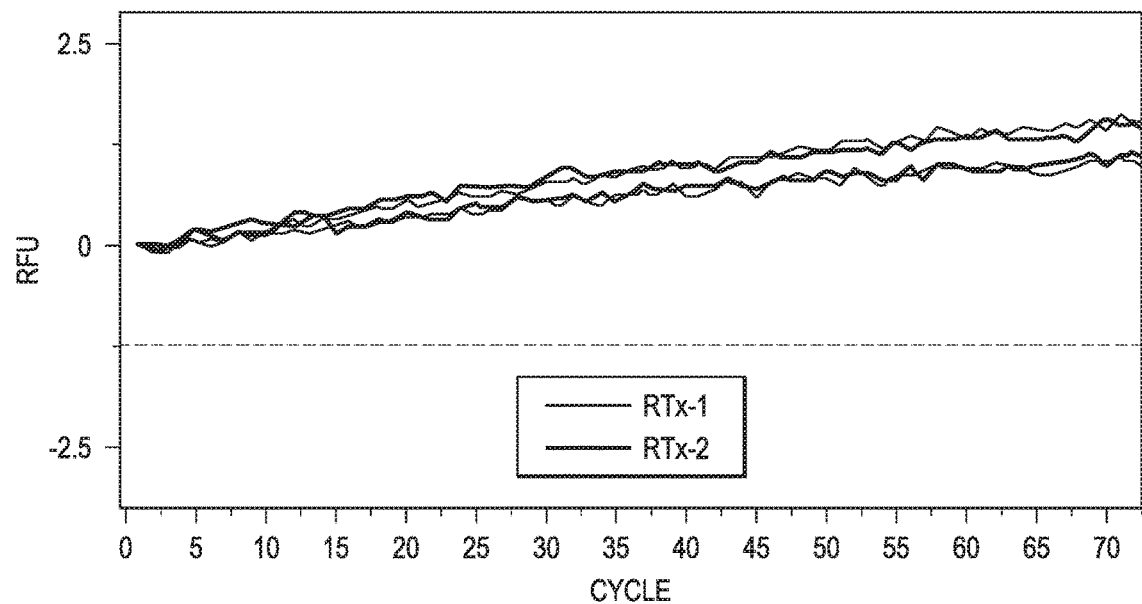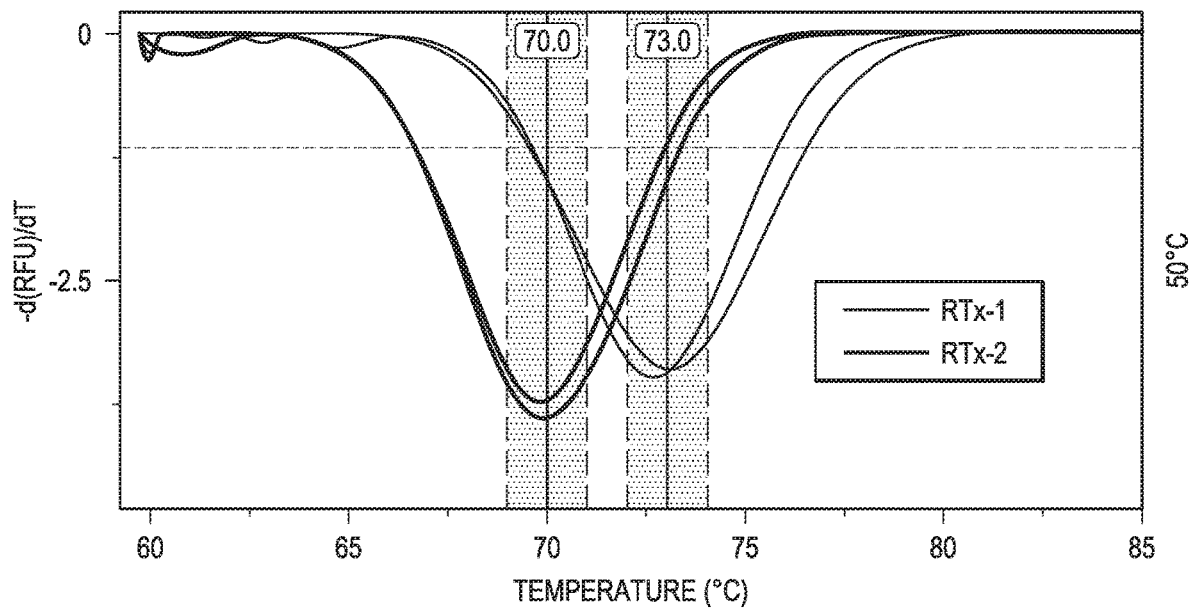
FIG. 8A

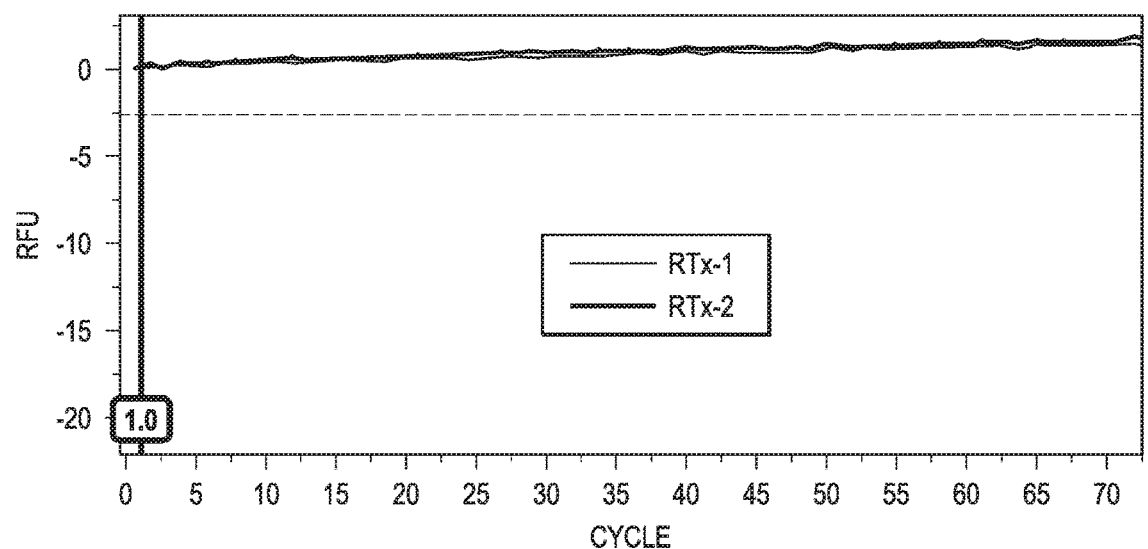
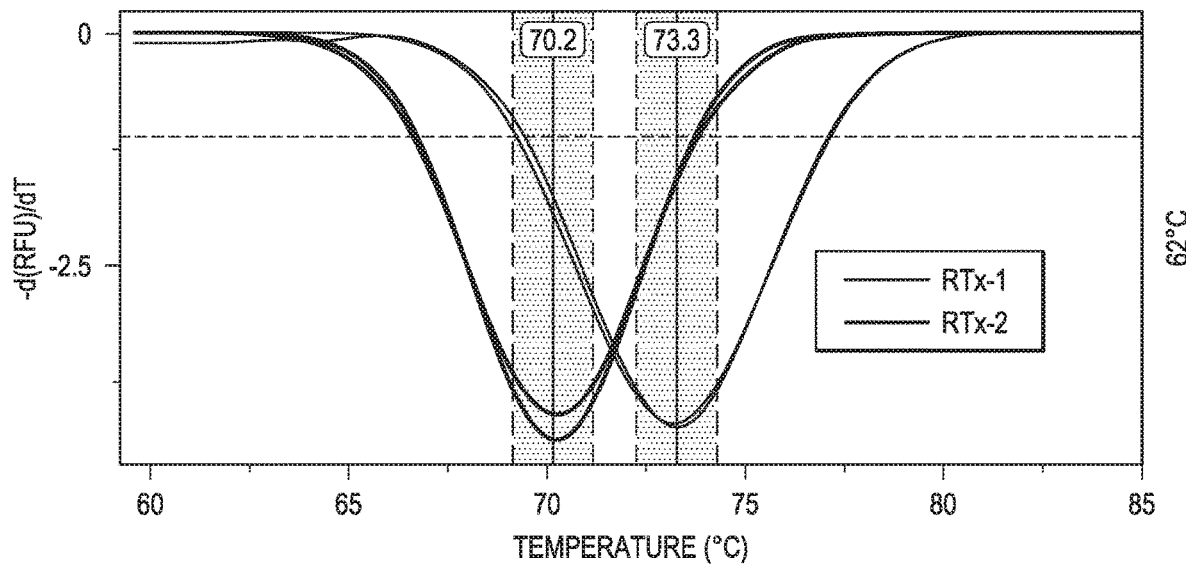
FIG. 8B

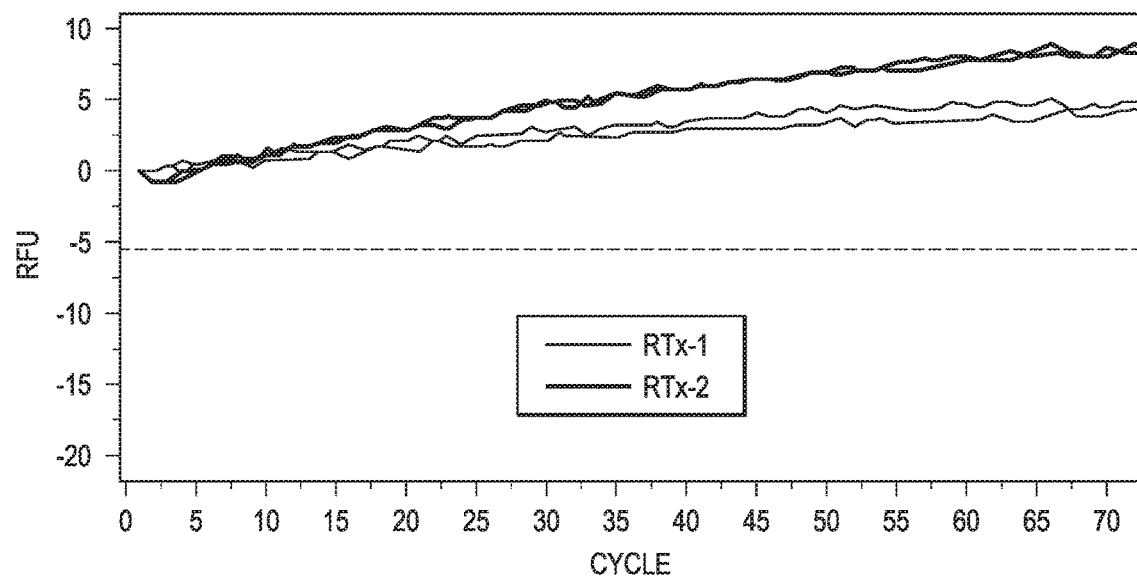
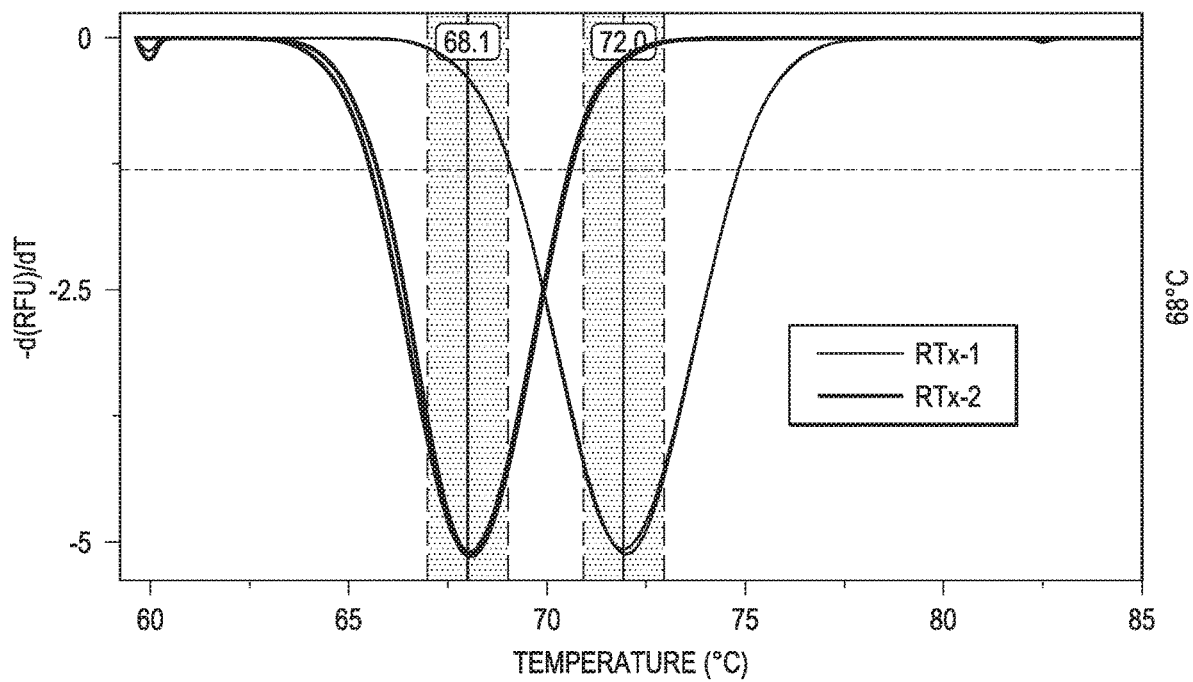
FIG. 8C

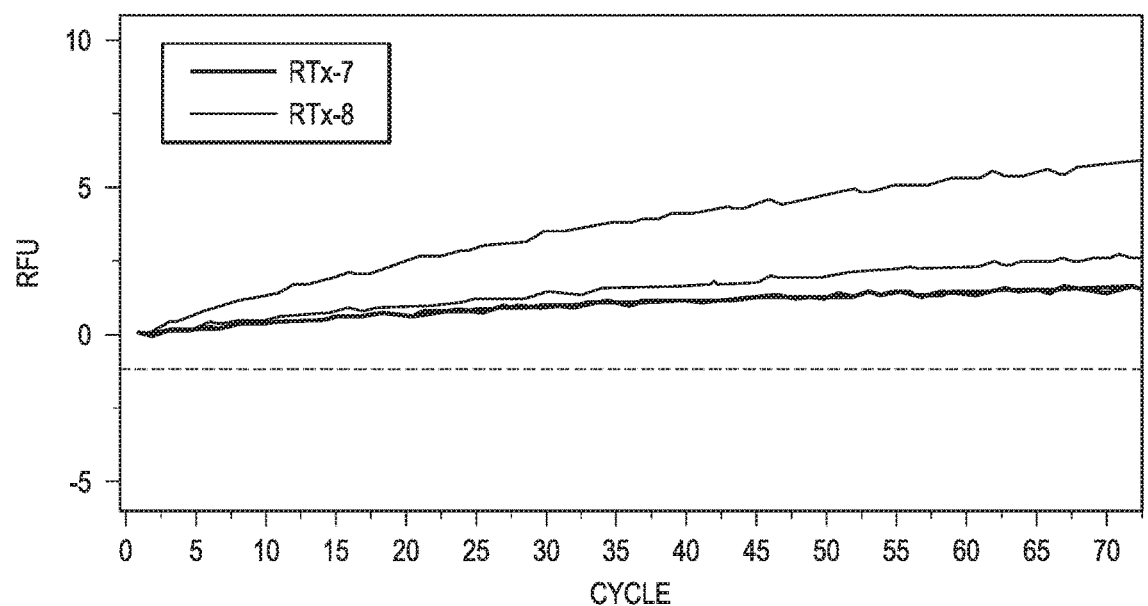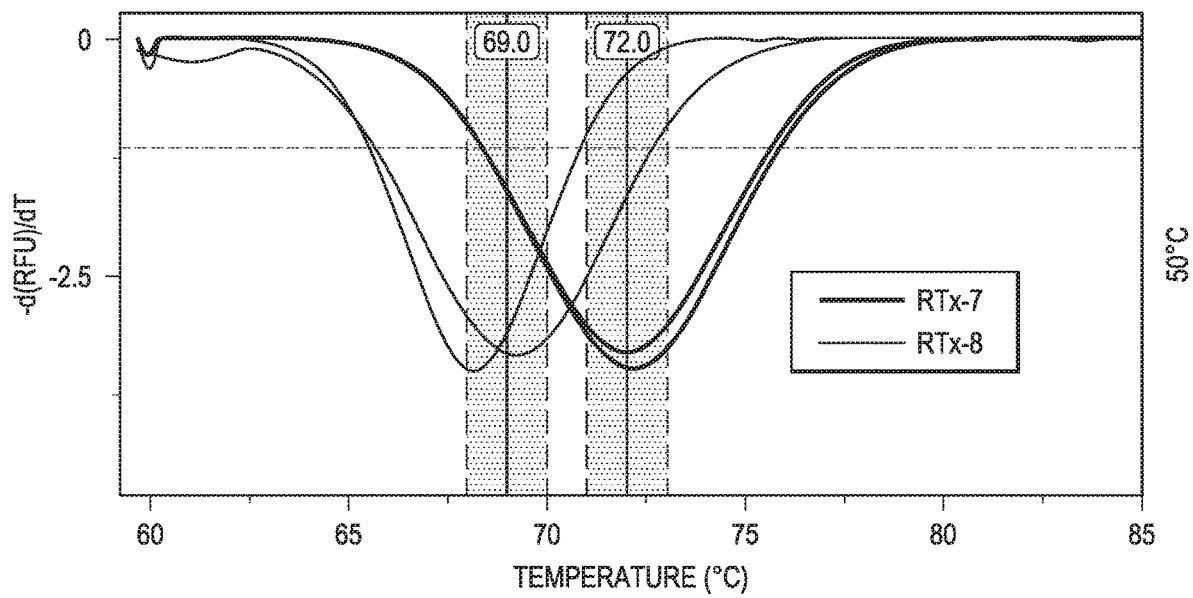
FIG. 9A

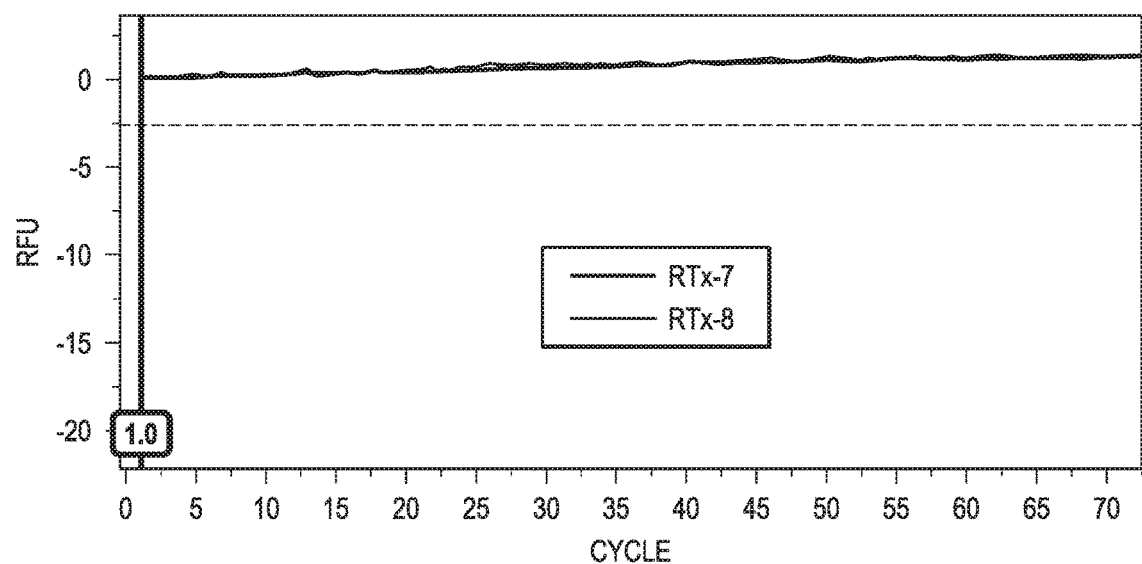
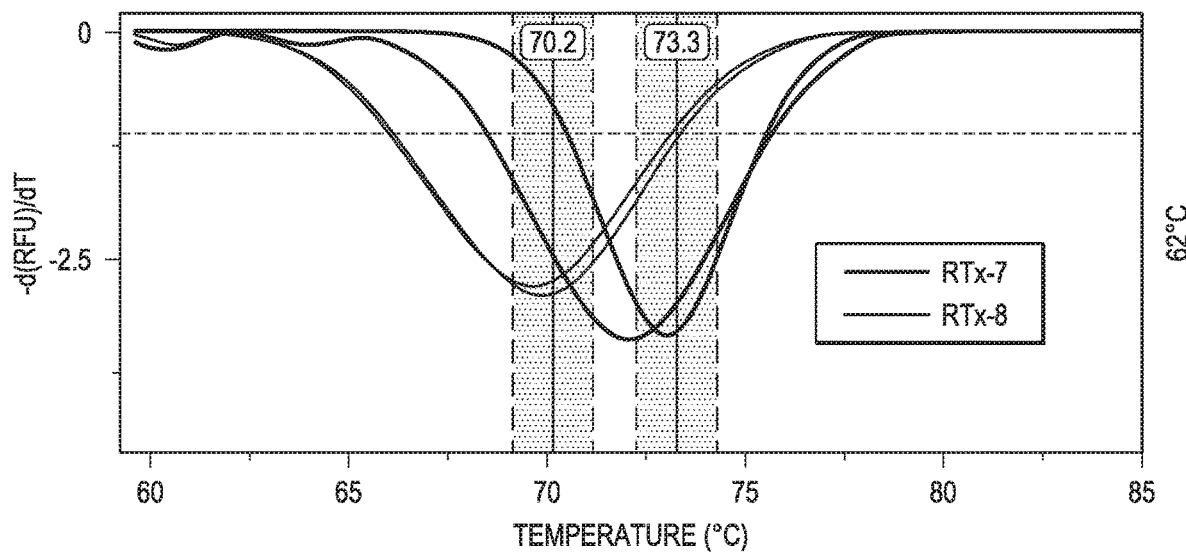
FIG. 9B

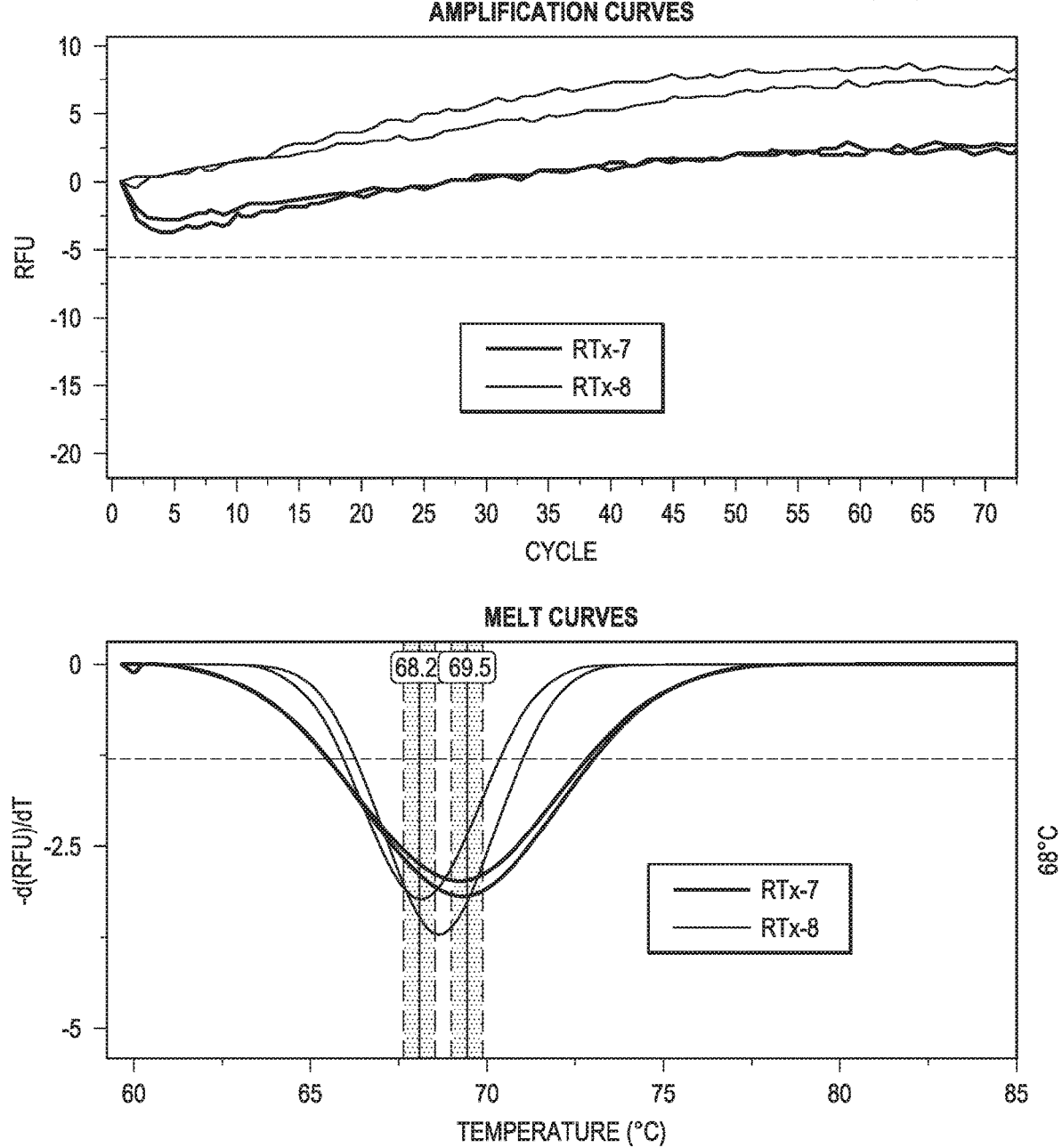

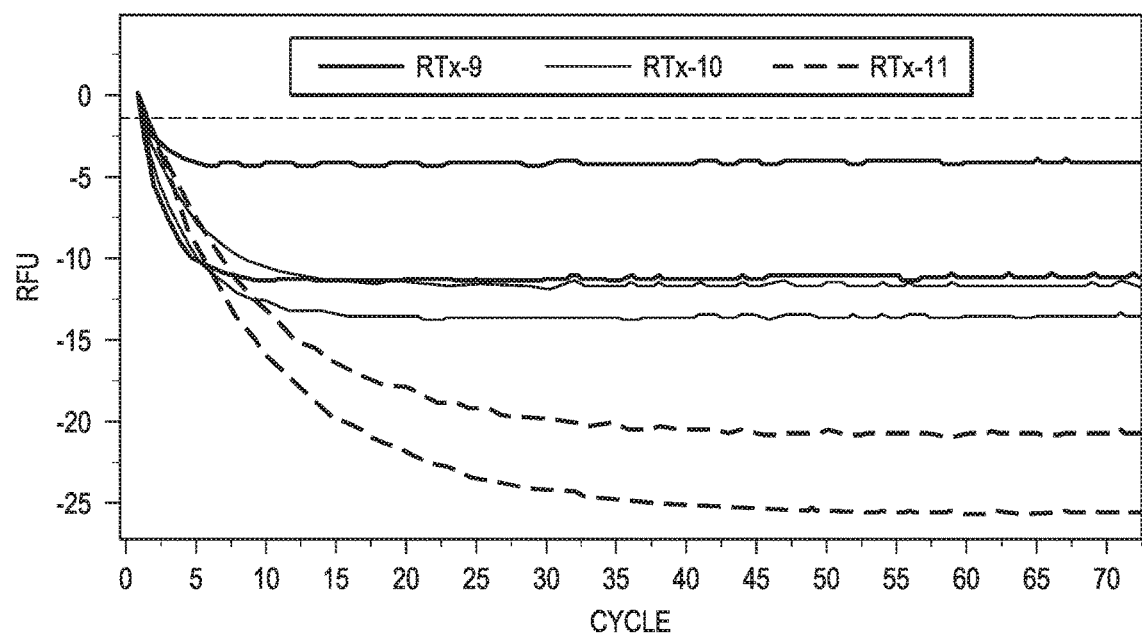
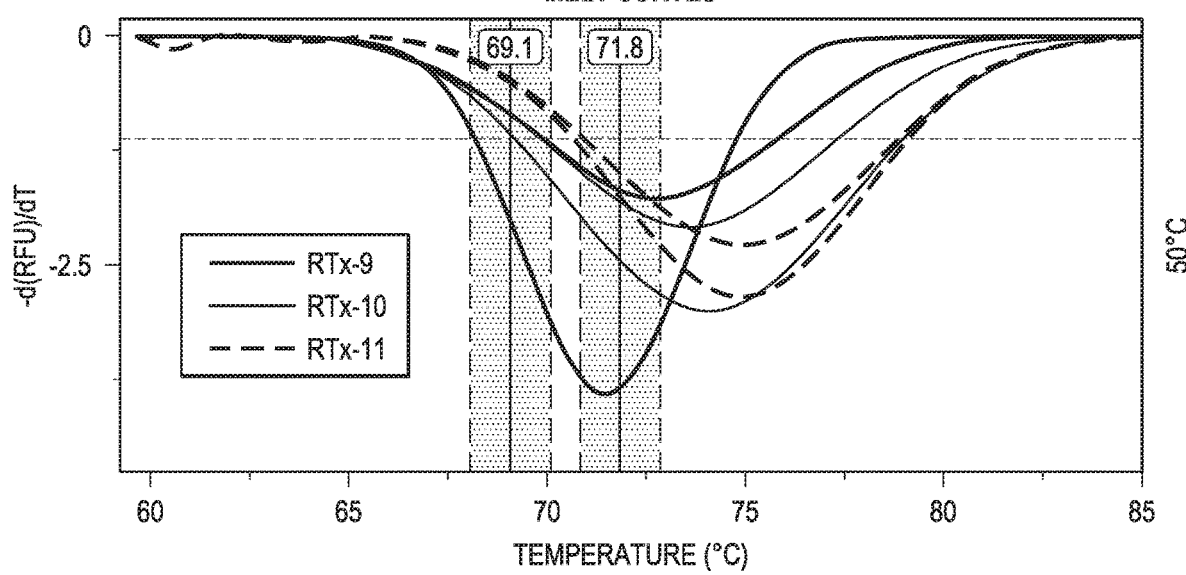
FIG. 10A

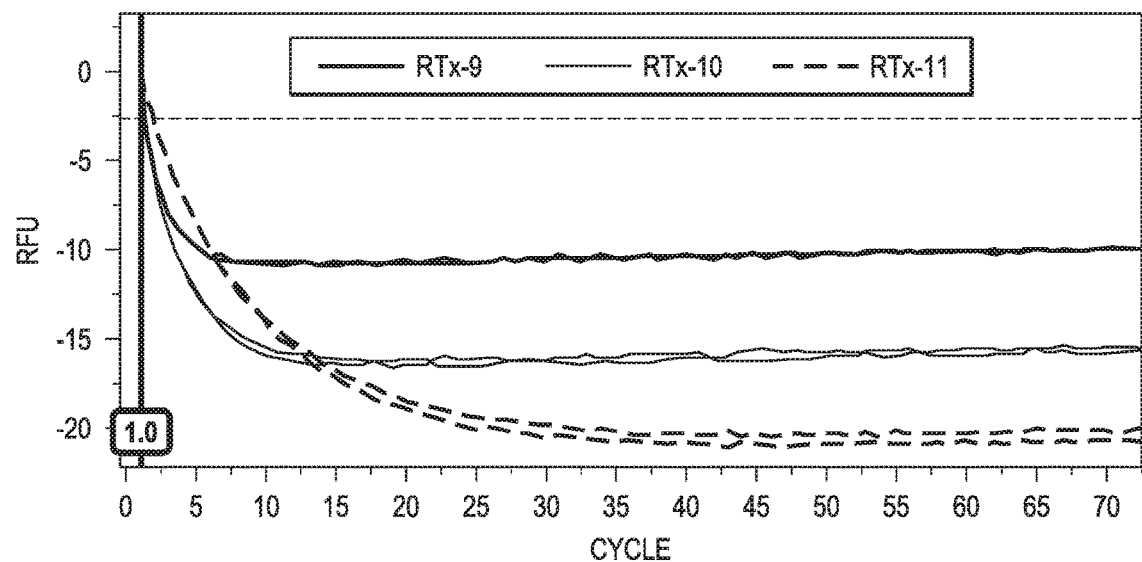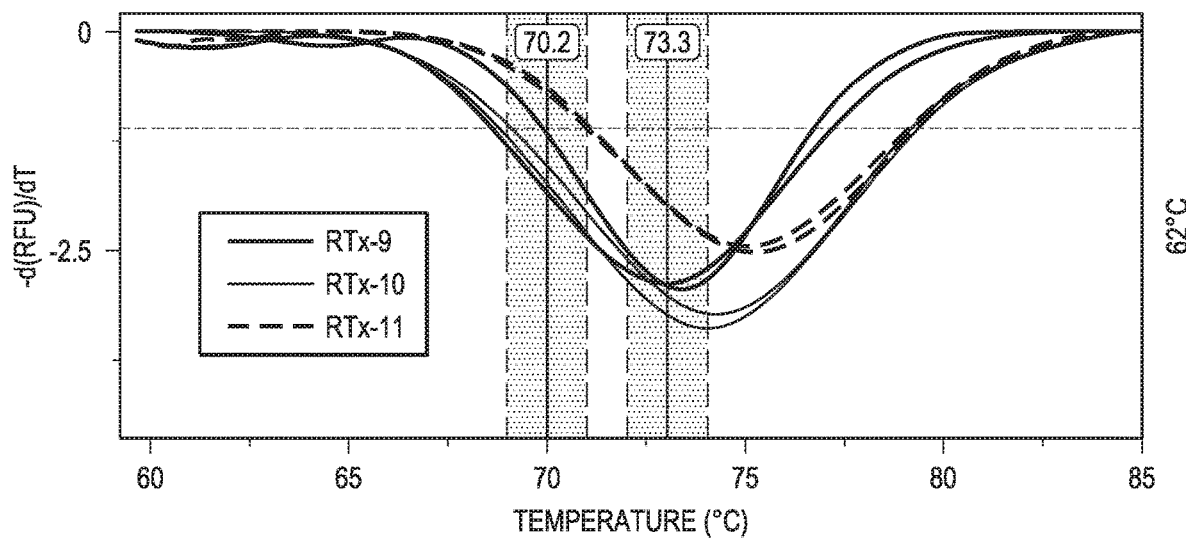
FIG. 10B

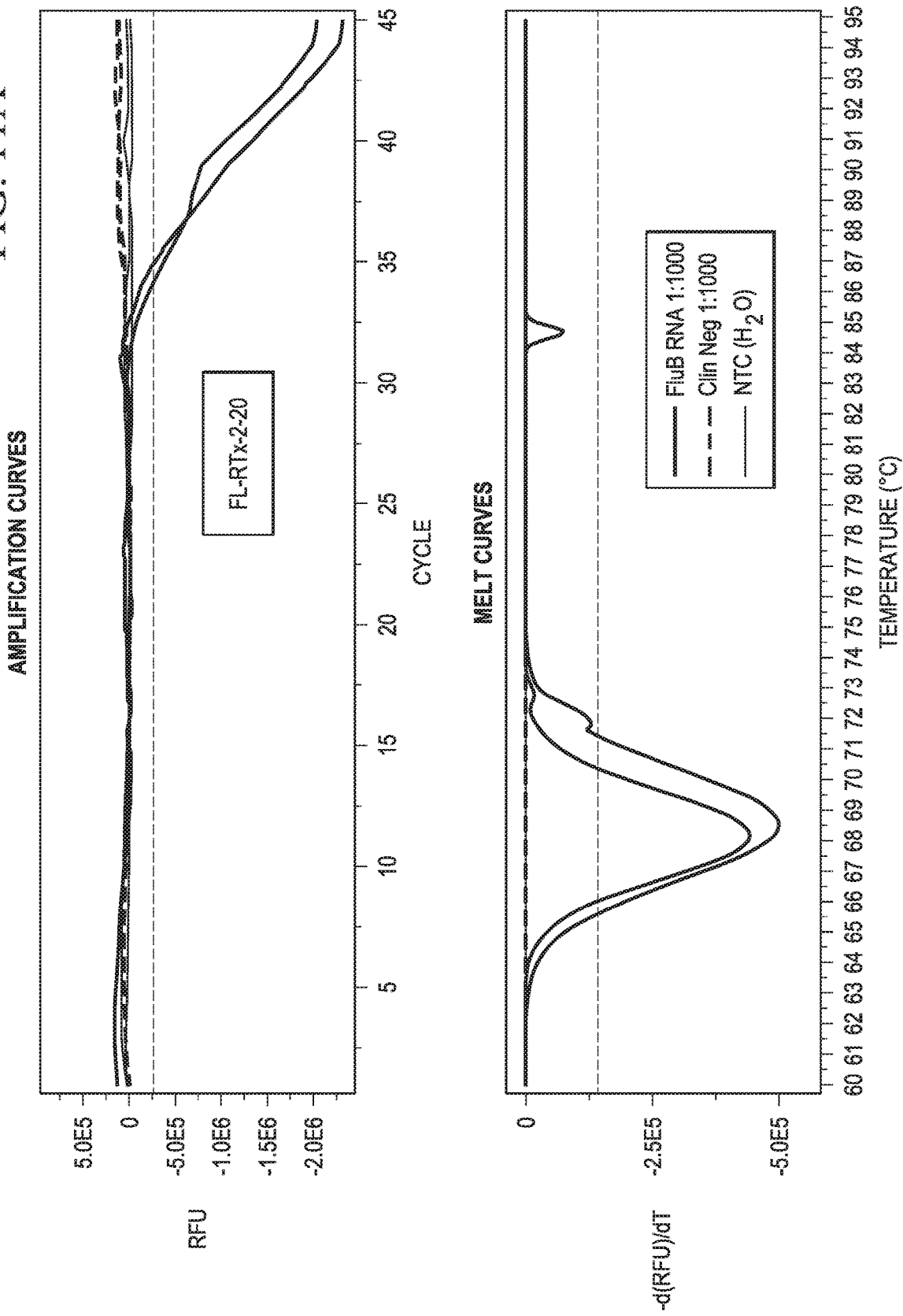

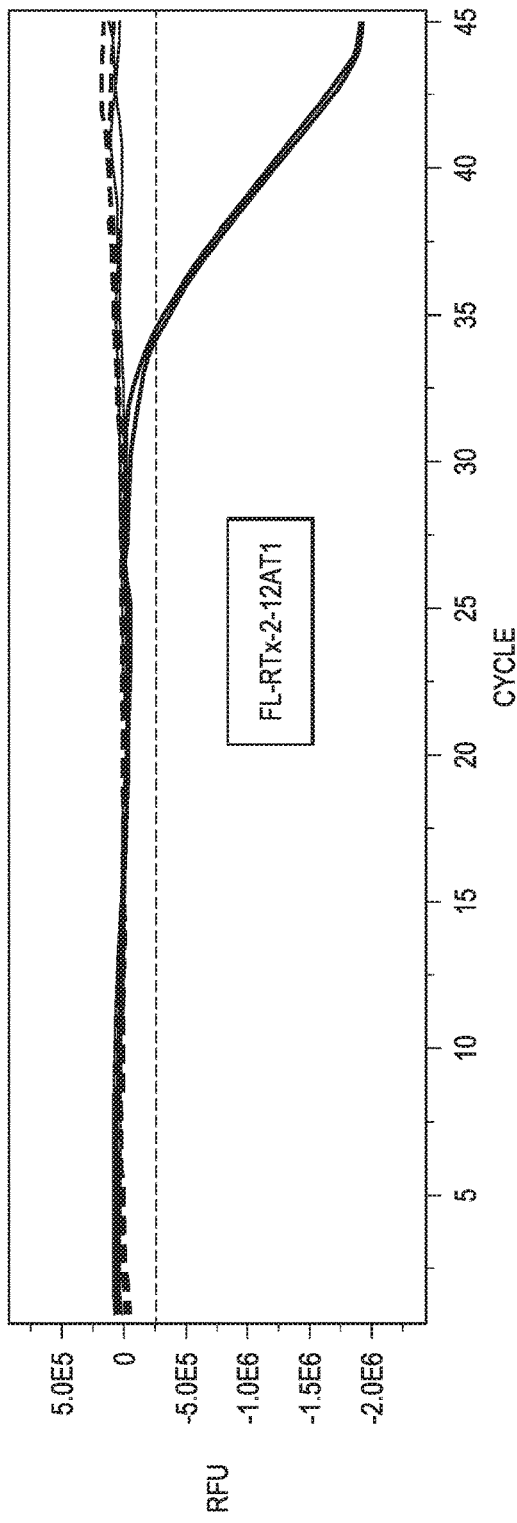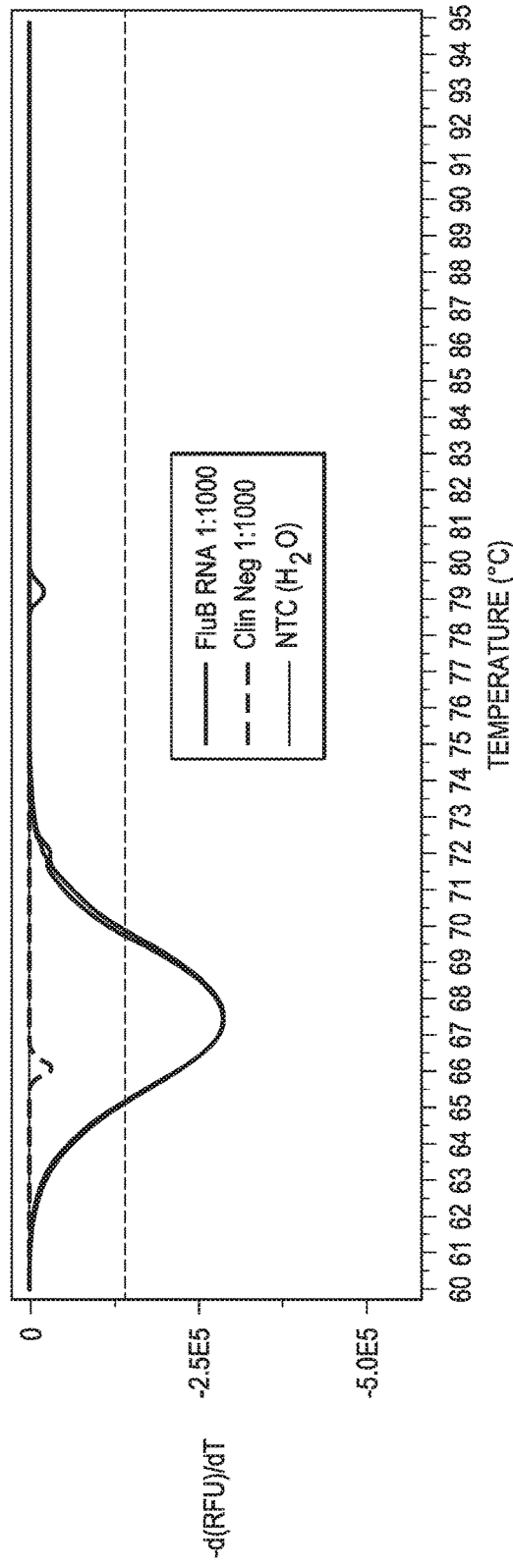
FIG. 11B

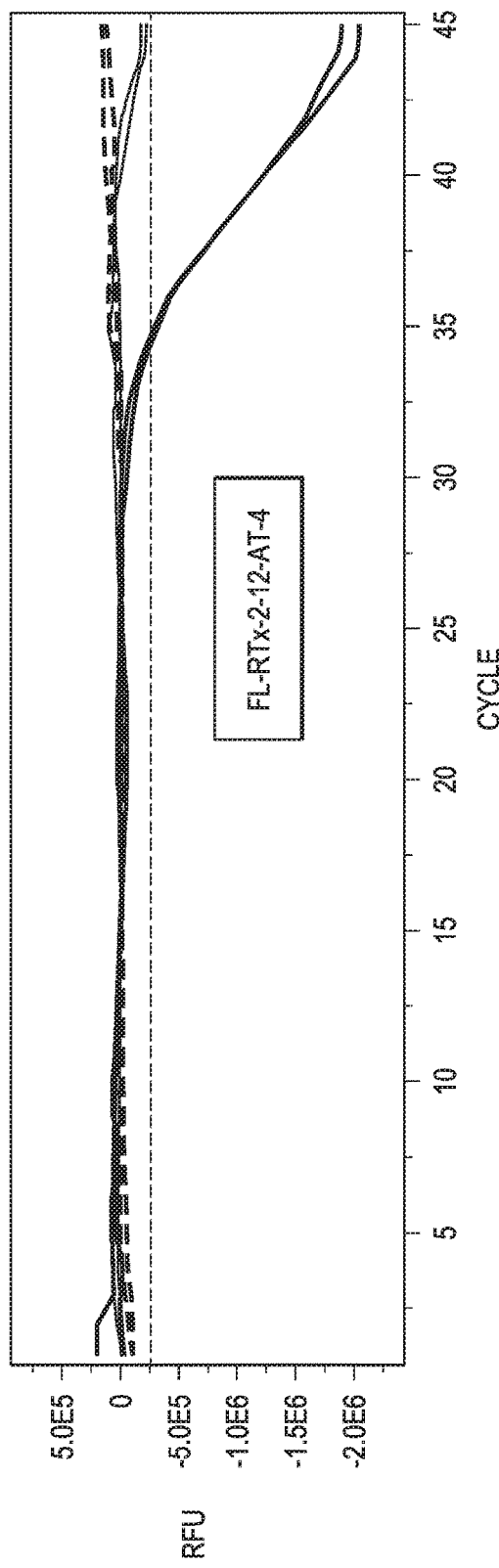
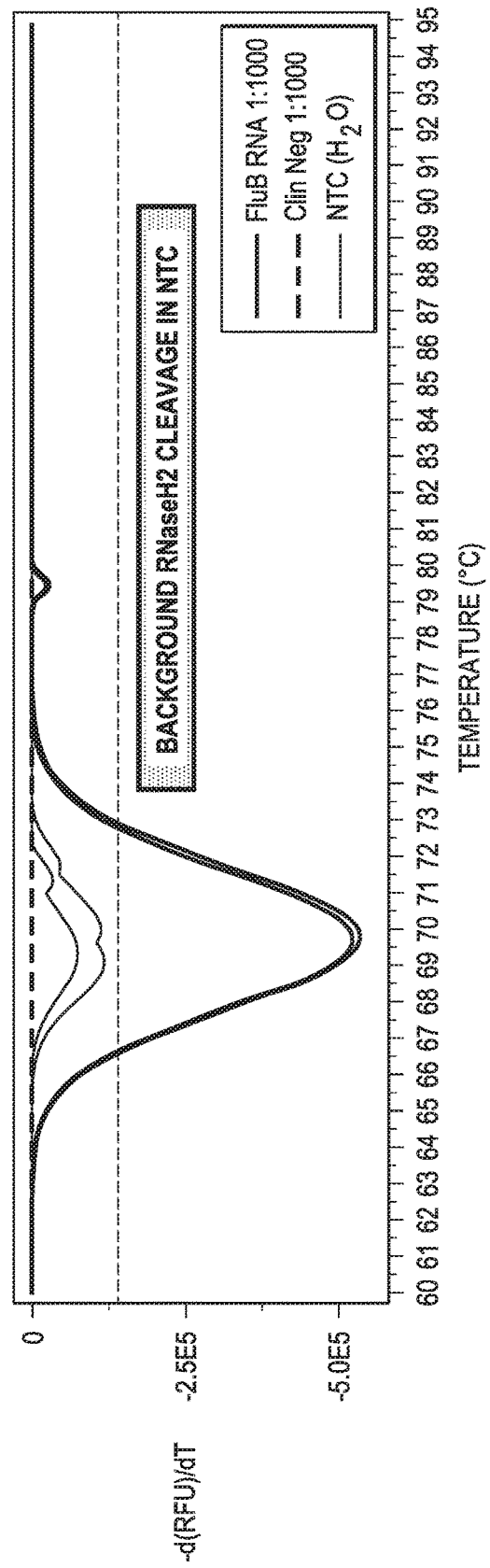
FIG. 11D

PROBES FOR IMPROVED MELT DISCRIMINATION AND MULTIPLEXING IN NUCLEIC ACID ASSAYS

This application is a continuation of U.S. patent application Ser. No. 14/823,288, filed Aug. 11, 2015 which claims the benefit of U.S. Provisional Patent Application No. 62/035,783, filed Aug. 11, 2014, the entirety of which is incorporated herein by reference.

INCORPORATION OF SEQUENCE LISTING

The sequence listing that is contained in the file named "LUMNP0129ST25.txt", which is 8 KB (as measured in Microsoft Windows®) and was created on Aug. 10, 2015, is filed herewith by electronic submission and is incorporated by reference herein.

BACKGROUND OF THE INVENTION

1. Field of the Invention

The present invention relates generally to the field of molecular biology. More particularly, it concerns the detection of nucleic acids.

2. Description of Related Art

Polymerase chain reaction (PCR) is a molecular biology technique for enzymatically replicating DNA without using a living organism. PCR is commonly used in medical and biological research labs for a variety of tasks, such as the detection of hereditary diseases, the identification of genetic fingerprints, the diagnosis of infectious diseases, the cloning of genes, paternity testing, and DNA computing. PCR has been accepted by molecular biologists as the method of choice for nucleic acid detection because of its unparalleled amplification and precision capability. DNA detection is typically performed at the end-point, or plateau phase of the PCR reaction, making it difficult to quantify the starting template. Real-time PCR or kinetic PCR advances the capability of end-point PCR analysis by recording the amplicon concentration as the reaction progresses. Amplicon concentration is most often recorded via a fluorescent signal change associated with the amplified target. Real-time PCR is also advantageous over end-point detection in that contamination is limited because it can be performed in a closed system. Other advantages include greater sensitivity, dynamic range, speed, and fewer processes required.

Several assay chemistries have been used in real-time PCR detection methods. These assay chemistries include using double-stranded DNA binding dyes, dual-labeled oligonucleotides, such as hairpin primers, and hairpin probes. However, a drawback of current real-time PCR is its limited multiplexing capability. Current real-time PCR technologies use reporter fluorochromes that are free in solution. This design necessitates the use of spectrally distinct fluorochromes for each assay within a multiplex reaction. For example, a multiplex reaction designed to detect 4 target sequences would require an instrument capable of distinguishing 4 different free floating fluorochromes by spectral differentiation, not including controls. These requirements not only limit the practical multiplexing capability, but also increase costs since such instruments typically require multiple emission sources, detectors, and filters. Current real-time PCR technologies have multiplexing capabilities from about 1-6 plex.

SUMMARY OF THE INVENTION

The present invention relates to systems and methods for amplification and detection of DNA. In particular, embodiments of the present invention provide systems and methods that greatly increase multiplexing capabilities of detectable probes for use in detecting amplified target sequences.

In a first embodiment, a method is provided for detecting the presence of a target nucleic acid comprising: (a) contacting a sample with a cleavable probe, said probe comprising, from 5' to 3', (i) a first sequence region comprising a label; (ii) a second sequence region; (iii) a sequence that is the reverse complement of the second sequence region; and (iv) a sequence comprising one or more ribonucleotide base that is complimentary to a first region on a first strand of the target nucleic acid; (b) contacting the cleavable probe with an endoribonuclease, thereby cleaving probe that is hybridized with target nucleic acid to form a truncated cleavable probe; (c) allowing the truncated cleavable probe to hybridize to itself to form a hairpin probe; (d) extending the hairpin probe; and (e) detecting the target nucleic acid by detecting a change in signal from the label. In certain aspects, the label in first sequence region (i) is: a reporter-quencher pair and extension of the hairpin probe on the first sequence region changes the distance between the reporter and quencher; or at least one non-natural nucleotide labeled with a first member of a reporter-quencher pair and extension of the hairpin probe on the first sequence region results in the incorporation of a complementary non-natural nucleotide labeled with a second member of the reporter-quencher pair. In certain aspects, all of, a portion of, or none of the sequence that is the reverse complement of the second sequence region (iii) may be complimentary to a first region on a first strand of the target nucleic acid. In some embodiments, the method further comprises performing a melt analysis on the hairpin probe.

In one embodiment, a method is provided for detecting the presence of a target nucleic acid comprising: (a) contacting the sample with a cleavable probe, said probe comprising, from 5' to 3', (i) a first sequence region comprising at least one non-natural nucleotide labeled with a first member of a reporter-quencher pair; (ii) a second sequence region; (iii) a sequence that is the reverse complement of the second sequence region; and (iv) a sequence comprising one or more ribonucleotide base that is complimentary to a first region on a first strand of the target nucleic acid; (b) contacting the cleavable probe with an endoribonuclease, thereby cleaving probe that is hybridized with target nucleic acid to form a truncated cleavable probe; (c) allowing the truncated cleavable probe to hybridize to itself to form a hairpin probe; (d) extending the hairpin probe in the presence of a non-natural nucleotide labeled with a second member of the reporter-quencher pair that is capable of base-pairing with the at least one non-natural nucleotide of the first sequence region; and (e) detecting the target nucleic acid by detecting a change in signal from the label on the cleavable probe and the hairpin probe. In certain aspects, a portion of the sequence that is the reverse complement of the second sequence region (iii) may be complimentary to a first region on a first strand of the target nucleic acid. In some embodiments, the method further comprises performing a melt analysis on the hairpin probe.

In another embodiment, a method is provided for detecting the presence of a target nucleic acid comprising: (a) contacting a sample with a cleavable probe, said probe comprising, from 5' to 3', (i) a first sequence region labeled with a reporter-quencher pair; (ii) a second sequence region;

(iii) a sequence that is the reverse complement of the second sequence region; and (iv) a sequence comprising one or more ribonucleotide base that is complimentary to a first region on a first strand of the target nucleic acid; (b) contacting the cleavable probe with an endoribonuclease, thereby cleaving the cleavable probe that is hybridized with the target nucleic acid to form a truncated probe; (c) allowing the truncated probe to hybridize to itself to form a hairpin probe; (d) extending the hairpin probe onto the first sequence region such that the distance between the reporter and quencher is increased; and (e) detecting the target nucleic acid by detecting a change in signal from the reporter. In certain embodiments, one member of the reporter-quencher pair is at the 5' end of the cleavable probe. In some embodiments, one member of the reporter-quencher pair is at the 5' end of the first sequence region and the other member of the reporter-quencher pair is at the 3' end of the first sequence region. In certain embodiments, the reporter is a fluorescent dye. In certain aspects, all of, a portion of, or none of the sequence that is the reverse complement of the second sequence region (iii) may be complimentary to a first region on a first strand of the target nucleic acid. In some embodiments, the method further comprises performing a melt analysis on the hairpin probe.

In certain aspects, the cleavable probe may further comprise (v) a loop sequence of one or more nucleotides between the second sequence region and the sequence that is the reverse complement of the second sequence region. In some aspects, the loop sequence may be 4-20, 6-15 or 10-15 nucleotides in length. In some aspects, the loop sequence may comprise at least 3-5 consecutive A nucleotides. In some embodiments, the loop sequence comprises one or more polymerase extension blocking moieties. In certain aspects the loop sequence may comprise a combination of one or more nucleotides and one or more extension blocking moieties. Polymerase extension blocking moieties may be used as part or all of a loop sequence. Examples of extension blocking moieties include carbon spacers. Carbon spacers may include spacers that may be 3 to 36 carbon atoms in length. Common examples of internal oligonucleotide carbon spacers include spacers that are 3, 9, and 18 carbon atoms in length. Carbon spacers may be used to prevent the cleavable probes from forming non-specific double stranded PCR products. Carbon spacers may also be used to adjust the melt temperature (Tm) of the hairpin probe. Other polymerase extension blocking moieties may include non-natural nucleotides, ribonucleotides, or any other non-nucleotide chemical moiety.

In certain aspects, the second sequence region may be 6-20 nucleotides in length. In certain aspects, the second sequence region compliment may be 6-20 nucleotides in length. In certain aspects, the first sequence region may be 4-20 nucleotides in length. In certain aspects, the sequence that is complimentary to a first region on a first strand of the target nucleic acid may be 6-50, 10-50, or 6-30 nucleotides in length. In certain aspects, the one or more ribonucleotide bases of the cleavable probe may be positioned just 3' of the sequence that is the reverse complement of the second sequence region (also referred to herein as the second sequence region compliment). In certain aspects, the one or more ribonucleotide bases of the cleavable probe may be positioned at least 4 bases from the 3' end of the sequence that is complimentary to a first region on a first strand of the target nucleic acid. As mentioned above, all of, a portion of, or none of the sequence that is the reverse complement of the second sequence region may be complimentary to a first region on a first strand of the target nucleic acid.

In certain aspects, the cleavable probe may comprise a sequence comprising 1 to 5 ribonucleotide bases that is complimentary to a first region on a first strand of the target nucleic acid sequence. In some aspects, the cleavable probe may comprise a sequence comprising 3 to 5 ribonucleotide bases that is complimentary to a first region on a first strand of the target nucleic acid sequence.

In certain aspects, the cleavable probe may comprise non-base pairing modifications, which may be placed 3' and/or 5' of the ribobase and within the sequence of that probe that is otherwise complimentary to the first region on the first strand of the target nucleic acid. These modifications may include natural or non-natural nucleotides that do not base pair with the target sequence, or may include carbon spacers or other non-nucleotide chemical moieties. Placing non-base pairing modifications upstream or downstream of the ribonucleotide, but within a region of the probe that is otherwise complimentary to the target sequence, may improve specificity of the cleavable probe. The non-base pairing moiety may be positioned between 2 and 20 nucleotides upstream or downstream from the ribonucleotide. In certain embodiments, the non-base pairing moiety is placed 1, 2, 3, 4, or 5, or any range therein, nucleotides upstream or downstream of the ribonucleotide.

In certain aspects, the at least a one non-natural nucleotide labeled with a first member of a reporter-quencher pair may be positioned at the 5' end of the cleavable probe. In certain aspects, the cleavable probe may comprise an extension-blocking modification at the 3' end. In certain aspects, the second sequence region of the cleavable probe may comprise a G/C content of at least 50%. In certain aspects, the second sequence region of the cleavable probe may be 6-15 nucleotides in length.

In certain aspects, the second sequence region of the cleavable probe may comprise one or more non-natural bases. In certain aspects, after endoribonuclease or 5'-nuclease cleavage, the truncated cleavable probe and the target nucleic acid may have a melt point of less than 55° C.

In certain aspects, the first member of a reporter-quencher pair may be a reporter. In certain aspects, the reporter for use in the instant embodiments may be a fluorophore. Accordingly, in some cases, a change is the signal may be a decrease in a fluorescent signal. In certain aspects, detecting a change in signal from the label may comprise detecting a change (or rate of change) in signal from a reporter, such as unquenching of a signal, as the temperature of the sample is changed. In some aspects, detecting a change in signal from the reporter may comprise detecting a change in signal from the reporter as the temperature of the sample is increased above (or decreased below) the melt point of hairpin probe.

In certain aspects, the cleavable probe may be attached to a solid support.

Certain aspects of the embodiments concern the use of at least one non-natural nucleotide (iv). In some aspects, the non-natural nucleotide is an isobase, such as iso-guanine (isoG) or iso-cytosine (isoC). In certain aspects, the at least one non-natural nucleotide or the quencher-labeled non-natural nucleotide may be isoG and the other may be isoC.

In a further aspect, the method may comprise (a) contacting the sample with a second (or further) cleavable probe, said probe comprising, from 5' to 3', (i) a first sequence region comprising at least a one non-natural nucleotide labeled with a first member of a reporter-quencher pair; (ii) a second sequence region; (iii) a sequence that is the reverse complement of the second sequence region; and (iv) a sequence comprising one or more ribonucleotide base that is complimentary to a first region on a first strand of a second (or further) target nucleic acid; (b) contacting the cleavable probe with an endoribonuclease, thereby cleaving probe that is hybridized with target nucleic acid to form a truncated cleavable probe; (c) allowing the truncated cleavable probe to hybridize to itself to form a hairpin probe; (d) extending the hairpin probe in the presence of a non-natural nucleotide labeled with a second member of a reporter-quencher pair that is capable of base-pairing with the at least one non-natural nucleotide of the first sequence region; and (e) detecting the second (or further) target nucleic acid by detecting a change in signal from the label on the cleavable probe and the hairpin probe. For example, detecting the presence of the first and/or second target nucleic acid may be performed sequentially or essentially simultaneously. In still a further aspect, the first and second probes may comprise distinguishable reporters. In another aspect, the first and second probes may comprise the same reporter and, in some cases, the first and second probes comprise hairpins with distinguishable melt points (e.g., melt points that differ by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30° C. from one another, or any range derivable therein).

In still a further aspect, the method is a multiplex method and comprises (a) contacting the sample with a third, fourth, fifth or sixth cleavable probe, said probe comprising, from 5' to 3', (i) a first sequence region comprising at least a one non-natural nucleotide labeled with a first member of a reporter-quencher pair; (ii) a second sequence region; (iii) a sequence that is the reverse complement of the second sequence region; and (iv) a sequence comprising one or more ribonucleotide base that is complimentary to a first region on a first strand of a third, fourth, fifth or sixth target nucleic acid; (b) contacting the cleavable probe with an endoribonuclease, thereby cleaving probe that is hybridized with target nucleic acid to form a truncated cleavable probe; (c) allowing the truncated cleavable probe to hybridize to itself to form a hairpin probe; (d) extending the hairpin probe in the presence of a non-natural nucleotide labeled with a second member of a reporter-quencher pair that is capable of base-pairing with the at least one non-natural nucleotide of the first sequence region; and (e) detecting the third, fourth, fifth or sixth target nucleic acid by detecting a change in signal from the label on the cleavable probe and the hairpin probe. For example, detecting the presence of the first and/or second target nucleic acid may be performed sequentially or essentially simultaneously. In still a further aspect, the first and second probes may comprise distinguishable reporters. In another aspect, the first and second probes may comprise the same reporter and, in some cases, the hairpin probes formed by the first and second probes may comprise distinguishable melt points (e.g., melt points that differ by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30° C. from one another, or any range derivable therein). In one aspect, the hairpin probes formed by the first, second, third, fourth, fifth, and/or sixth probes each may comprise a distinguishable label or a distinguishable melt point.

In another embodiment, the method may comprise (a) contacting the sample with a second (or further) cleavable probe, said probe comprising, from 5' to 3', (i) a first sequence region comprising a reporter-quencher pair; (ii) a second sequence region; (iii) a sequence that is the reverse complement of the second sequence region; and (iv) a sequence comprising one or more ribonucleotide base that is complimentary to a first region on a first strand of a second (or further) target nucleic acid; (b) contacting the cleavable probe with an endoribonuclease, thereby cleaving probe that is hybridized with target nucleic acid to form a truncated cleavable probe; (c) allowing the truncated cleavable probe to hybridize to itself to form a hairpin probe; (d) extending the hairpin probe onto the first sequence region; and (e) detecting the second (or further) target nucleic acid by detecting a change in signal from the reporter. For example, detecting the presence of the first and/or second target nucleic acid may be performed sequentially or essentially simultaneously. In still a further aspect, the first and second probes may comprise distinguishable reporters. In another aspect, the first and second probes may comprise the same reporter and, in some cases, the first and second probes comprise hairpins with distinguishable melt points (e.g., melt points that differ by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30° C. from one another, or any range derivable therein).

In still a further aspect, the method is a multiplex method and comprises (a) contacting the sample with a third, fourth, fifth or sixth cleavable probe, said probe comprising, from 5' to 3', (i) a first sequence region comprising at least a one non-natural nucleotide labeled with a first member of a reporter-quencher pair; (ii) a second sequence region; (iii) a sequence that is the reverse complement of the second sequence region; and (iv) a sequence comprising one or more ribonucleotide base that is complimentary to a first region on a first strand of a third, fourth, fifth or sixth target nucleic acid; (b) contacting the cleavable probe with an endoribonuclease, thereby cleaving probe that is hybridized with target nucleic acid to form a truncated cleavable probe; (c) allowing the truncated cleavable probe to hybridize to itself to form a hairpin probe; (d) extending the hairpin probe in the presence of a non-natural nucleotide labeled with a second member of a reporter-quencher pair that is capable of base-pairing with the at least one non-natural nucleotide of the first sequence region; and (e) detecting the third, fourth, fifth or sixth target nucleic acid by detecting a change in signal from the label on the cleavable probe and the hairpin probe. For example, detecting the presence of the first and/or second target nucleic acid may be performed sequentially or essentially simultaneously. In still a further aspect, the first and second probes may comprise distinguishable reporters. In another aspect, the first and second probes may comprise the same reporter and, in some cases, the hairpin probes formed by the first and second probes may comprise distinguishable melt points (e.g., melt points that differ by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30° C. from one another, or any range derivable therein). In one aspect, the hairpin probes formed by the first, second, third, fourth, fifth, and/or sixth probes each may comprise a distinguishable label or a distinguishable melt point.

Thus, in some further aspects, a multiplex method according to the embodiments can comprise the use of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more distinct probes, or any range derivable therein, wherein each probe comprises either (1) a distinguishable melt point or (2) a distinguishable label, such that the signal from each distinct probe may be individually discerned. In one aspect, the first, second, third, fourth, fifth and/or sixth cleavable probes each may comprise the same first sequence region, second sequence region and/or the same loop sequence between the second sequence region and the sequence that is the reverse complement of the second sequence region. In certain embodiments, the loop region may comprise one or more polymerase extension blocking moieties.

In a further embodiment, a composition is provided comprising at least a first cleavable probe, said probe comprising, from 5' to 3', (i) a first sequence region comprising a label; (ii) a second sequence region; (iii) a sequence that is the reverse complement of the second sequence region; and (iv) a sequence comprising one or more ribonucleotide base that is complimentary to a first region on a first strand of the target nucleic acid. In certain aspects, the comprising may further comprise a reporter-labeled or quencher-labeled non-natural nucleotide. In certain embodiments, the label in first sequence region (i) is a reporter-quencher pair or at least one non-natural nucleotide labeled with a first member of a reporter-quencher pair.

In one embodiment, a composition is provided comprising at least a first cleavable probe, said probe comprising, from 5' to 3', (i) a first sequence region comprising a at least one non-natural nucleotide labeled with a first member of a reporter-quencher pair; (ii) a second sequence region; (iii) a sequence that is the reverse complement of the second sequence region; and (iv) a sequence comprising one or more ribonucleotide base that is complimentary to a first region on a first strand of the target nucleic acid. In certain aspects, the comprising may further comprise a reporter-labeled or quencher-labeled non-natural nucleotide.

In one embodiment, a composition is provided comprising a cleavable probe, said probe comprising, from 5' to 3', (i) a first sequence region labeled with a fluorophore-quencher pair; (ii) a second sequence region; (iii) a sequence that is the reverse complement of the second sequence region; and (iv) a sequence comprising one or more ribonucleotide base that is complimentary to a first region on a first strand of the target nucleic acid.

In certain aspects, the composition may further comprise a polymerase, an endoribonuclease enzyme, a reference probe or free nucleotides.

In certain aspects, the cleavable probe may further comprise (v) a loop sequence of one or more nucleotides between the second sequence region and the sequence that is the reverse complement of the second sequence region. In some aspects, the loop sequence may be 4-20, 6-15 or 10-15 nucleotides in length. In some aspects, the loop sequence may comprise at least 3-5 consecutive A nucleotides. In some embodiments, the loop sequence comprises one or more polymerase extension blocking moieties. In certain aspects the loop sequence may comprise a combination of one or more nucleotides and one or more extension blocking moieties. Polymerase extension blocking moieties may be used as part or all of a loop sequence. Examples of extension blocking moieties include carbon spacers. Carbon spacers may include spacers that may be 3 to 36 carbon atoms in length. Common examples of internal oligonucleotide carbon spacers include spacers that are 3, 9, and 18 carbon atoms in length. Carbon spacers may be used to prevent the cleavable probes from forming non-specific double stranded PCR products. Carbon spacers may also be used to adjust the melt temperature (Tm) of the hairpin probe. Other polymerase extension blocking moieties may include non-natural nucleotides, ribonucleotides, or any other non-nucleotide chemical moiety.

In a further aspect, the composition may further comprise a second (or further) cleavable probe as described above, wherein different probes may be distinguishable based on having different reporters and or different melt points. For example, a second (or further) probe may comprise, from 5' to 3', (i) a first sequence region comprising at least a one non-natural nucleotide labeled with a first member of a reporter-quencher pair; (ii) a second sequence region; (iii) a sequence that is the reverse complement of the second sequence region; and (iv) a sequence comprising one or more ribonucleotide base that is complimentary to a first region on a first strand of a second (or further) target nucleic acid. In certain aspects, the first and second probes may comprise distinguishable reporters and/or form hairpins having distinguishable melt points. In certain aspects, the cleavable probe may further comprise (v) a loop sequence as discussed above. In some aspects, the composition comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more probes.

In some aspects, a method of the embodiments may further comprise performing multiple polymerase chain reaction cycles. In some aspects, detecting the change in signal from the label comprises detecting the signal before, during, or after performing the multiple polymerase chain reaction cycles. In another aspect, detecting the change in signal from the label comprises detecting the signal only after performing the multiple polymerase chain reaction cycles. In this aspect, the method may further comprise comparing the detected signal from the label to a predetermined ratio of the signal of the label to a reference signal from a label on a non-hybridizing probe.

In some aspects, a method of the embodiments may further comprise quantifying the amount of the target nucleic acid in the sample. For example, quantifying the amount of the target nucleic acid in the sample may comprise: using a standard curve; determining a relative amount of the nucleic acid target; using end-point quantitation; or determining an amount of the nucleic acid target by relating the PCR cycle number at which the signal is detectable over background to the amount of target present.

In a further embodiment, a kit is provided comprising one or more of the compositions disclosed herein. For example, in one embodiment a kit is provided that comprises: (a) a first cleavable probe, said probe comprising, from 5' to 3', (i) a first sequence region comprising at least a one non-natural nucleotide labeled with a first member of a reporter-quencher pair; (ii) a second sequence region; (iii) a sequence that is the reverse complement of the second sequence region; and (iv) a sequence comprising one or more ribonucleotide base that is complimentary to a first region on a first strand of the target nucleic acid; and (b) a reporter-labeled non-natural nucleotide; a quencher-labeled non-natural nucleotide; or an endoribonuclease enzyme. In a further aspect, the kit comprises at least two, three, four, five or six probes. In some embodiments, the probes may further comprise (v) a loop sequence as discussed above. In certain aspects, the probes may comprise distinguishable reporters or form hairpins with distinguishable melt points. In some aspects, the kit may further comprise a polymerase, a reference probe, free nucleotides, or instructions for use of the kit.

In still a further embodiment, a method is provided for detecting the presence of a target nucleic acid comprising: (a) contacting the sample with a first set of probes, said set of probes comprising a cleavable probe comprising, from 5' to 3', (i) a sequence region comprising at least a one non-natural nucleotide labeled with a first member of a reporter-quencher pair; (ii) a capture sequence; and (iii) a sequence comprising one or more ribonucleotide base that is complimentary to a first region on a first strand of the target nucleic acid; and a capture probe comprising, from 5' to 3', (i) a sequence region identical to the sequence region from the cleavable probe and comprising at least one un-labeled non-natural nucleotide identical to the at least one non-natural nucleotide from the cleavable probe; and (ii) a sequence complimentary to capture sequence of the cleavable probe; (b) contacting the cleavable probe with an endoribonuclease, thereby cleaving probe that is hybridized with target nucleic acid to form a truncated cleavable probe; (c) allowing the truncated cleavable probe to hybridize with the capture probe; (d) extending the truncated cleavable probe in the presence of a non-natural nucleotide labeled with a second member of a reporter-quencher pair that is capable of base-pairing with the at least one un-labeled non-natural nucleotide in the capture probe to form an extended cleavable probe; (e) allowing the extended cleavable probe to hybridize to itself to form a hairpin probe; and (f) detecting the target nucleic acid by detecting a change in signal from the label on the cleavable probe and the hairpin probe.

In a further aspect, the method may comprise (a) contacting the sample with a second set of probes, said set of probes comprising a cleavable probe comprising, from 5' to 3', (i) a sequence region comprising at least a one non-natural nucleotide labeled with a first member of a reporter-quencher pair; (ii) a capture sequence; and (iii) a sequence comprising one or more ribonucleotide base that is complimentary to a first region on a first strand of a second target nucleic acid; and a capture probe comprising, from 5' to 3', (i) a sequence region identical to the sequence region from the cleavable probe and comprising at least one un-labeled non-natural nucleotide identical to the at least one non-natural nucleotide from the cleavable probe; and (ii) a sequence complimentary to capture sequence of the cleavable probe; (b) contacting the cleavable probe with an endoribonuclease, thereby cleaving probe that is hybridized with the second target nucleic acid to form a truncated cleavable probe; (c) allowing the truncated cleavable probe to hybridize with the capture probe; (d) extending the truncated cleavable probe in the presence of a quencher-labeled non-natural nucleotide that is capable of base-pairing with the at least un-labeled one non-natural nucleotide in the capture probe to form an extended cleavable probe; (e) allowing the extended cleavable probe to hybridize to itself to form a hairpin probe; and (f) detecting the second target nucleic acid by detecting a change in signal from the label on the cleavable probe and the hairpin probe.

In certain aspects, the cleavable probe may comprise a sequence comprising 1 to 5 ribonucleotide bases that is complimentary to a first region on a first strand of the target nucleic acid sequence. In some aspects, the cleavable probe may comprise a sequence comprising 3 to 5 ribonucleotide bases that is complimentary to a first region on a first strand of the target nucleic acid sequence.

In yet a further aspect, the method is a multiplex method and comprises (a) contacting the sample with a third, fourth, fifth or sixth set of probes, said set of probes comprising a cleavable probe comprising, from 5' to 3', (i) a sequence region comprising at least a one non-natural nucleotide labeled with a first member of a reporter-quencher pair; (ii) a capture sequence; and (iii) a sequence comprising one or more ribonucleotide base that is complimentary to a first region on a first strand of a third, fourth, fifth or sixth target nucleic acid; and a capture probe comprising, from 5' to 3', (i) a sequence region identical to the sequence region from the cleavable probe and comprising at least one un-labeled non-natural nucleotide identical to the at least one non-natural nucleotide from the cleavable probe; and (ii) a sequence complimentary to capture sequence of the cleavable probe; (b) contacting the cleavable probe with an endoribonuclease, thereby cleaving probe that is hybridized with the third, fourth, fifth or sixth target nucleic acid to form a truncated cleavable probe; (c) allowing the truncated cleavable probe to hybridize with the capture probe; (d) extending the truncated cleavable probe in the presence of a quencher-labeled non-natural nucleotide that is capable of base-pairing with the at least un-labeled one non-natural nucleotide in the capture probe to form an extended cleavable probe; (e) allowing the extended cleavable probe to hybridize to itself to form a hairpin probe; and (f) detecting the third, fourth, fifth or sixth target nucleic acid by detecting a change in signal from the label on the cleavable probe and the hairpin probe. For example, detecting the presence of the first and/or second target nucleic acid may be performed sequentially or essentially simultaneously. In still a further aspect, the first and second set of probes may comprise distinguishable reporters. In another aspect, the first and second set of probes may comprise the same reporter and, in some cases, the hairpin probes formed by the first and second probes may comprise distinguishable melt points (e.g., melt points that differ by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30° C. from one another, or any range derivable therein). In one aspect, the hairpin probes formed by the first, second, third, fourth, fifth, and/or sixth set of probes each may comprise a distinguishable label or a distinguishable melt point. Thus, in some further aspects, a multiplex method according to the embodiments can comprise the use of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more distinct set of probes wherein each probe comprises either (1) a distinguishable melt point or (2) a distinguishable label, such that the signal from each distinct probe may be individually discerned.

In certain aspects, the second sequence region of the cleavable probe may comprise one or more non-natural bases. In certain aspects, after an endoribonuclease cleavage, the truncated cleavable probe and the target nucleic acid may have a melt point of less than 55° C.

In certain aspects, the first member of a reporter-quencher pair may be a reporter, such as, for example, a fluorophore. In some aspects, the change in the signal may be a decrease in a fluorescent signal.

In certain aspects, detecting a change in signal from the label may comprise detecting a change in signal from a reporter as the temperature of the sample is changed. In some aspects, detecting a change in signal from the reporter may comprise detecting a change in signal from the reporter as the temperature of the sample is increased above the melt point of hairpin probe.

In certain aspects, the cleavable probe and/or the capture probe may be attached to a solid support.

In a further embodiment, a composition is provided comprising a first set of probes, said set of probes comprising a cleavable probe comprising, from 5' to 3', (i) a sequence region comprising at least a one non-natural nucleotide labeled with a first member of a reporter-quencher pair; (ii) a capture sequence; and (iii) a sequence comprising one or more ribonucleotide base that is complimentary to a first region on a first strand of the target nucleic acid; and a capture probe comprising, from 5' to 3', (i) a sequence region identical to the sequence region from the cleavable probe and comprising at least one un-labeled non-natural nucleotide identical to the at least one non-natural nucleotide from the cleavable probe; and (ii) a sequence complimentary to capture sequence of the cleavable probe. In certain aspects, the comprising may further comprise a reporter-labeled or quencher-labeled non-natural nucleotide. In certain aspects, the composition may comprise a polymerase, a reference probe or free nucleotides.

In a further aspect, the composition may further comprise a second set of probes comprising a cleavable probe comprising, from 5' to 3', (i) a sequence region comprising at least a one non-natural nucleotide labeled with a first member of a reporter-quencher pair; (ii) a capture sequence; and (iii) a sequence comprising one or more ribonucleotide base that is complimentary to a first region on a first strand of a second target nucleic acid; and a capture probe comprising, from 5' to 3', (i) a sequence region identical to the sequence region from the cleavable probe and comprising at least one un-labeled non-natural nucleotide identical to the at least one non-natural nucleotide from the cleavable probe; and (ii) a sequence complimentary to capture sequence of the cleavable probe. In certain aspects, the first and second set of probes may comprise distinguishable reporters and/or form hairpins having distinguishable melt points. In some aspects, the composition comprises 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more sets of probes.

In a further embodiment, a kit is provided comprising (a) a first set of probes, said set of probes comprising a cleavable probe comprising, from 5' to 3', (i) a sequence region comprising at least a one non-natural nucleotide labeled with a first member of a reporter-quencher pair; and (iii) a sequence comprising one or more ribonucleotide base that is complimentary to a first region on a first strand of the target nucleic acid; and a capture probe comprising, from 5' to 3', (i) a sequence region identical to the sequence region from the cleavable probe and comprising at least one un-labeled non-natural nucleotide identical to the at least one non-natural nucleotide from the cleavable probe; and (ii) a sequence complimentary to capture sequence of the cleavable probe; and (b) a reporter-labeled non-natural nucleotide; a quencher-labeled non-natural nucleotide; or an endoribonuclease enzyme. In a further aspect, the kit comprises at least four sets of probes. In certain aspects, the sets of probes may comprise distinguishable reporters or form hairpins with distinguishable melt points. In some aspects, the kit may further comprise a polymerase, a reference probe, free nucleotides, a reference sample, or instructions for use of the kit.

In yet a further embodiment, a method is provided for detecting the presence of a target nucleic acid comprising: (a) contacting the sample with a first set of probes, said set of probes comprising a cleavable probe comprising, from 5' to 3', (i) a sequence region comprising at least a one non-natural nucleotide labeled with a first member of a reporter-quencher pair; (ii) a capture sequence; and (iii) a sequence comprising one or more ribonucleotide base that is complimentary to a first region on a first strand of the target nucleic acid; and a capture probe comprising, from 5' to 3', (i) a sequence region identical to a part of the sequence region from the cleavable probe and (ii) a sequence complimentary to capture sequence of the cleavable probe; (b) contacting the cleavable probe with an endoribonuclease, thereby cleaving the cleavable probe that is hybridized with target nucleic acid to form a truncated cleavable probe; (c) allowing the truncated cleavable probe to hybridize with the capture probe; (d) extending the truncated cleavable probe to form an extended probe; (e) allowing the extended cleavable probe to hybridize to itself to form a hairpin probe; (f) further extending the hairpin probe in the presence of a non-natural nucleotide labeled with a second member of a reporter-quencher pair that is capable of base-pairing with the at least one labeled non-natural nucleotide at the 5' of the cleavable probe; and (g) detecting the target nucleic acid by detecting a change in signal from the label on the cleavable probe and the hairpin probe.

In a further aspect, the method may comprise (a) contacting the sample with a second set of probes, said set of probes comprising a cleavable probe comprising, from 5' to 3', (i) a sequence region comprising at least a one non-natural nucleotide labeled with a first member of a reporter-quencher pair; (ii) a capture sequence; and (iii) a sequence comprising one or more ribonucleotide base that is complimentary to a first region on a first strand of a second target nucleic acid; and a capture probe comprising, from 5' to 3', (i) a sequence region identical to a part of the sequence region from the cleavable probe and (ii) a sequence complimentary to capture sequence of the cleavable probe; (b) contacting the cleavable probe with an endoribonuclease, thereby cleaving the cleavable probe that is hybridized with target nucleic acid to form a truncated cleavable probe; (c) allowing the truncated cleavable probe to hybridize with the capture probe; (d) extending the truncated cleavable probe to form an extended probe; (e) allowing the extended cleavable probe to hybridize to itself to form a hairpin probe; (f) further extending the hairpin probe in the presence of a non-natural nucleotide labeled with a second member of a reporter-quencher pair that is capable of base-pairing with the at least one labeled non-natural nucleotide at the 5' of the cleavable probe; and (g) detecting the second target nucleic acid by detecting a change in signal from the label on the cleavable probe and the hairpin probe.

In certain aspects, the cleavable probe may comprise a sequence comprising 1 to 5 ribonucleotide bases that is complimentary to a first region on a first strand of the target nucleic acid sequence. In some aspects, the cleavable probe may comprise a sequence comprising 3 to 5 ribonucleotide bases that is complimentary to a first region on a first strand of the target nucleic acid sequence.

In yet a further aspect, the method is a multiplex method and comprises (a) contacting the sample with a third, fourth, fifth or sixth set of probes, said set of probes comprising a cleavable probe comprising, from 5' to 3', (i) a sequence region comprising at least a one non-natural nucleotide labeled with a first member of a reporter-quencher pair; (ii) a capture sequence; and (iii) a sequence comprising one or more ribonucleotide base that is complimentary to a first region on a first strand of a third, fourth, fifth or sixth target nucleic acid; and a capture probe comprising, from 5' to 3', (i) a sequence region identical to a part of the sequence region from the cleavable probe and (ii) a sequence complimentary to capture sequence of the cleavable probe; (b) contacting the cleavable probe with an endoribonuclease, thereby cleaving the cleavable probe that is hybridized with target nucleic acid to form a truncated cleavable probe; (c) allowing the truncated cleavable probe to hybridize with the capture probe; (d) extending the truncated cleavable probe to form an extended probe; (e) allowing the extended cleavable probe to hybridize to itself to form a hairpin probe; (f) further extending the hairpin probe in the presence of a non-natural nucleotide labeled with a second member of a reporter-quencher pair that is capable of base-pairing with the at least one labeled non-natural nucleotide at the 5' of the cleavable probe; and (g) detecting the third, fourth, fifth or sixth target nucleic acid by detecting a change in signal from the label on the cleavable probe and the hairpin probe. For example, detecting the presence of the first, second and/or further target nucleic acid may be performed sequentially or essentially simultaneously. In still a further aspect, first, second and/or further set of probes may comprise distinguishable reporters. In another aspect, first, second and/or further set of probes may comprise the same reporter and, in some cases, the hairpin probes formed by the first and second probes may comprise distinguishable melt points (e.g., melt points that differ by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30° C. from one another, or any range derivable therein). In one aspect, the hairpin probes formed by the first, second, third, fourth, fifth, and/or sixth set of probes each may comprise a distinguishable label or a distinguishable melt point. Thus, in some further aspects, a multiplex method according to the embodiments can comprise the use of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more distinct set of probes wherein each probe comprises either (1) a distinguishable melt point or (2) a distinguishable label, such that the signal from each distinct probe may be individually discerned.

In certain aspects, the second sequence region of the cleavable probe may comprise one or more non-natural bases. In certain aspects, after an endoribonuclease cleavage, the truncated cleavable probe and the target nucleic acid may have a melt point of less than 55° C.

In certain aspects, the first member of a reporter-quencher pair may be a reporter, such as, for example, a fluorophore. In some aspects, the change in the signal may be a decrease in a fluorescent signal.

In certain aspects, detecting a change in signal from the label may comprise detecting a change in signal from a reporter as the temperature of the sample is changed. In some aspects, detecting a change in signal from the reporter may comprise detecting a change in signal from the reporter as the temperature of the sample is increased above the melt point of hairpin probe.

In certain aspects, the cleavable probe and/or the capture probe may be attached to a solid support.

In a further embodiment, a composition is provided comprising a first set of probes, said set of probes comprising a cleavable probe comprising, from 5' to 3', (i) a sequence region comprising at least a one non-natural nucleotide labeled with a first member of a reporter-quencher pair; (ii) a capture sequence; and (iii) a sequence comprising one or more ribonucleotide base that is complimentary to a first region on a first strand of the target nucleic acid; and a capture probe comprising, from 5' to 3', (i) a sequence region identical to a part of the sequence region from the cleavable probe and (ii) a sequence complimentary to capture sequence of the cleavable probe. In certain aspects, the comprising may further comprise a reporter-labeled or quencher-labeled non-natural nucleotide. In certain aspects, the composition may comprise a polymerase, a reference probe or free nucleotides.

In a further aspect, the composition may further comprise a second set of probes, said set of probes comprising a cleavable probe comprising, from 5' to 3', (i) a sequence region comprising at least a one non-natural nucleotide labeled with a first member of a reporter-quencher pair; (ii) a capture sequence; and (iii) a sequence comprising one or more ribonucleotide base that is complimentary to a first region on a first strand of a second target nucleic acid; and a capture probe comprising, from 5' to 3', (i) a sequence region identical to a part of the sequence region from the cleavable probe and (ii) a sequence complimentary to capture sequence of the cleavable probe. In certain aspects, the first and second set of probes may comprise distinguishable reporters and/or form hairpins having distinguishable melt points. In some aspects, the composition comprises 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more sets of probes.

In a further embodiment, a kit is provided comprising (a) a first set of probes, said set of probes comprising a cleavable probe comprising, from 5' to 3', (i) a sequence region comprising at least a one non-natural nucleotide labeled with a first member of a reporter-quencher pair; (ii) a capture sequence; and (iii) a sequence comprising one or more ribonucleotide base that is complimentary to a first region on a first strand of the target nucleic acid; and a capture probe comprising, from 5' to 3', (i) a sequence region identical to a part of the sequence region from the cleavable probe and (ii) a sequence complimentary to capture sequence of the cleavable probe; and (b) a reporter-labeled non-natural nucleotide; a quencher-labeled non-natural nucleotide; or an endoribonuclease enzyme. In a further aspect, the kit comprises at least four sets of probes. In certain aspects, the sets of probes may comprise distinguishable reporters or form hairpins with distinguishable melt points. In some aspects, the kit may further comprise a polymerase, a reference probe, free nucleotides, a reference sample, or instructions for use of the kit.

In another embodiment, a method is provided for detecting the presence of a target nucleic acid comprising: (a) contacting the sample with a first cleavable probe, said probe comprising, from 5' to 3', (i) a first sequence region comprising at least one non-natural nucleotide labeled with a first member of a reporter-quencher pair; (ii) a second sequence region; (iii) a sequence that is the reverse complement of the second sequence region; and (iv) a sequence that is complimentary to a first region on a first strand of the target nucleic acid; (b) hybridizing the cleavable probe and an upstream primer to the target nucleic acid, and performing extension using a polymerase possessing 5' nuclease activity; (c) extending the nucleic acid sequence until contacting the cleavable hairpin probe with a polymerase possessing nuclease activity, thereby cleaving the probe that is hybridized with target nucleic acid to form a truncated cleavable probe; (d) allowing the truncated cleavable probe to hybridize to itself to form a hairpin probe; (e) extending the hairpin probe in the presence of a non-natural nucleotide labeled with a second member of a reporter-quencher pair that is capable of base-pairing with the at least one non-natural nucleotide of the first sequence region; and (f) detecting the target nucleic acid by detecting a change in signal from the label on the hairpin probe. In certain aspects, a portion of the sequence that is the reverse complement of the second sequence region (iii) may be complimentary to a first region on a first strand of the target nucleic acid. In certain embodiments, the method may further comprise performing melt analysis on the hairpin probe.

In another embodiment, a method is provided for detecting the presence of a target nucleic acid comprising: (a) contacting the sample with a first cleavable hairpin probe, said probe comprising, from 5' to 3', (i) a first sequence region labeled with a reporter-quencher pair; (ii) a second sequence region; (iii) a sequence that is the reverse complement of the second sequence region; and (iv) a sequence that is complimentary to a first region on a first strand of the target nucleic acid; (b) hybridizing the cleavable probe and an upstream primer to the target nucleic acid, and performing extension using a polymerase possessing 5' nuclease activity; (c) extending the nucleic acid sequence until contacting the cleavable hairpin probe with a polymerase possessing nuclease activity, thereby cleaving the probe that is hybridized with target nucleic acid to form a truncated cleavable probe; (d) allowing the truncated probe to hybridize to itself to form a cleaved hairpin probe; (e) extending the cleaved hairpin probe onto itself such that the flurophore and quencher are physically separated; (f) detecting the target nucleic acid by detecting a change in signal from the extended hairpin probe.

Certain aspects of the embodiments concern the use of at least one non-natural nucleotide. In some aspects, the non-natural nucleotide is an isobase, such as iso-guanine (isoG) or iso-cytosine (isoC). In this aspect, the quencher-labeled non-natural nucleotide is a cognate isoC (or isoG). In still further aspects, at least one of the first and/or second primers comprises at least one non-natural nucleotide in the target-specific sequence. For example, in some aspects, the non-natural nucleotide in the target-specific sequence regulates sequence-specific annealing thereby enhancing primer-template hybridization for sequence-specific amplification of nucleotides (see, e.g., PCT Publn. WO/2011/050278, incorporated herein by reference).

The cleavage and extension of the cleavable probes as disclosed herein may be performed under isothermal conditions in which the cleavable probes are cleaved and extended while reaction conditions are maintained at a substantially constant temperature. Isothermal amplification of signal may be achieved because both fragments of a cleaved probe possess a lower melting temperature than the probe to target before cleavage. This causes the two fragments to disassociate from the target, allowing another probe to hybridize and cleave. This process repeats itself allowing multiple probes to cleave and extend from a single target at a constant temperature. This feature is unique compared to other methods related to closed tube multiplexed detection by melt analysis, which rely on 5'-nuclease activity to obtain unique melt signatures, which cannot amplify the signal of targets or amplicons isothermally. Alternatively, the cleavage and extension of the cleavable probes as disclosed herein may be performed under non-isothermal conditions, such as under the cycling temperature conditions of PCR.

In some aspects, a method of the embodiments may further comprise performing an amplification step to amplify a target sequence. The cleavage and extension of the cleavable probes may be performed during or subsequent to the amplification process. For example, the amplification can be isothermal amplification or one or more polymerase chain reaction cycles. Isothermal amplification techniques include, for example, strand displacement amplification (SDA), loop-mediated amplification (LAMP), rolling circle amplification (RCA), and helicase-dependent amplification (HAD) (see, e.g., Yan et al., 2014). In some aspects, detecting the change in signal from the label comprises detecting the signal before, during, or after performing the isothermal amplification or the multiple polymerase chain reaction cycles. In another aspect, detecting the change in signal from the label comprises detecting the signal only after performing the isothermal amplification or the multiple polymerase chain reaction cycles. In this aspect, the method may further comprise comparing the detected signal from the label to a predetermined ratio of the signal of the label to a reference signal from a label on a non-hybridizing probe.

In some aspects, a method of the embodiments may further comprise quantifying the amount of the target nucleic acid in the sample. For example, quantifying the amount of the target nucleic acid in the sample may comprise: using digital PCR; using a standard curve; determining a relative amount of the nucleic acid target; using end-point quantitation; or determining an amount of the nucleic acid target by relating the PCR cycle number at which the signal is detectable over background to the amount of target present.

In various aspects of the present methods, detecting a change in signal from the reporter may comprise detecting the change (or rate of change) in signal, such as unquenching of a signal as the temperature of the sample is changed. In one aspect, the temperature of the sample may be increased above (or decreased below) the melt point of the hairpin of one more of the primers in the sample. In the case where two or more primer sets are present, changing the temperature of a sample may comprise increasing the temperature of the sample from a temperature that is below the melt point of the hairpins of both of the first primers in the first and second set of primers to a temperature that is above the melt point of both of the hairpins.

In various aspects, the probes of the embodiments may comprise the same reporter and comprise hairpins with distinguishable melt points (e.g., melt points that differ by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30° C. from one another, or any range derivable therein).

In further various aspects, a multiplex method according to the embodiments can comprise the use of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more distinct probe sets wherein each probe or probe set comprises either (1) a hairpin with a distinguishable melt point or (2) a distinguishable reporter, such that the signal from each distinct probe or probe set may be individually discerned.

In a further embodiment, a kit is provided comprising one or more probes or probe sets of the embodiments. In a further aspect, the kit further comprises a polymerase with exonuclease activity, an endoribonuclease (e.g., an RNase H), a reference probe, free nucleotides, free non-natural nucleotide, a reference sample and/or instructions for use of the kit.

As used herein a solid support may be beads with magnetic properties and/or beads with a density that allows them to rest upon a two dimensional surface in solution. The particles may in one way or another rest upon a two dimensional surface by magnetic, gravitational, or ionic forces, or by chemical bonding, or by any other means known to those skilled in the art. Particles may consist of glass, polystyrene, latex, metal, quantum dot, polymers, silica, metal oxides, ceramics, or any other substance suitable for binding to nucleic acids, or chemicals or proteins which can then attach to nucleic acids. The particles may be rod shaped or spherical or disc shaped, or comprise any other shape. The particles may also be distinguishable by their shape or size or physical location. The particles may be spectrally distinct by virtue of having a composition containing dyes or ratios or concentrations of one or more dyes or fluorochromes, or may be distinguishable by barcode or holographic images or other imprinted forms of particle coding. Where the particles are magnetic particles, they may be attracted to the surface of the chamber by application of a magnetic field. Likewise, magnetic particles may be dispersed from the surface of the chamber by removal of the magnetic field. The magnetic particles are preferably paramagnetic or superparamagnetic. Paramagnetic and superparamagnetic particles have negligible magnetism in the absence of a magnetic field, but application of a magnetic field induces alignment of the magnetic domains in the particles, resulting in attraction of the particles to the field source. When the field is removed, the magnetic domains return to a random orientation so there is no interparticle magnetic attraction or repulsion. In the case of superparamagnetism, this return to random orientation of the domains is nearly instantaneous, while paramagnetic materials will retain domain alignment for some period of time after removal of the magnetic field. Where the particles have a sufficient density they may be attracted to the bottom surface of the chamber by gravity, and dispersed from the bottom surface of the chamber by agitation of the chamber, such as by vortexing, sonication, or fluidic movement. Agitation of the chamber may also be used to further assist in dispersing particles in methods and systems in which the particles were attracted to a surface of the chamber by other forces, such as magnetic or ionic forces, or suction forces, or vacuum filtration, or affinity, or hydrophilicity or hydrophobicity, or any combination thereof.

A reporter or labeling agent, is a molecule that facilitates the detection of a molecule (e.g., a nucleic acid sequence) to which it is attached. Numerous reporter molecules that may be used to label nucleic acids are known. Direct reporter molecules include fluorophores, chromophores, and radiophores. Non-limiting examples of fluorophores include, a red fluorescent squarine dye such as 2,4-Bis[1,3,3-trimethyl-2-indolinylidenemethyl]cyclobutenediylium-1,3-dio-xolate, an infrared dye such as 2,4 Bis[3,3-dimethyl-2-(1H-benz[e] indolinylidenemethyl)]cyclobutenediylium-1,-3-dioxolate, or an orange fluorescent squarine dye such as 2,4-Bis[3,5-dimethyl-2-pyrrolyl]cyclobutenediylium-1,3-diololate. Additional non-limiting examples of fluorophores include quantum dots, Alexa Fluor™ dyes, AMCA, BODIPY™ 630/650, BODIPY™ 650/665, BODIPY™-FL, BODIPY™-R6G, BODIPY™-TMR, BODIPY™-TRX, Cascade Blue™, CyDye™, including but not limited to Cy2™, Cy3™, and Cy5™, a DNA intercalating dye, 6-FAM™, Fluorescein, HEX™, 6-JOE, Oregon Green™ 488, Oregon Green™ 500, Oregon Green™ 514, Pacific Blue™, REG, phycobilliproteins including, but not limited to, phycoerythrin and allophycocyanin, Rhodamine Green™, Rhodamine Red™, ROX™, TAMRA™, TET™, Tetramethylrhodamine, or Texas Red™. A signal amplification reagent, such as tyramide (PerkinElmer), may be used to enhance the fluorescence signal. Indirect reporter molecules include biotin, which must be bound to another molecule such as streptavidin-phycoerythrin for detection. Pairs of labels, such as fluorescence resonance energy transfer pairs or dye-quencher pairs, may also be employed.

Labeled amplification products may be labeled directly or indirectly. Direct labeling may be achieved by, for example, using labeled primers, using labeled dNTPs, using labeled nucleic acid intercalating agents, or combinations of the above. Indirect labeling may be achieved by, for example, hybridizing a labeled probe to the amplification product.

The methods disclosed herein may further comprise quantifying the initial amount of the nucleic acid target(s) in the sample. The quantification may comprise, for example, determining the relative concentrations of DNA present during the exponential phase of the real-time PCR by plotting fluorescence against cycle number on a logarithmic scale. The amounts of DNA may then be determined by comparing the results to a standard curve produced by real-time PCR of serial dilutions of a known amount of DNA. Additionally, real-time PCR may be combined with reverse transcription polymerase chain reaction to quantify RNAs in a sample, including low abundance RNAs. Alternatively, quantification may be accomplished by digital PCR.

The target nucleic acid sequence may be any sequence of interest. The sample containing the target nucleic acid sequence may be any sample that contains nucleic acids. In certain aspects of the invention the sample is, for example, a subject who is being screened for the presence or absence of one or more genetic mutations or polymorphisms. In another aspect of the invention the sample may be from a subject who is being tested for the presence or absence of a pathogen. Where the sample is obtained from a subject, it may be obtained by methods known to those in the art such as aspiration, biopsy, swabbing, venipuncture, spinal tap, fecal sample, or urine sample. In some aspects of the invention, the sample is an environmental sample such as a water, soil, or air sample. In other aspects of the invention, the sample is from a plant, bacteria, virus, fungi, protozoan, or metazoan.

Each amplification cycle has three phases: a denaturing phase, a primer annealing phase, and a primer extension phase. The amplification cycle can be repeated until the desired amount of amplification product is produced. Typically, the amplification cycle is repeated between about 10 to 40 times. For real-time PCR, detection of the amplification products will typically be done after each amplification cycle. Although in certain aspects of the invention, detection of the amplification products may be done after every second, third, fourth, or fifth amplification cycle. Detection may also be done such that as few as 2 or more amplification cycles are analyzed or detected. The amplification cycle may be performed in the same chamber in which the detection of the amplification occurs, in which case this chamber would need to comprise a heating element so the temperature in the chamber can be adjusted for the denaturing phase, primer annealing phase, and a primer extension phase of the amplification cycle. The heating element would typically be under the control of a processor. The amplification cycle may, however, be performed in a different chamber from the chamber in which detection of the amplification occurs, in which case the "amplification" chamber would need to comprise a heating element but the "detection" or "imaging" chamber would not be required to have a heating element. Where amplification and detection occur in separate chambers, the fluid in which the amplification reaction occurs may be transferred between the chambers by, for example, a pump or piston. The pump or piston may be under the control of a processor. Alternatively, the fluid may be transferred between the chambers manually using, for example, a pipette.

Amplification may be performed in a reaction mixture that includes at least one non-natural nucleotide having a non-natural nucleotide. The at least one non-natural nucleotide of the reaction mixture may base pair with the at least one non-natural nucleotide present in the primer of the first and/or second primer set. Optionally, the non-natural nucleotide is coupled to a label which may include fluorophores and quenchers. The quencher may quench a fluorophore present in the primer of the first and/or second primer set.

Detecting may include amplifying one or more polynucleotides of the population. For example, detecting may include amplifying one or more polynucleotides of the population in the presence of at least one non-natural nucleotide. The non-natural nucleotide may have a non-natural nucleotide (e.g., isoC and isoG), which, optionally, is capable of base-pairing with the non-natural nucleotide of the mixture of oligonucleotides (e.g., a non-natural nucleotide present in the degenerate oligonucleotides). The non-natural nucleotide may be coupled to a label. Suitable labels include fluorophores and quenchers.

The method may be used to detect the target continuously during amplification or in real-time. The method may be used quantitatively.

Certain aspects of the embodiments concern endoribonuclease enzymes and use of such enzymes to specifically cleave probes having a ribonucleotide (RNA) position when the probe is hybridized to a DNA target sequence. In some aspects, the endoribonuclease is an RNAse H, such as RNase HII. In certain specific aspects, the endoribonuclease is a thermostable enzyme or a thermophilic, hotstart enzyme (e.g., a thermostable RNase HII enzyme and a thermophilic, hotstart RNaseHII enzyme).

Amplification may be performed in the presence of one or more non-natural nucleotides and/or in the presence of at least one quencher coupled to a non-natural nucleotide. In some embodiments, the non-natural nucleotide coupled to the at least one quencher may be isoCTP or isoGTP.

In some methods, the first and second labels may be different. In some methods the first and second quencher may be different and may be capable of quenching two different fluorophores. In other methods, the first and second quenchers may be the same and may be capable of quenching two different fluorophores.

The methods described herein may include determining a melting temperature for an amplicon (e.g., amplified nucleic acid of at least one of amplified nucleic acid of HIV and amplified control nucleic acid). The methods may include determining a melting temperature for a nucleic acid complex that includes a labeled probe hybridized to a target nucleic acid (which may include amplified target nucleic acid). The melting temperature may be determined by exposing the amplicon or nucleic acid complex to a gradient of temperatures and observing a signal from a label. Optionally, the melting temperature may be determined by (a) reacting an amplicon with an intercalating agent at a gradient of temperatures and (b) observing a detectable signal from the intercalating agent. The melting temperature of a nucleic acid complex may be determined by (1) hybridizing a probe to a target nucleic acid to form a nucleic acid complex, where at least one of the probe and the target nucleic acid includes a label; (2) exposing the nucleic acid complex to a gradient of temperatures; and (3) observing a signal from the label.

The methods may be performed in any suitable reaction chamber under any suitable conditions. For example, the methods may be performed in a reaction chamber without opening the reaction chamber. The reaction chamber may be part of an array of reaction chambers. In some embodiments, the steps of the methods may be performed separately in different reaction chambers.

The methods disclosed herein may be performed in droplets. Likewise, the compositions disclosed herein may be disposed within droplets. For example, the cleavable probes disclosed herein may be divided into many separate reactions for PCR or isothermal amplification using droplets. Thus, in certain embodiments the methods disclosed herein are compartmentalized in droplets to perform quantitative digital PCR reactions, or other quanitative digital amplification reactions. As described in Vogelstein et al., 1999, at pgs. 9236-9241, digital PCR methods may be helpful for distributing the target nucleic acid such that the vast majority of reactions contain either one or zero target nucleic acid molecules. At certain dilutions the number of amplification positive reactions is equal to the number of template molecules originally present.

In some embodiments, the methods may be capable of detecting no more than about 100 copies of the target nucleic acid in a sample (e.g., in a sample having a volume of about 25 microliters). In other embodiments, the methods may be capable of detecting no more than about 500 copies, 1000 copies, 5000 copies, or 10,000 copies in a sample (e.g., in a sample having a volume of about 25 microliters).

In other embodiments, the methods may be capable of detecting no more than about 100 copies of target nucleic acid in a sample (e.g., in a sample having a volume of about 25 microliters) using real-time detection in no more than about 150 cycles of the PCR, no more than about 100 cycles, no more than about 90 cycles, no more than about 80 cycles, no more than about 70 cycles, no more than about 60 cycles, no more than about 50 cycles, no more than about 40 cycles, or no more than about 30 cycles of the PCR.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-B—A non-limiting exemplary schematic showing a probe system of the embodiments. FIG. 1A, The cleavable probe comprises a reporter-labeled isoG nucleotide ("isoG*") at its 5' end, a first sequence region ("Tag A"), a second sequence region ("Tag B"), a loop sequence, a sequence region that is the reverse compliment of Tag B ("Tag B complement"); and a sequence complementary to the target amplicon (indicated as "A"). The cleavable probe also comprises one or more ribonucleotides (indicated by the solid square) in the "A" sequence and may comprise a modification that blocks extension on the 3' end (indicated as "P"). In the presence of a target amplicon the cleavable probe hybridizes to the amplicon and is cleaved at the ribonucleotide position by RNase H. Following cleavage, the probe can hybridize to itself via the Tag B and Tag B complement sequences to form a hairpin. Extension of the probe will synthesize sequences complementary to the Tag A sequences and will incorporate a quencher labeled isoC ("isoC$^Q$"). The resulting hairpin probe quenches the fluorescence of the labeled isoG. FIG. 1B, The probes can be designed to have unique melt temperatures ($T_m$), such as by adjusting the sequence and length of the sequence regions. Thus, a melt analysis can be performed to differentiation probes having different melt temperatures (and thus unquenching at different temperatures).

FIG. 2—Non-limiting exemplary probe constructs of the embodiments with variable stem, loop, $T_m$ and delta G. The probes were designed as detailed in FIG. 1. The sequences of each probe are shown (SEQ ID NOS: 1-11 as listed from top to bottom). Tag A sequences are in bold and the stem is comprised of 3 segments: sequence specific (B, underlined nucleotides), universal sequence (C, italicized nucleotides) and an extendable universal sequence (A, bold font nucleotides) ending with a fluorophore-labelled isobase.

FIG. 3—Non-limiting exemplary target-specific probe designs of the embodiments (SEQ ID NOS: 12-21 as listed from top to bottom). The three segments of the stem are illustrated as in FIG. 2.

FIG. 4—Graph shows the temperature gradient used to assess the hairpin folding of the constructs shown in FIG. 2.

FIG. 5—Graph shows fluorescence quenching as a function of time for the RTx-5 construct as the annealing temperature is stepped down (see, e.g., FIG. 4). Complete quenching was observed by the 71° C. temperature step.

FIG. 6—Graph shows fluorescence quenching as a function of time for the RTx-10 construct as the annealing temperature is stepped down (see, e.g., FIG. 4). Complete quenching was observed by the 62° C. temperature step.

FIG. 7—Graph shows fluorescence quenching as a function of time for the RTx-11 construct as the annealing temperature is stepped down (see, e.g., FIG. 4). Complete quenching was observed by the 41° C. temperature step.

FIGS. 8A-8C—Graphs show amplification (upper panels) and melt curves (lower panels) obtained from constructs RTx-1 and RTx-2 at 50° C., 62° C. and 68° C.

FIGS. 9A-9C—Graphs show amplification (upper panels) and melt curves (lower panels) obtained from constructs RTx-7 and RTx-8 at 50° C., 62° C. and 68° C.

FIGS. 10A-10C—Graphs show amplification (upper panels) and melt curves (lower panels) obtained from constructs RTx-9, RTx-10, and RTx-11 at 50° C., 62° C. and 68° C.

FIGS. 11A-11D—Graphs show amplification (upper panels) and melt (lower panels) curves of full length probes FL-RTx-2-20 (A), FL-RTx-2-12AT1 (B), FL-RTx-2c (C), and FL-RTx-2-12-AT-4 (D). Controls: water=thin solid line, clinical negative specimen=dashed line. The test probe results are shown in thick solid lines.

DESCRIPTION OF ILLUSTRATIVE EMBODIMENTS

Figure 1A:
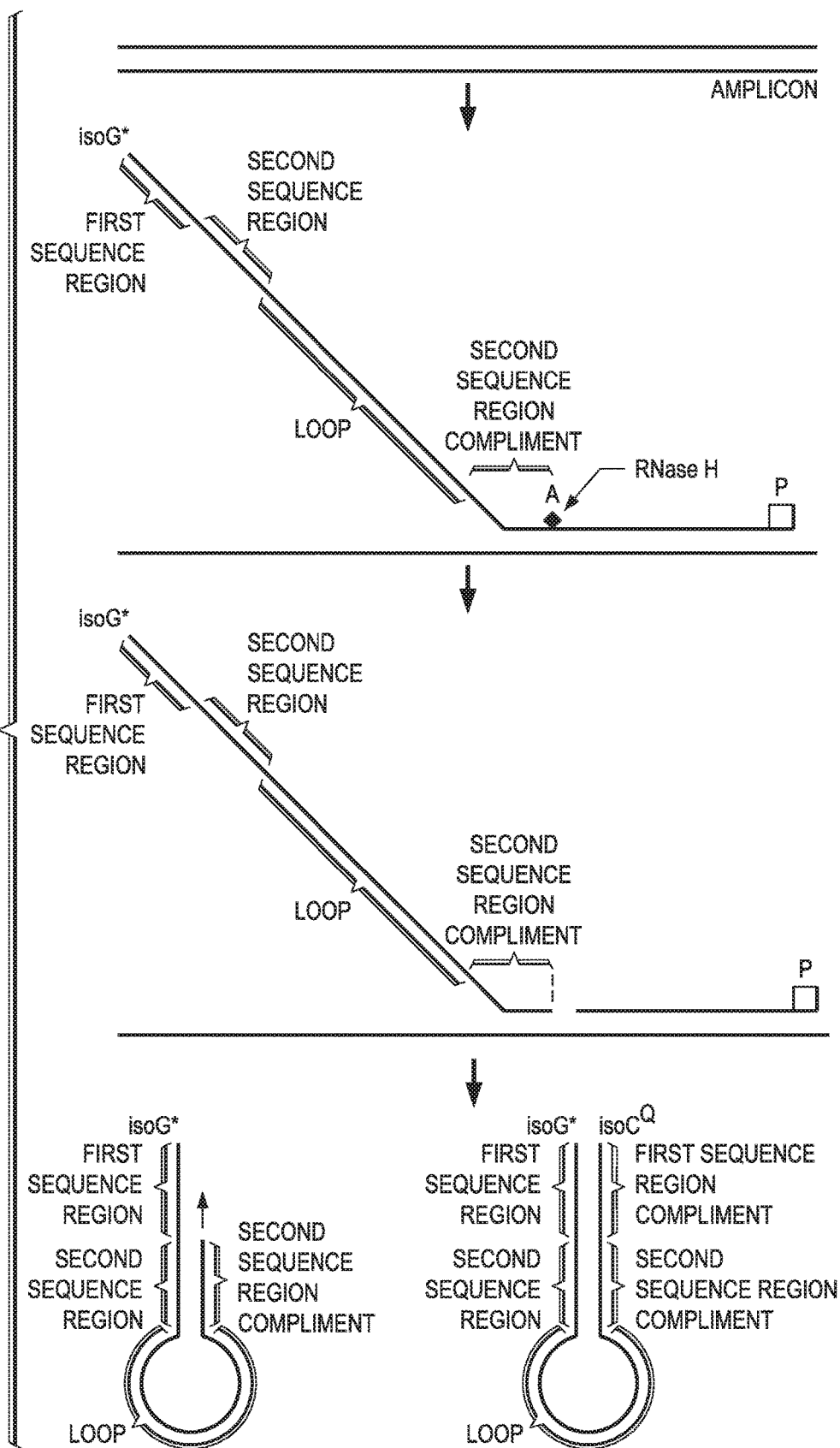

Melt analysis assays utilize melt or anneal peaks to discriminate amplicon identity, but these melt peaks are not easily distinguishable in amplicons that melt near the same temperature and are subject to the natural sequence composition of the target. By creating hairpin sequences with unique melt profiles, multiplexing can be achieved in a single color channel, thus allowing even more multiplexing with multiple color channels.

Disclosed are methods and kits for detecting nucleic acids in a sample. Typically, the methods include detecting signals, such as a signal emitted from a fluorophore. Also disclosed are oligonucleotides, especially probes, which may be used for the detection of target nucleic acids. In particular methods of the embodiments employ an extendable probe to facilitate multiplexing by generation of multiple melt curves per fluorophore. In some cases, the probe is comprised of a hairpin structure with a sequence-specific tail at the 3'-end and an extendable universal sequence at the 5' end terminating in a fluorophore labelled isobase. Unlike other probe based chemistries, the sequence specific segment is used for target identification and the release of the hairpin for detection. In some aspects, the release of the hairpin is based on cleavage of RNA/DNA hybrid created as the sequences specific tail of the probe hybridizes to the template. Thus, none or only a few (e.g., 3-4) bases of the sequence-specific segment are incorporated into the hairpin structure, which is mainly comprised of target independent sequences. Varying the length of the extendable segment of the hairpin gives rise to hairpins with various sizes allowing for generation of multiple melt curves per fluorophore.

I. Definitions

As used herein "nucleic acid" means either DNA or RNA, single-stranded or double-stranded, and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, methylations, and unusual base-pairing combinations, such as the isobases. Accordingly, the nucleic acids described herein include not only the standard bases adenine (A), cytosine (C), guanine (G), thymine (T), and uracil (U) but also non-standard or non-natural nucleotides. Non-standard or non-natural nucleotides, which form hydrogen-bonding base pairs, are described, for example, in U.S. Pat. Nos. 5,432,272, 5,965,364, 6,001,983, 6,037,120, and 6,140,496, all of which are incorporated herein by reference. By "non-standard nucleotide" or "non-natural nucleotide" it is meant a base other than A, G, C, T, or U that is susceptible to incorporation into an oligonucleotide and that is capable of base-pairing by hydrogen bonding, or by hydrophobic, entropic, or van der Waals interactions, with a complementary non-standard or non-natural nucleotide to form a base pair. Some examples include the base pair combinations of iso-C/iso-G, K/X, K/P, H/J, and M/N, as illustrated in U.S. Pat. No. 6,037,120, incorporated herein by reference.

The hydrogen bonding of these non-standard or non-natural nucleotide pairs is similar to those of the natural bases where two or three hydrogen bonds are formed between hydrogen bond acceptors and hydrogen bond donors of the pairing non-standard or non-natural nucleotides. One of the differences between the natural bases and these non-standard or non-natural nucleotides is the number and position of hydrogen bond acceptors and hydrogen bond donors. For example, cytosine can be considered a donor/acceptor/acceptor base with guanine being the complementary acceptor/donor/donor base. Iso-C is an acceptor/acceptor/donor base and iso-G is the complementary donor/donor/acceptor base, as illustrated in U.S. Pat. No. 6,037,120, incorporated herein by reference.

Other non-natural nucleotides for use in oligonucleotides include, for example, naphthalene, phenanthrene, and pyrene derivatives as discussed, for example, in Ren, et al., 1996 and McMinn et al., 1999, both of which are incorporated herein by reference. These bases do not utilize hydrogen bonding for stabilization, but instead rely on hydrophobic or van der Waals interactions to form base pairs.

As used herein, the term "sample" is used in its broadest sense. A sample may include a bodily tissue or a bodily fluid including but not limited to blood (or a fraction of blood, such as plasma or serum), lymph, mucus, tears, urine, and saliva. A sample may include an extract from a cell, a chromosome, organelle, or a virus. A sample may comprise DNA (e.g., genomic DNA), RNA (e.g., mRNA), and/or cDNA, any of which may be amplified to provide an amplified nucleic acid. A sample may include nucleic acid in solution or bound to a substrate (e.g., as part of a microarray). A sample may comprise material obtained from an environmental locus (e.g., a body of water, soil, and the like) or material obtained from a fomite (i.e., an inanimate object that serves to transfer pathogens from one host to another).

The term "source of nucleic acid" refers to any sample that contains nucleic acids (RNA or DNA). Particularly preferred sources of target nucleic acids are biological samples including, but not limited to, blood, plasma, serum, saliva, cerebral spinal fluid, pleural fluid, milk, lymph, sputum, and semen.

As used herein, the term "limit of detection" refers to the lowest level or amount of an analyte, such as a nucleic acid, that can be detected and quantified. Limits of detection can be represented as molar values (e.g., 2.0 nM limit of detection), as gram measured values (e.g., 2.0 microgram limit of detection under, for example, specified reaction conditions), copy number (e.g., $1 \times 10^5$ copy number limit of detection), or other representations known in the art.

As used herein the term "isolated" in reference to a nucleic acid molecule refers to a nucleic acid molecule that is separated from the organisms and biological materials (e.g., blood, cells, serum, plasma, saliva, urine, stool, sputum, nasopharyngeal aspirates and so forth) that are present in the natural source of the nucleic acid molecule. An isolated nucleic acid molecule, such as a cDNA molecule, can be substantially free of other cellular material or culture medium when produced by recombinant techniques, or substantially free of chemical precursors or other chemicals when chemically synthesized. In some embodiments, nucleic acid molecules encoding polypeptides/proteins may also be isolated or purified. Methods of nucleic acid isolation are well known in the art and may include total nucleic acid isolation/purification methods, RNA-specific isolation/purification methods, or DNA-specific isolation/purification methods.

As used herein, the term "microarray" refers to an arrangement of a plurality of polynucleotides, polypeptides, or other chemical compounds on a substrate. The terms "element" and "array element" refer to a polynucleotide, polypeptide, or other chemical compound having a unique and defined position on a microarray.

As used herein, an oligonucleotide is understood to be a molecule that has a sequence of bases on a backbone comprised mainly of identical monomer units at defined intervals. The bases are arranged on the backbone in such a way that they can enter into a bond with a nucleic acid having a sequence of bases that are complementary to the bases of the oligonucleotide. The most common oligonucleotides have a backbone of sugar phosphate units. A distinction may be made between oligodeoxyribonucleotides, made up of "dNTPs," which do not have a hydroxyl group at the 2' position, and oligoribonucleotides, made up of "NTPs," which have a hydroxyl group in the 2' position. Oligonucleotides also may include derivatives, in which the hydrogen of the hydroxyl group is replaced with an organic group, e.g., an allyl group.

An oligonucleotide is a nucleic acid that includes at least two nucleotides. Oligonucleotides used in the methods disclosed herein typically include at least about ten (10) nucleotides and more typically at least about fifteen (15) nucleotides. Preferred oligonucleotides for the methods disclosed herein include about 10-25 nucleotides. An oligonucleotide may be designed to function as a "primer." A "primer" is a short nucleic acid, usually a ssDNA oligonucleotide, which may be annealed to a target polynucleotide by complementary base-pairing. The primer may then be extended along the target DNA or RNA strand by a polymerase enzyme, such as a DNA polymerase enzyme. Primer pairs can be used for amplification (and identification) of a nucleic acid sequence (e.g., by the polymerase chain reaction (PCR)). An oligonucleotide may be designed to function as a "probe." A "probe" refers to an oligonucleotide, its complements, or fragments thereof, which are used to detect identical, allelic, or related nucleic acid sequences. Probes may include oligonucleotides that have been attached to a detectable label or reporter molecule. Typical labels include fluorescent dyes, quenchers, radioactive isotopes, ligands, scintillation agents, chemiluminescent agents, and enzymes.

An oligonucleotide may be designed to be specific for a target nucleic acid sequence in a sample. For example, an oligonucleotide may be designed to include "antisense" nucleic acid sequence of the target nucleic acid. As used herein, the term "antisense" refers to any composition capable of base-pairing with the "sense" (coding) strand of a specific target nucleic acid sequence. An antisense nucleic acid sequence may be "complementary" to a target nucleic acid sequence. As used herein, "complementarity" describes the relationship between two single-stranded nucleic acid sequences that anneal by base-pairing. For example, 5'-AGT-3' pairs with its complement, 3'-TCA-5'. In some embodiments, primers or probes may be designed to include mismatches at various positions. As used herein, a "mismatch" means a nucleotide pair that does not include the standard Watson-Crick base pairs, or nucleotide pairs that do not preferentially form hydrogen bonds. The mismatch may include a natural nucleotide or a non-natural or non-standard nucleotide substituted across from a particular base or bases in a target. For example, the probe or primer sequence 5'-AGT-3' has a single mismatch with the target sequence 3'-ACA-5'. The 5' "A" of the probe or primer is mismatched with the 3' "A" of the target. Similarly, the target sequence 5'-AGA-3' has a single mismatch with the probe or primer sequence 3'-(iC)CT-5'. Here an iso-C is substituted in place of the natural "T." However, the sequence 3'-(iC)CT-5' is not mismatched with the sequence 5'-(iG)GA-3'.

Oligonucleotides may also be designed as degenerate oligonucleotides. As used herein, "degenerate oligonucleotide" is meant to include a population, pool, or plurality of oligonucleotides comprising a mixture of different sequences where the sequence differences occur at a specified position in each oligonucleotide of the population. Various substitutions may include any natural or non-natural nucleotide, and may include any number of different possible nucleotides at any given position. For example, the above degenerate oligonucleotide may instead include R=iC or iG, or R=A or G or T or C or iC or iG.

Oligonucleotides, as described herein, typically are capable of forming hydrogen bonds with oligonucleotides having a complementary base sequence. These bases may include the natural bases, such as A, G, C, T, and U, as well as artificial, non-standard or non-natural nucleotides such as iso-cytosine and iso-guanine. As described herein, a first sequence of an oligonucleotide is described as being 100% complementary with a second sequence of an oligonucleotide when the consecutive bases of the first sequence (read 5'-to-3') follow the Watson-Crick rule of base pairing as compared to the consecutive bases of the second sequence (read 3'-to-5'). An oligonucleotide may include nucleotide substitutions. For example, an artificial base may be used in place of a natural base such that the artificial base exhibits a specific interaction that is similar to the natural base.

An oligonucleotide that is specific for a target nucleic acid also may be specific for a nucleic acid sequence that has "homology" to the target nucleic acid sequence. As used herein, "homology" refers to sequence similarity or, interchangeably, sequence identity, between two or more polynucleotide sequences or two or more polypeptide sequences. The terms "percent identity" and "% identity" as applied to polynucleotide sequences, refer to the percentage of residue matches between at least two polynucleotide sequences aligned using a standardized algorithm (e.g., BLAST).

An oligonucleotide that is specific for a target nucleic acid will "hybridize" to the target nucleic acid under suitable conditions. As used herein, "hybridization" or "hybridizing" refers to the process by which an oligonucleotide single strand anneals with a complementary strand through base pairing under defined hybridization conditions. "Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Equations for calculating $T_m$, for example, nearest-neighbor parameters, and conditions for nucleic acid hybridization are known in the art.

As used herein, "target" or "target nucleic acid" refers to a nucleic acid molecule containing a sequence that has at least partial complementarity with an oligonucleotide, for example, a probe or a primer. A "target" sequence may include a part of a gene or genome.

As used herein, "nucleic acid," "nucleotide sequence," or "nucleic acid sequence" refer to a nucleotide, oligonucleotide, polynucleotide, or any fragment thereof and to naturally occurring or synthetic molecules. These terms also refer to DNA or RNA of genomic or synthetic origin, which may be single-stranded or double-stranded and may represent the sense or the antisense strand, or to any DNA-like or RNA-like material. An "RNA equivalent," in reference to a DNA sequence, is composed of the same linear sequence of nucleotides as the reference DNA sequence with the exception that all occurrences of the nitrogenous base thymine are replaced with uracil, and the sugar backbone is composed of ribose instead of deoxyribose. RNA may be used in the methods described herein and/or may be converted to cDNA by reverse transcription for use in the methods described herein.

As used herein, "amplification" or "amplifying" refers to the production of additional copies of a nucleic acid sequence. Amplification is generally carried out using polymerase chain reaction (PCR) technologies known in the art. The term "amplification reaction system" refers to any in vitro means for multiplying the copies of a target sequence of nucleic acid. The term "amplification reaction mixture" refers to an aqueous solution comprising the various reagents used to amplify a target nucleic acid. These may include enzymes (e.g., a thermostable polymerase), aqueous buffers, salts, amplification primers, target nucleic acid, nucleoside triphosphates, and optionally, at least one labeled probe and/or optionally, at least one agent for determining the melting temperature of an amplified target nucleic acid (e.g., a fluorescent intercalating agent that exhibits a change in fluorescence in the presence of double-stranded nucleic acid).

The amplification methods described herein may include "real-time monitoring" or "continuous monitoring." These terms refer to monitoring multiple times during a cycle of PCR, preferably during temperature transitions, and more preferably obtaining at least one data point in each temperature transition. The term "homogeneous detection assay" is used to describe an assay that includes coupled amplification and detection, which may include "real-time monitoring" or "continuous monitoring."

Amplification of nucleic acids may include amplification of nucleic acids or subregions of these nucleic acids. For example, amplification may include amplifying portions of nucleic acids between 30 and 50, between 50 and 100, or between 100 and 300 bases long by selecting the proper primer sequences and using PCR. In further aspects, amplification can be achieved using an isothermal amplification technique (i.e., without the need for thermal cycling). For example, methods for isothermal nucleic acid amplification, such as loop mediated isothermal amplification (LAMP), are provided in U.S. Pat. No. 6,410,278, and US. Patent Publn. 20080182312, each of which is incorporated herein by reference in its entirety.

The disclosed methods may include amplifying at least one or more nucleic acids in the sample. In the disclosed methods, amplification may be monitored using real-time methods.

Amplification mixtures may include natural nucleotides (including A, C, G, T, and U) and non-natural or non-standard nucleotides (e.g., including iC and iG). DNA and RNA oligonucleotides include deoxyriboses or riboses, respectively, coupled by phosphodiester bonds. Each deoxyribose or ribose includes a base coupled to a sugar. The bases incorporated in naturally-occurring DNA and RNA are adenosine (A), guanosine (G), thymidine (T), cytosine (C), and uridine (U). These five bases are "natural bases." According to the rules of base pairing elaborated by Watson and Crick, the natural bases hybridize to form purine-pyrimidine base pairs, where G pairs with C and A pairs with T or U. These pairing rules facilitate specific hybridization of an oligonucleotide with a complementary oligonucleotide.

The formation of base pairs by natural bases is facilitated by the generation of two or three hydrogen bonds between the two bases of each base pair. Each of the bases includes two or three hydrogen bond donor(s) and hydrogen bond acceptor(s). The hydrogen bonds of the base pair are each formed by the interaction of at least one hydrogen bond donor on one base with a hydrogen bond acceptor on the other base. Hydrogen bond donors include, for example, heteroatoms (e.g., oxygen or nitrogen) that have at least one attached hydrogen. Hydrogen bond acceptors include, for example, heteroatoms (e.g., oxygen or nitrogen) that have a lone pair of electrons.

The natural or non-natural nucleotides used herein can be derivatized by substitution at non-hydrogen bonding sites to form modified natural or non-natural nucleotides. For example, a natural nucleotide can be derivatized for attachment to a support by coupling a reactive functional group (for example, thiol, hydrazine, alcohol, amine, and the like) to a non-hydrogen bonding atom of the nucleotide. Other possible substituents include, for example, biotin, digoxigenin, fluorescent groups, alkyl groups (e.g., methyl or ethyl), and the like.

The use of non-natural nucleotides according to the methods disclosed herein is extendable beyond the detection and quantification of nucleic acid sequences present in a sample. For example, non-natural nucleotides can be recognized by many enzymes that catalyze reactions associated with nucleic acids. While a polymerase requires a complementary nucleotide to continue polymerizing and extending an oligonucleotide chain, other enzymes do not require a complementary nucleotide. If a non-natural nucleotide is present in the template and its complementary non-natural nucleotide is not present in the reaction mix, a polymerase will typically stall (or, in some instances, misincorporate a base when given a sufficient amount of time) when attempting to extend an elongating primer past the non-natural nucleotide. However, other enzymes that catalyze reactions associated with nucleic acids, such as ligases, kinases, nucleases, polymerases, topoisomerases, helicases, and the like can catalyze reactions involving non-natural nucleotides. Such features of non-natural nucleotides can be taken advantage of, and are within the scope of the presently disclosed methods and kits.

The nucleotides disclosed herein, which may include non-natural nucleotides, may be coupled to a label (e.g., a quencher or a fluorophore). Coupling may be performed using methods known in the art.

The oligonucleotides of the present methods may function as primers. In some embodiments, the oligonucleotides are labeled. For example, the oligonucleotides may be labeled with a reporter that emits a detectable signal (e.g., a fluorophore). The oligonucleotides may include at least one non-natural nucleotide. For example, the oligonucleotides may include at least one nucleotide having a base that is not A, C, G, T, or U (e.g., iC or iG). Where the oligonucleotide is used as a primer for PCR, the amplification mixture may include at least one nucleotide that is labeled with a quencher (e.g., Dabcyl). The labeled nucleotide may include at least one non-natural or non-standard nucleotide. For example, the labeled nucleotide may include at least one nucleotide having a base that is not A, C, G, T, or U (e.g., iC or iG).

In some embodiments, the oligonucleotide may be designed not to form an intramolecular structure, such as a hairpin. In other embodiments, the oligonucleotide may be designed to form an intramolecular structure, such as a hairpin. For example, the oligonucleotide may be designed to form a hairpin structure that is altered after the oligonucleotide hybridizes to a target nucleic acid, and optionally, after the target nucleic acid is amplified using the oligonucleotide as a primer.

The oligonucleotide may be labeled with a fluorophore that exhibits quenching when incorporated in an amplified product as a primer. In other embodiments, the oligonucleotide may emit a detectable signal after the oligonucleotide is incorporated in an amplified product as a primer (e.g., inherently, or by fluorescence induction or fluorescence dequenching). Such primers are known in the art (e.g., LightCycler primers, AmpHum™ primers, Scorpion™ primers, and Lux™ primers). The fluorophore used to label the oligonucleotide may emit a signal when intercalated in double-stranded nucleic acid. As such, the fluorophore may emit a signal after the oligonucleotide is used as a primer for amplifying the nucleic acid.

The oligonucleotides that are used in the disclosed methods may be suitable as primers for amplifying at least one nucleic acid in the sample and as probes for detecting at least one nucleic acid in the sample. In some embodiments, the oligonucleotides are labeled with at least one fluorescent dye, which may produce a detectable signal. The fluorescent dye may function as a fluorescence donor for fluorescence resonance energy transfer (FRET). The detectable signal may be quenched when the oligonucleotide is used to amplify a target nucleic acid. For example, the amplification mixture may include nucleotides that are labeled with a quencher for the detectable signal emitted by the fluorophore. Optionally, the oligonucleotides may be labeled with a second fluorescent dye or a quencher dye that may function as a fluorescence acceptor (e.g., for FRET). Where the oligonucleotide is labeled with a first fluorescent dye and a second fluorescent dye, a signal may be detected from the first fluorescent dye, the second fluorescent dye, or both. Signals may be detected at a gradient of temperatures (e.g., in order to determine a melting temperature for an amplicon, a complex that includes a probe hybridized to a target nucleic acid, a hairpin, or a T probe complex).

The disclosed methods may be performed with any suitable number of oligonucleotides. Where a plurality of oligonucleotides are used (e.g., two or more oligonucleotides), different oligonucleotide may be labeled with different fluorescent dyes capable of producing a detectable signal. In some embodiments, oligonucleotides are labeled with at least one of two different fluorescent dyes. In further embodiments, oligonucleotides are labeled with at least one of three different fluorescent dyes.

In some embodiments, each different fluorescent dye emits a signal that can be distinguished from a signal emitted by any other of the different fluorescent dyes that are used to label the oligonucleotides. For example, the different fluorescent dyes may have wavelength emission maximums all of which differ from each other by at least about 5 nm (preferably by least about 10 nm). In some embodiments, each different fluorescent dye is excited by different wavelength energies. For example, the different fluorescent dyes may have wavelength absorption maximums all of which differ from each other by at least about 5 nm (preferably by at least about 10 nm).

Where a fluorescent dye is used to determine the melting temperature of a nucleic acid in the method, the fluorescent dye may emit a signal that can be distinguished from a signal emitted by any other of the different fluorescent dyes that are used to label the oligonucleotides. For example, the fluorescent dye for determining the melting temperature of a nucleic acid may have a wavelength emission maximum that differs from the wavelength emission maximum of any other fluorescent dye that is used for labeling an oligonucleotide by at least about 5 nm (preferably by least about 10 nm). In some embodiments, the fluorescent dye for determining the melting temperature of a nucleic acid may be excited by different wavelength energy than any other of the different fluorescent dyes that are used to label the oligonucleotides. For example, the fluorescent dye for determining the melting temperature of a nucleic acid may have a wavelength absorption maximum that differs from the wavelength absorption maximum of any fluorescent dye that is used for labeling an oligonucleotide by at least about 5 nm (preferably by at least about 10 nm).

The methods may include determining the melting temperature of at least one nucleic acid in a sample (e.g., an amplicon or a nucleic acid complex that includes a probe hybridized to a target nucleic acid), which may be used to identify the nucleic acid. Determining the melting temperature may include exposing an amplicon or a nucleic acid complex to a temperature gradient and observing a detectable signal from a fluorophore. Optionally, where the oligonucleotides of the method are labeled with a first fluorescent dye, determining the melting temperature of the detected nucleic acid may include observing a signal from a second fluorescent dye that is different from the first fluorescent dye. In some embodiments, the second fluorescent dye for determining the melting temperature of the detected nucleic acid is an intercalating agent. Suitable intercalating agents may include, but are not limited to SYBR™ Green 1 dye, SYBR dyes, Pico Green, SYTO dyes, SYTOX dyes, ethidium bromide, ethidium homodimer-1, ethidium homodimer-2, ethidium derivatives, acridine, acridine orange, acridine derivatives, ethidium-acridine heterodimer, ethidium monoazide, propidium iodide, cyanine monomers, 7-aminoactinomycin D, YOYO-1, TOTO-1, YOYO-3, TOTO-3, POPO-1, BOBO-1, POPO-3, BOBO-3, LOLO-1, JOJO-1, cyanine dimers, YO-PRO-1, TO-PRO-1, YO-PRO-3, TO-PRO-3, TO-PRO-5, PO-PRO-1, BO-PRO-1, PO-PRO-3, BO-PRO-3, LO-PRO-1, JO-PRO-1, and mixtures thereof. In suitable embodiments, the selected intercalating agent is SYBR™ Green 1 dye.

In the disclosed methods, each of the amplified target nucleic acids or reporter probe-template pairs may have different melting temperatures. For example, each of the amplified target nucleic acids or reporter probe-template pairs may have melting temperatures that differ by 1-10° C., for example, at least about 1° C., more preferably by at least about 2° C., or even more preferably by at least about 4° C. from the melting temperature of any of the other amplified target nucleic acids or reporter probe-template pairs.

As used herein, "labels" or "reporter molecules" are chemical or biochemical moieties useful for labeling a nucleic acid. "Labels" and "reporter molecules" include fluorescent agents, chemiluminescent agents, chromogenic agents, quenching agents, radionuclides, enzymes, substrates, cofactors, scintillation agents, inhibitors, magnetic particles, and other moieties known in the art. "Labels" or "reporter molecules" are capable of generating a measurable signal and may be covalently or noncovalently joined to an oligonucleotide.

As used herein, a "fluorescent dye" or a "fluorophore" is a chemical group that can be excited by light to emit fluorescence. Some suitable fluorophores may be excited by light to emit phosphorescence. Dyes may include acceptor dyes that are capable of quenching a fluorescent signal from a fluorescent donor dye. Dyes that may be used in the disclosed methods include, but are not limited to, fluorophores such as, a red fluorescent squarine dye such as 2,4-Bis[1,3,3-trimethyl-2-indolinylidenemethyl]cyclobutenediylium-1,3-dio-xolate, an infrared dye such as 2,4 Bis[3,3-dimethyl-2-(1H-benz[e]indolinylidenemethyl)]cyclobutenediylium-1,-3-dioxolate, or an orange fluorescent squarine dye such as 2,4-Bis[3,5-dimethyl-2-pyrrolyl]cyclobutenediylium-1,3-diololate. Additional non-limiting examples of fluorophores include quantum dots, Alexa Fluor™ dyes, AMCA, BODIPY™ 630/650, BODIPY™ 650/665, BODIPY™-FL, BODIPY™-R6G, BODIPY™-TMR, BODIPY™-TRX, Cascade Blue™, CyDye™, including but not limited to Cy2™, Cy3™, and Cy5™, a DNA intercalating dye, 6-FAM™, Fluorescein, HEX™, 6-JOE, Oregon Green™ 488, Oregon Green™ 500, Oregon Green™ 514, Pacific Blue™, REG, phycobilliproteins including, but not limited to, phycoerythrin and allophycocyanin, Rhodamine Green™, Rhodamine Red™, ROX™, TAMRA™, TET™, Tetramethylrhodamine, or Texas Red™.

Fluorescent dyes or fluorophores may include derivatives that have been modified to facilitate conjugation to another reactive molecule. As such, fluorescent dyes or fluorophores may include amine-reactive derivatives, such as isothiocyanate derivatives and/or succinimidyl ester derivatives of the fluorophore.

The oligonucleotides and nucleotides of the disclosed methods may be labeled with a quencher. Quenching may include dynamic quenching (e.g., by FRET), static quenching, or both. Suitable quenchers may include Dabcyl. Suitable quenchers may also include dark quenchers, which may include black hole quenchers sold under the trade name "BHQ" (e.g., BHQ-0, BHQ-1, BHQ-2, and BHQ-3, Biosearch Technologies, Novato, Calif.). Dark quenchers also may include quenchers sold under the trade name "QXL™" (Anaspec, San Jose, Calif.). Dark quenchers also may include DNP-type non-fluorophores that include a 2,4-dinitrophenyl group.

The methods and compositions disclosed herein may be used in compartmentalized reactions. One approach for compartmentalizing reactions is by using droplets, which are isolated volumes of a first fluid that are completely surrounded by a second fluid or by a second fluid and one or more surfaces. In the molecular diagnostics and life science research fields this is typically two immiscible liquids. Various embodiments disclosed herein employ a water-in-oil emulsion comprising a plurality of aqueous droplets in a non-aqueous continuous phase. All or a subset of the aqueous droplets may contain an analyte of interest. Emulsions are formed by combining two immiscible phases (e.g., water and oil), often in the presence of one or more surfactants. Basic types of emulsions are oil-in-water (o/w), water-in-oil (w/o), and bi-continuous. In droplet-based biological assays, the emulsion will typically be a water-in-oil emulsion with the assay reagents (e.g., PCR primers, salts, enzymes, etc.) contained in the aqueous phase. The "oil" phase may be a single oil or a mixture of different oils. Any suitable non-aqueous fluid may form the non-aqueous continuous phase of the emulsions disclosed herein. In some embodiments, the non-aqueous continuous phase comprises a mineral oil, a silicone oil, or a fluorinated oil (e.g., Fluorinert® FC-40 [Sigma-Aldrich]).

The droplets may be imaged by a variety of techniques. To facilitate imaging, the composition containing the droplets may be dispersed on a surface such that the droplets are disposed substantially in a monolayer on the surface. The imaging surface may be, for example, on a slide or in a chamber, such as a glass or quartz chamber. The droplets, as well as labeled analytes or reaction products (e.g., hairpin probes) within the droplets, may be detected using an imaging system. For example, detection may comprise imaging fluorescent wavelengths and/or fluorescent intensities emitted from the labeled hairpin probes. In embodiments where the droplets also contain encoded particles, such as encoded microspheres, the imaging may comprise taking a decoding image of the encoded particles and taking an assay imaging to detect the probes in the droplets. A comparison of the decoding image and the assay image permits greater multiplex capabilities by using combinations of fluorophores. The methods of the present invention may further comprise correlating the signal from the directly or indirectly labeled amplification product with the concentration of DNA or RNA in a sample. Examples of imaging systems that could be adapted for use with the methods and compositions disclosed herein are described in U.S. Pat. No. 8,296,088 and U.S. Pat. Publ. 2012/0288897, which are incorporated herein by reference.

As discussed above, the polymerase chain reaction (PCR) is an example of a reaction that may be performed within a droplet. In particular, droplets are useful in digital PCR (dPCR) techniques. dPCR involves partitioning the sample such that individual nucleic acid molecules contained in the sample are localized in many separate regions, such as in individual wells in microwell plates, in the dispersed phase of an emulsion, or arrays of nucleic acid binding surfaces. Each partition (e.g., droplet) will contain 0 or greater than zero molecules, providing a negative or positive reaction, respectively. Unlike conventional PCR, dPCR is not dependent on the number of amplification cycles to determine the initial amount of the target nucleic acid in the sample. Accordingly, dPCR eliminates the reliance on exponential data to quantify target nucleic acids and provides absolute quantification. Bead emulsion PCR, which clonally amplifies nucleic acids on beads in an emulsion, is one example of a dPCR technique in which the reactions are portioned into droplets. See, e.g., U.S. Pat. Nos. 8,048,627 and 7,842,457, which are hereby incorporated by reference. When dPCR is performed in an emulsion as discussed in more detail below, the emulsion should be heat stable to allow it to withstand thermal cycling conditions.

There are various ways of performing dPCR in an emulsion. For example, in one approach a DNA sample is diluted to an appropriate concentration, mixed with PCR reagents (primers, dNTPs, etc.) and encapsulated in droplets in an emulsion as described above, resulting in a number of discrete reaction samples. The droplets are subjected to PCR thermal cycling and the amplicons detected by florescence (or other suitable reporter) imaging as described above. In the context of the present cleavable probe embodiments, the amplicons are detected by florescence (or other suitable reporter) of the probes.

The thermal cycling of the droplets may be performed by any suitable technique known in the art. For example, the droplets may be thermal cycled in a tube or chamber than can be heated and cooled. In some embodiments, the methods employ continuous-flow amplification to amplify the nucleic acid template. Various methods of continuous flow amplification have been reported. For example, U.S. Pat. No. 7,927,797, which in incorporated herein by reference, describes a water-in-oil emulsion used in conjunction with a continuous flow PCR. Isothermal reactions (e.g., rolling circle amplification, whole genome amplification, NASBA, or strand displacement amplification) may also be performed in droplets. The system may also be used to monitor the droplets while increasing or decreasing the temperature to obtain melt profiles per droplet, which will allow for multiplexed detection and quantification. The probes themselves may be used within droplets to isothermally amplify signal such that other forms of amplification such as PCR or other isothermal amplification reactions are not necessary to detect low copy numbers of target within a droplet.

II. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Multiprobe Probe Systems

Solution phase multiplexing strategies for molecular assays rely on the use of multiple fluorophores in conjunction with generation of multiple fluorescence melt curves for detection of >10 targets. Various embodiments disclosed herein provide a real time probe based chemistry that allows higher multiplexing capabilities to be achieved by utilizing extendable hairpin probes to create multiple melt curves per channel. An example of probes for use in this system is shown in FIG. 1A. In this example, the cleavable probe comprises a reporter-labeled isoG nucleotide ("isoG*") at its 5' end, a first sequence region ("Tag A"), a second sequence region ("Tag B"), a loop sequence, a sequence region that is the reverse compliment of Tag B ("Tag B complement"); and a sequence complementary to the target amplicon (indicated as "A"). The cleavable probe also comprises one or more ribonucleotides (indicated by the solid square) in the "A" sequence and may comprise a modification that blocks extension on the 3' end (indicated as "P"). In the presence of a target amplicon, the cleavable probe hybridizes to the amplicon and is cleaved at the ribonucleotide position by RNase H2 (which recognizes and cleaves ribonucleotides in an annealed RNA/DNA hybrid). Following cleavage, the probe can hybridize to itself via the Tag B and Tag B complement sequences to form a hairpin. Extension of the probe will synthesize sequences complementary to the Tag A sequences and will incorporate a quencher labeled isoC ("isoC$^Q$"). The resulting hairpin probe quenches the fluorescence of the labeled isoG. The probes can be designed to have unique melt temperatures ($T_m$), such as by adjusting the sequence and length of the first and second sequence regions. Thus, the composition and length of the Tag A and Tag B stem structures can be varied to resolve in any desired melt temperature for the hairpin probe (see, FIG. 1B).

Materials and Methods
Probe Design Parameters

Multiple constructs of cleavable probes were designed without a target sequence specific tail (post cleavage) to determine optimal design parameters for an extendable hairpin. The targeted $T_m$ for the sequence specific tail was 10° C. above the reaction temperature (~58° C.). The hairpin constructs were designed to have a $T_m$>60° C. to allow for the formation of the unimolecular structure post cleavage of RNA/DNA hybrid. These constructs were designed to determine requirements for loop size (number of bases), stem size, Gibbs free energy and $T_m$ of the hairpin post cleavage. Examples of specific probes that were constructed are shown (FIG. 2). For these proof of concept experiments, a loop of multi-adenine residues ending with two cytosine "clamps" at each side of the loop was used (sequence between the font in italics).

1. Folding of the Probes

Temperature gradient was used to assess the folding profile of these constructs by monitoring the decrease of fluorescence intensity of the hairpin over temperatures ranging from 95° C. to 41° C. The constructs of FIG. 2 were added to a reaction mixture containing BTP-KCl pH 9.1 buffer, 2.5 mM dNTPs, 2.5 mM MgCl$_2$, 1 mM Dabcyl-isoG and Titanium Taq enzyme (Clontech). After initial denaturation step at 95° C., the reaction temperature was decreased from 95° C. to 41° C. by 3° C. increments with a hold of 10 seconds at each interval. The temperature at which complete quenching was observed for each construct was recorded as the folding temperature of the hairpin.

2. Efficiency of Hairpin-Loop Formation: Folding, Extending and Quenching of the Probes The efficiency of the hairpin formation was evaluated by measuring rate of quenching of each construct at 3 temperatures. Constructs of FIG. 2 were added to a reaction mixture containing BTP-KCl pH 9.1 buffer, 2.5 mM dNTPs, 1 mM isoG-dabcyl- and Titanium Taq enzyme (Clontech). After 2 minutes of activation step at 95° C., the reaction was incubated at 50° C., 62° C. and 68° C. for 30 minutes to allow for hairpins to fold, extend and incorporate isoG-dabcyl. This was followed by a melt curve cycling protocol of 60° C. 30 s and incremental increase to 95° C. The efficiency of the reaction was determined by the Ct values generated when quenching was achieved.

3. Single-Plex RT-PCR with Full Length Probes

Feasibility of using the multiprobe RTx probes for detection in an amplification reaction was first evaluated in a singleplex RT-PCR reaction. Multiple designs of the full length probes (with sequence specific tail) were generated based on the hairpin designs assessed in (FIGS. 2-3). The target $T_m$ for the sequence specific segment was ~10° C. higher than the annealing temperature of the reaction. The sequence of the primers (Table 1) and probes were based on the matrix gene of Influenza B virus. Nucleic acid extracted from Influenza B Strain: B/Malaysia/2506/04 (Zeptometrix) was used as a template in a one-step RT-PCR reaction. Specifically, PCR primers (forward 180 nM, reverse 60 nM) and probe (120 nM) were added to a reaction mixture containing BTP-KCl pH 9.1 buffer, 2.5 mM dNTPs, 2.5 mM MgCl$_2$, 1 mM Dabcyl-isoG, Titanium Taq enzyme (Clontech) and MMLV (Promega) and RNase H (IDT). The following cycling conditions were used for amplification and melt curve analysis: 50° C., 5 minutes; 95° C. for 10 minutes; 95° C. for 10 s, 58° C. for 20 s for 45 cycles followed by a melt program of 60° C. for 30 s and 95° C. 1 s ending with a cooling step at 40° C.

TABLE 1

PCR primers.

| Primer name | Sequence | $T_m$ (° C.) |
|---|---|---|
| FluB Fwd-short | GAA GCA TTT GAA ATA GCA GAA GG (SEQ ID NO: 22) | 61 |
| FluB Rev-short | CAC AGA GCG TTC CTA GTT TTA CT (SEQ ID NO: 23) | 62.8 |

Results
Melt Profile of Hairpin Loops

The melt profile of the hairpin probes of FIG. 2 were generated to determine the folding temperature of various constructs. This was measured by monitoring drop in fluorescence intensity over a temperature gradient of 95° C. to 41° C. (FIG. 4). Graphs showing the quenching profile for three exemplary constructs RTx-5, RTx-10 and RTx-11 are shown in FIGS. 5-7, respectively. The results of all studies are shown in Table 2, below. It was found that hairpin constructs RTx-1, 2, 3, 5, 6, 7, and 8 are completely quenched by 71° C. temperature step corresponding to calculated $T_m$ of the extended hairpin ~71° C. (IDT). Hairpin constructs RTx-4, 9 and 10 are quenched by the 62° C. and hairpin RTx-11 at 41° C.

TABLE 2

Summary of folding temperature for various hairpin probes.

| Construct | Folding Temperature (° C.) | Stem (bp) | loop (bp) | deltaG (kcal · mole−1) | Tm stem loop (° C.) | % GC |
|---|---|---|---|---|---|---|
| RTx-1 | 71 | 8 | 7 | −1.27 | 64.8 | 50 |
| RTx-2 | | 8 | 12 | −1.06 | 63.6 | 50 |

TABLE 2-continued

Summary of folding temperature for various hairpin probes.

| Construct | Folding Temperature (° C.) | Stem (bp) | loop (bp) | deltaG (kcal · mole−1) | Tm stem loop (° C.) | % GC |
|---|---|---|---|---|---|---|
| RTx-3 | | 7 | 7 | −0.87 | 63.3 | 57 |
| RTx-5 | | 9 | 7 | −1.62 | 65.7 | 44 |
| RTx-6 | | 9 | 12 | −1.41 | 64.6 | 44 |
| RTx-7 | | 8 | 7 | −0.93 | 62.9 | 50 |
| RTx-8 | | 8 | 12 | −0.72 | 61.8 | 50 |
| RTx-4 | 62 | 7 | 12 | −0.66 | 62 | 57 |
| RTx-9 | | 6 | 7 | −0.26 | 59.8 | 67 |
| RTx-10 | | 6 | 7 | −0.53 | 61.7 | 67 |
| RTx-11 | 41 | 5 | 7 | −0.5 | 62 | 80 |

When the $T_m$ of stem loop, deltaG values, loop size and stem size are compared the data suggests that the main factor influencing the formation of the hairpin is the number of bases in the stem. The secondary factor may be the Gibbs Free energy associated with the folding of the hairpin as the delta G of the constructs with the correct folding $T_m$ are lower than the constructs with $T_m$'s of 62° C. and 41° C.

Efficiency of Hairpin Loop Formation

Amplification

Figure 10C:
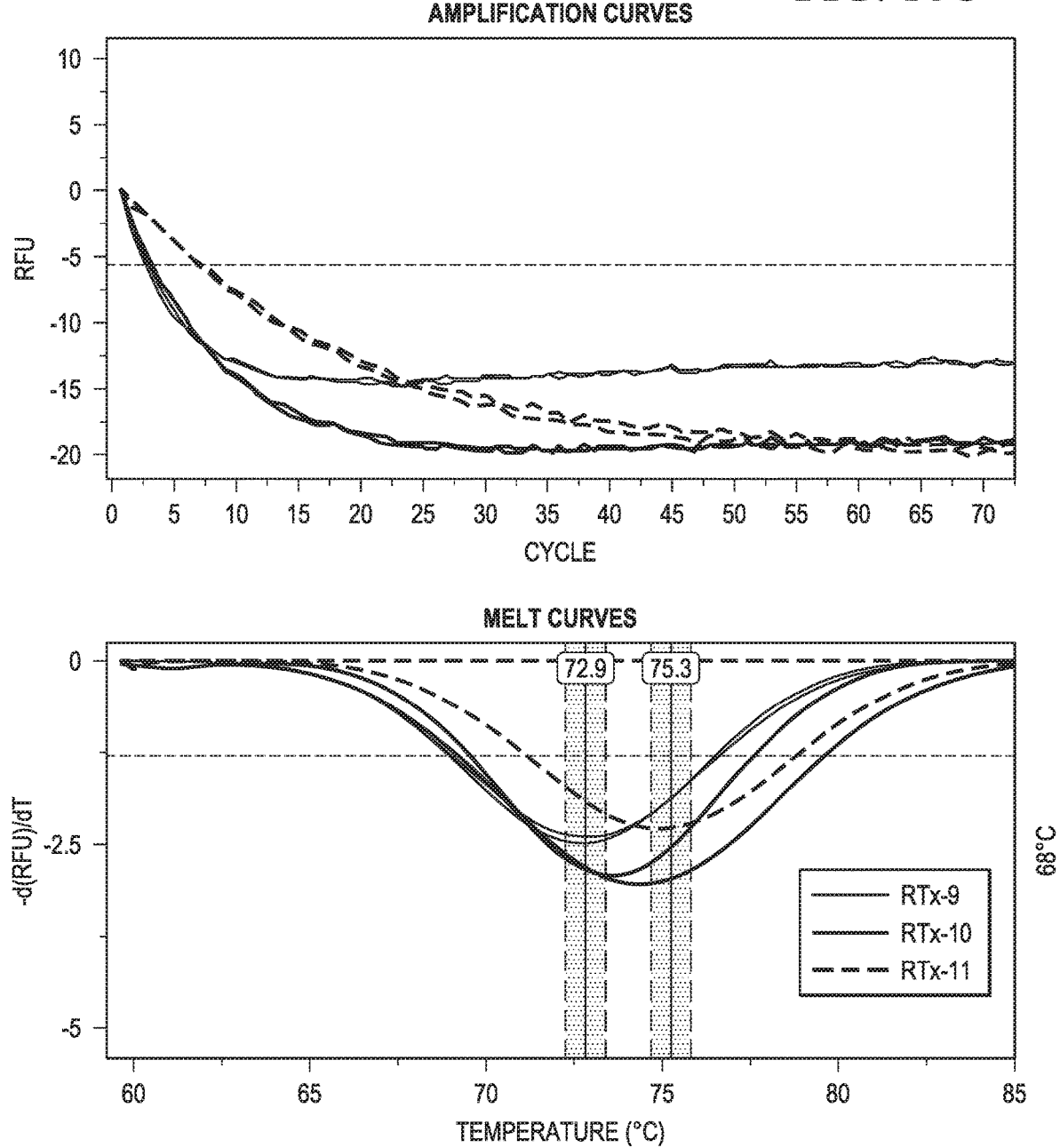
Figure 11C:
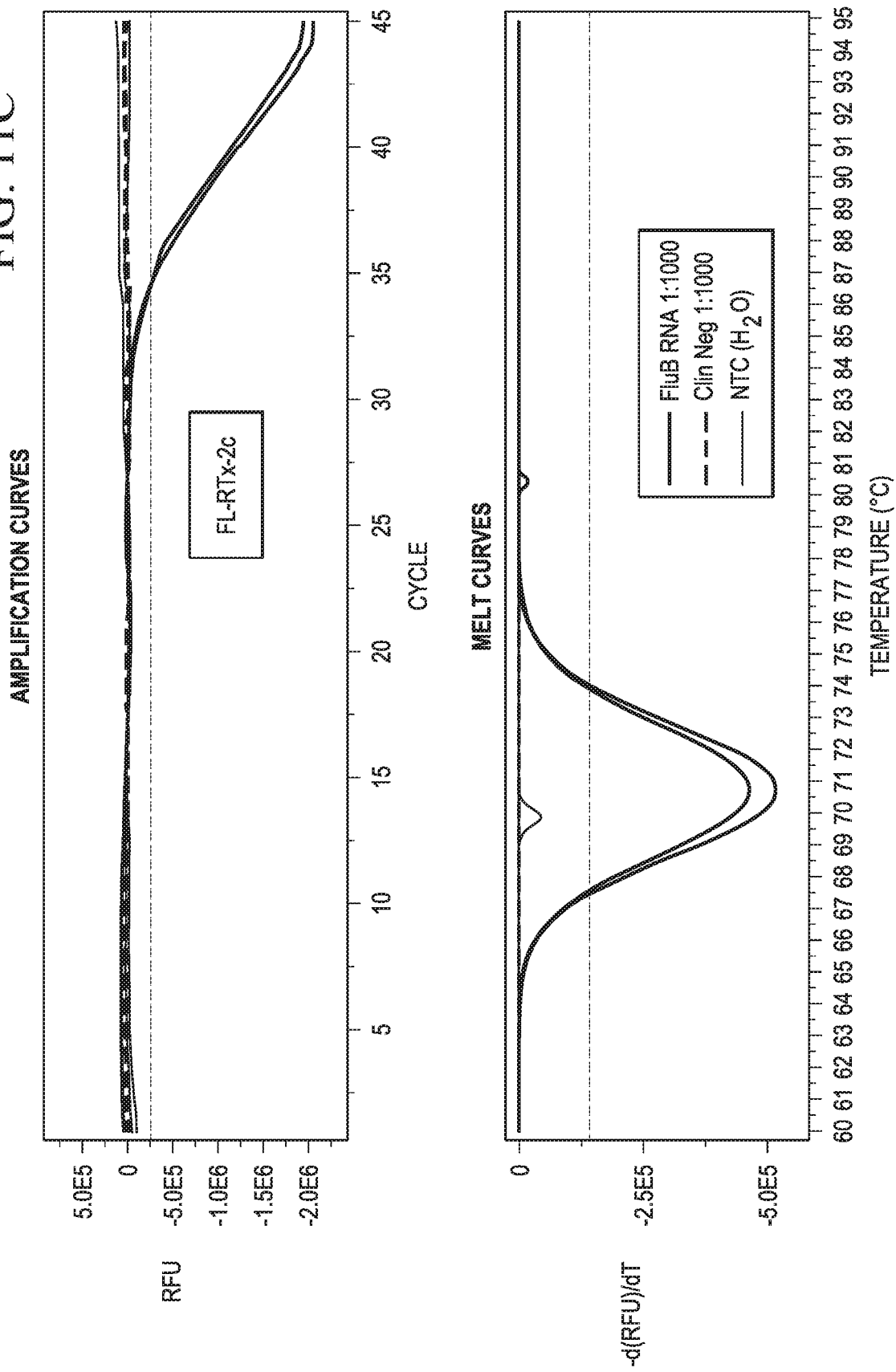

The hairpin constructs from FIG. 2 were used to determine the efficiency of hairpin formation at various temperatures. The results confirm the observations made in above. The reaction rates are very fast for probes RT-x 1, 2, 7, and 8 (FIG. 8 and FIG. 9). Slower reaction rates were observed for probes RTx-9 and 10, Ct values ranged from 5-10 and the highest Ct value recorded for complete quenching was for RTx 11, 30-35 (FIG. 10). These hairpins require lower temperatures to form and extend, which translates into longer times required for folding.

Melt Curve Analysis

Melt curves analysis of hairpin constructs RTx 1, 2, 3, and 4 show that increasing temperature results in sharper melt curves (FIG. 8). This is accompanied by slight shift in the recorded $T_m$. Sharper melt curves were likewise generated at 62° C. with constructs RT-x 5 and 6, and no shift in $T_m$ is observed. Melt curves and $T_m$s of constructs RTx-7 and 8 deviate from the trend observed for the other hairpins (FIG. 9). Wide and overlapping melt curves were generated with constructs RTx 9, 10, and 11, (FIG. 10) corresponding to data generated above.

Single-Plex RT-PCR with Full Length Probes

Full length probe designs were created based on the data generated on the hairpin constructs from FIG. 2 and FIG. 3. Minimum stem size targeted was 8 bases, 12-20 residues for the loop and a $T_m$ of 55° C.-66.4° C. for the hairpin loop.

Detection

All probes generated Ct values in the range of 34-35 Cts (FIGS. 11A-11D). Melt curves of most probes indicated the presence of one species, mainly the extended hairpin. Minor, high $T_m$ peaks were detected for some of the probes.

The same fluorescence intensity was recorded for all the probes with the exception of FL-RTx-2-12AT1 and FL-RTx-2-12AT2. The calculated hairpin loop $T_m$ of these probes is very close to the reaction temperature (58° C.). Reducing the reaction temperature may improve the number of hairpin molecules formed and provide better detection.

Specificity

Two negative controls were included (FIGS. 11A-11D). The purpose for including a template negative control (water) was to detect formation of the hairpin non-specifically due to cleavage of the full length probe by RNase H2. Only probe FL-RTx-2-12-AT-4 (FIG. 11D) showed background non-specific melt curve, the same size as the hairpin which might suggest non-specific cleavage of the probe. The second negative control used was clinical negative specimen collected from asymptomatic patients. The objective was to evaluate the specificity of the probe in the presence of unrelated template. None of the probes showed any non-specific interaction with the template.

Example 2—Additional Hairpin Probe Detection Systems

Figure 12:
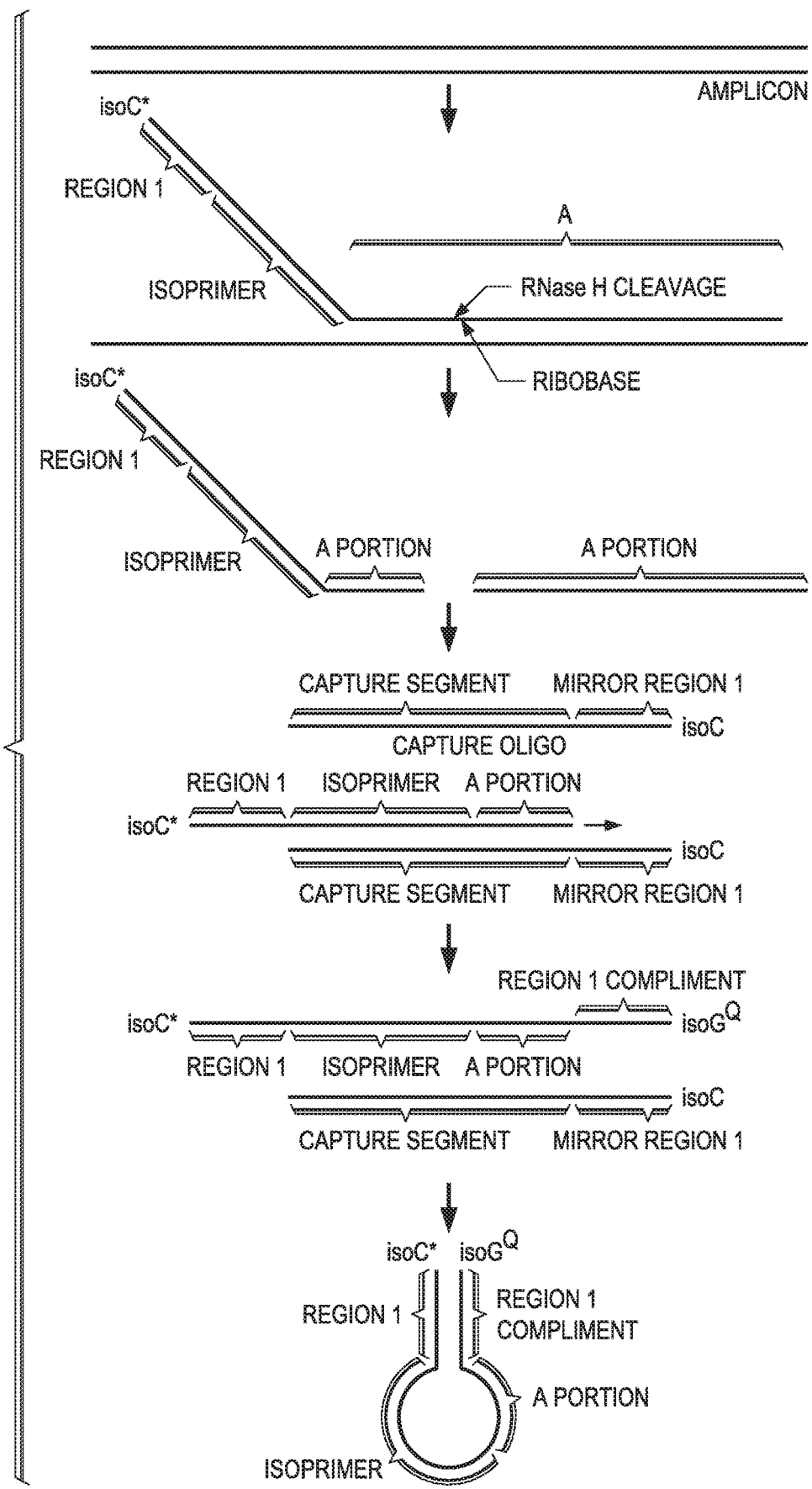
FIG. 12—A non-limiting exemplary schematic showing a probe system of the embodiments. The reporter probe comprises a reporter-labeled isoC nucleotide ("isoC*") at its 5' end, a first sequence region ("region 1"), a sequence that includes isoG and/or isoC positions (the "isoprimer"); and a sequence complementary to the amplicon (indicated as "A"). The sequence that is complementary to the amplicon also includes at least one ribonucleotide position. In the presence of a target amplicon the reporter probe hybridizes to the amplicon and is cleaved at the ribonucleotide position by RNase H. Following cleavage, the reporter probe can hybridize to a capture oligonucleotide ("capture oligo"), which comprises a capture segment complimentary to the isoprimer and, optionally, a portion that "A" sequence, followed by a mirror tag region and a 3' unlabeled isoC. Extension of the reporter probe will synthesize sequences complementary to the mirror region 1 on the capture oligo and will incorporate a quencher labeled isoG ("isoG$^Q$"). The extended reporter probe now includes a region 1 and region 1 complement sequence, which allows the probe to form a hairpin and thereby quench the fluorescence of the labeled isoC. The probes can be designed to have unique melt temperatures ($T_m$), such as by adjusting the sequence and length of the first sequence region. Thus, a melt analysis can be performed to differentiation probes having different melt temperatures (and thus unquenching at different temperatures).

A further example of a hairpin probe detection system is shown in FIG. 12. The reporter probe comprises a reporter-labeled isoC nucleotide ("isoC*") at its 5' end, a first sequence region ("region 1"), a sequence that includes isoG and/or isoC positions (the "isoprimer"); and a sequence complementary to the amplicon (indicated as "A"). The sequence that is complementary to the amplicon also includes at least one ribonucleotide position. In the presence of a target amplicon the reporter probe hybridizes to the amplicon and is cleaved at the ribonucleotide position by RNase H. Following cleavage, the reporter probe can hybridize to a capture oligonucleotide ("capture oligo"), which comprises a capture segment complimentary to the isoprimer and, optionally, a portion that "A" sequence, followed by a mirror region 1 and a 3' unlabeled isoC. Extension of the reporter probe will synthesize sequences complementary to the mirror tag on the capture oligo and will incorporate a quencher labeled isoG ("isoG$^Q$"). The extended reporter probe now includes a tag and tag complement sequence, which allows the probe to form a hairpin and thereby quench the fluorescence of the labeled isoC. The probes can be designed to have unique melt temperatures ($T_m$), such as by adjusting the sequence and length of the first sequence region. Thus, a melt analysis can be performed to differentiation probes having different melt temperatures (and thus unquenching at different temperatures).

The assay system of FIG. 12 may also be further modified, such that the capture probe does not require the isobase. In this system, the reporter probe comprises a reporter-labeled isoC nucleotide ("isoC*") at its 5' end, a first sequence region ("region 1"), a sequence that includes isoG and/or isoC positions (the "isoprimer"); and a sequence complementary to the amplicon (indicated as "A"). The sequence that is complementary to the amplicon also includes at least one ribonucleotide position. In the presence of a target amplicon the reporter probe hybridizes to the amplicon and is cleaved at the ribonucleotide position by RNase H. Following cleavage, the reporter probe can hybridize to a capture oligonucleotide ("capture oligo"), which comprises a capture segment complimentary to the isoprimer and, optionally, a portion that "A" sequence, followed by a mirror region 1 (which is identical to part of the of the region 1 sequence). Extension of the reporter probe will synthesize sequences complementary to the mirror region 1 on the capture oligo. The cleavable probe can then form a hairpin by base pairing of the region 1 sequence with the sequence that is complementary to the mirror region 1. Further extension of the hairpin sequence and will incorporate a quencher labeled isoG ("isoG$^Q$"). The probes can be designed to have unique melt temperatures ($T_m$), such as by adjusting the sequence and length of the first sequence region. Thus, a melt analysis can be performed to differentiation probes having different melt temperatures (and thus unquenching at different temperatures).

Figure 15:
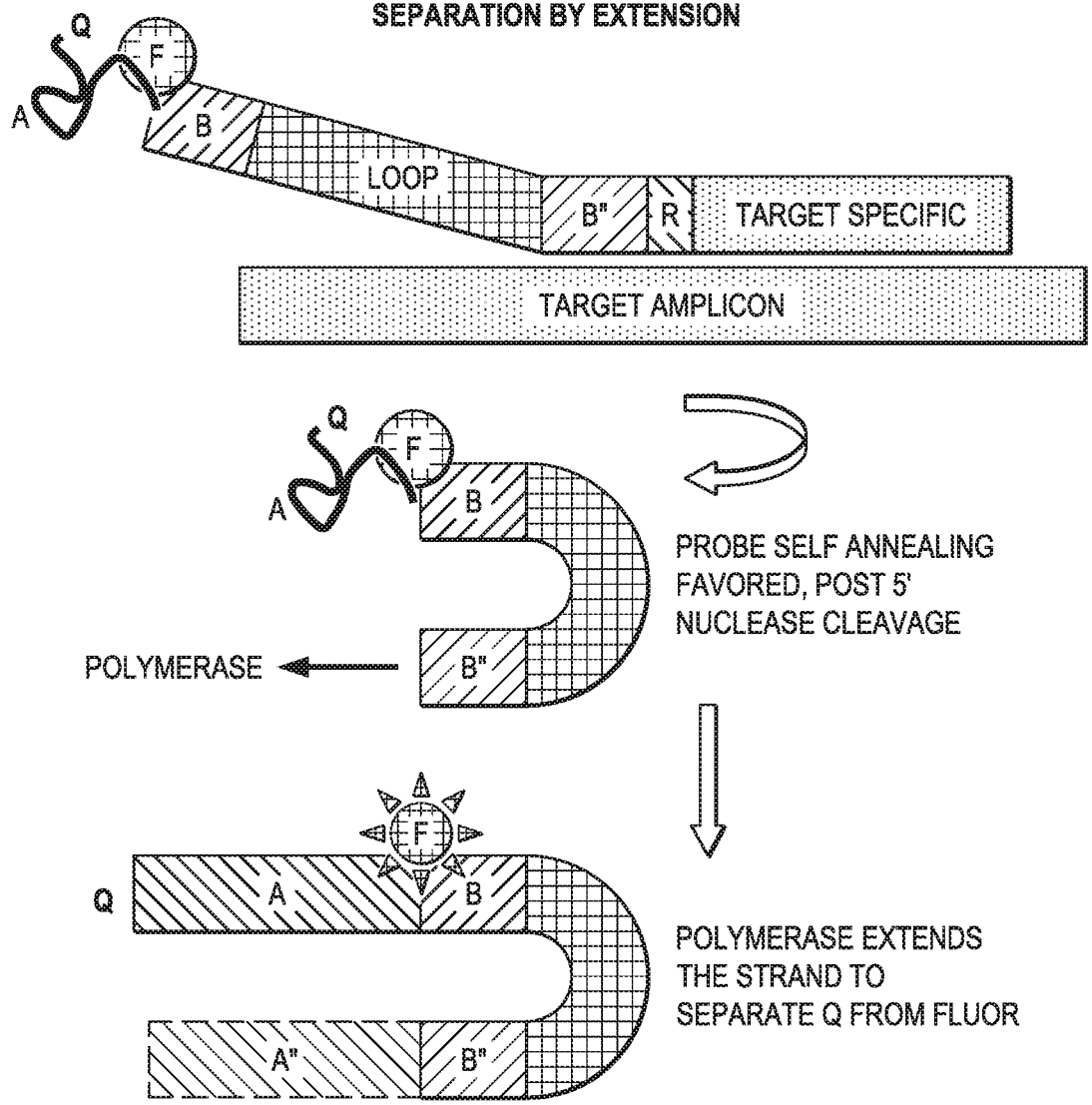
FIG. 15—A non-limiting exemplary schematic showing a probe system of the embodiments in which the probe comprises both a fluorophore ("F") and a quencher ("Q"), and ribocleavage ("R") site. Following cleavage at the ribocleavage site, extension results in separation of the fluorophore and quencher such that a detectable change in the signal can be observed.

FIG. 15 shows another embodiment in which the probe comprises both a fluorophore (F) and a quencher (Q). The conformation of the first sequence region when single-stranded is such that the proximity of the fluorophore to the quencher results in detectable quenching of the signal from the fluorophore. In the presence of a target, the probe hybridizes to the target and is cleaved at the ribonucleotide position by a ribonuclease. In this particular embodiment, the second sequence region complement, the ribonucleotide(s), and the target specific region 3' of the ribonucleotide(s) are complementary to the target. Following cleavage of the probe, the second sequence region and the second sequence region complement of the cleaved probe hybridize to each other to form a hairpin structure. Extension of the 3' end of the cleaved probe onto the first sequence region creates a double-stranded molecule having a conformation that places the fluorophore at a greater distance from the quencher such that a detectable change in the signal can be observed.

Figure 16:
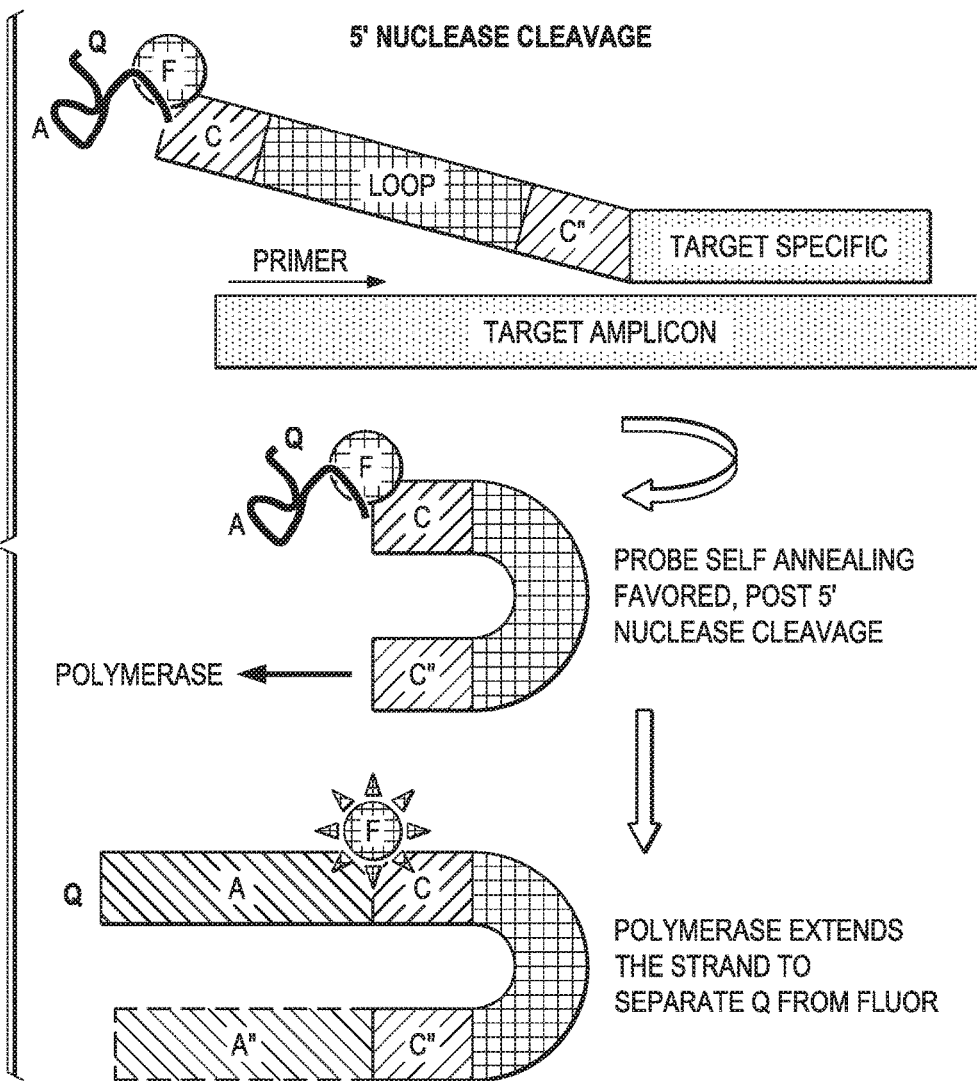
FIG. 16—A non-limiting exemplary schematic showing a probe system of the embodiments in which the probe comprises both a fluorophore ("F") and a quencher ("Q"). 5' nuclease cleavage followed by extension results in separation of the fluorophore and quencher such that a detectable change in the signal can be observed.

FIG. 16 shows another embodiment in which the probe comprises both a fluorophore (F) and a quencher (Q). The conformation of the first sequence region when single-stranded is such that the proximity of the fluorophore to the quencher results in detectable quenching of the signal from the fluorophore. In the presence of a target, the probe hybridizes to the target and is cleaved by the 5' nuclease activity of a polymerase extending an upstream primer. In this particular embodiment, the second sequence region complement is not complementary to the target. Following cleavage of the probe, the second sequence region and the second sequence region complement of the cleaved probe hybridize to each other to form a hairpin structure. Extension of the 3' end of the cleaved probe onto the first sequence region creates a double-stranded molecule having a conformation that places the fluorophore at a greater distance from the quencher such that a detectable change in the signal can be observed.

Figure 17:
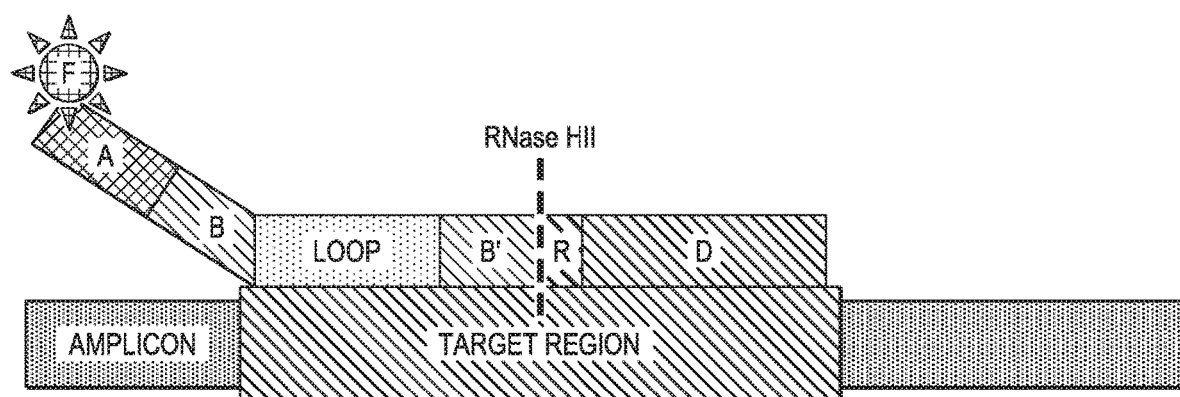
FIG. 17—A non-limiting exemplary schematic showing a probe system of the embodiments in which the probe comprises a loop sequence of one or more nucleotides located between the second sequence region and the sequence that is the reverse complement of the second sequence region (B and B'), wherein the loop sequence is complimentary to a sequence of the target nucleic acid.

FIG. 17 shows an embodiment in which the probe comprises one member of a reporter-quencher pair, in this particular case it is a fluorophore (F). In addition, the probe comprises a first sequence region, a second sequence region, a loop region, a second sequence region complement, one or more ribonucleotide(s), and a target specific region 3' of the ribonucleotide(s). In this particular embodiment, the loop region, the second sequence region complement, the ribonucleotide(s), and the target specific region 3' of the ribonucleotide(s) are complementary to the target.

Example 3—Use of Hairpin Probes with Extension Blockers in Reverse Transcription PCR Fwd and Rev primers were combined in a well with either ATG0015 probe or T-FL-RTx2c probe, which differed only in that ATG00015 probe contained a 3 Carbon spacer (iSpC3) in the loop region and T-FL-RTx2c did not. These were combined with PCR master mix and thermal cycled followed by a melt analysis.

ATG0015: /56-FAM//iMe-isodC/ATATCAGTCATTTGCCCAAAA
(SEQ ID NO: 24)/iSpC3/AAACCGCAAATGAC rCAT GAG ACA
GTA TAG TAG CGC TGA (SEQ ID NO: 25)/3SpC3/

T-FL-RTx2c: /56-FAM//iMe-
isodC/ATATCAGTCATTTGCCCAAAAAAAACCGCAAATGAC rCAT
GAG ACA GTA TAG TAG CGC TGA (SEQ ID NO: 15)/3SpC3/

Fwd Primer-
(SEQ ID NO: 22)
GAA GCA TTT GAA ATA GCA GAA GG

Rev Primer-
(SEQ ID NO: 23)
CAC AGA GCG TTC CTA GTT TTA CT

Reverse transcription PCR was performed without template to monitor for non-specific interactions that would cause a change in signal during a melt analysis. The below PCR master mix was created for a 25 µL reaction and run on an ABI Fast 7500 real-time thermal cycler. The thermal profile included 50° C. hold for 5 m., 95° C. hold for 2 m. 20 s., 44 cycles of 95° C. for 10 s. and 57° C. for 23 s. The melt analysis included ramping from 60 to 95° C. and reading at every 0.5° C.

TABLE 3

| PCR Master Mix | |
| --- | --- |
| Reagent | Working Concentration |
| Nuclease Free Water | |
| 10X ISOlution | 1x |
| 100 mM MgCl2 | 2.5 mM |
| 1M KCl | 0.05M |
| FluB Fwd primer | 0.12M |
| FluB Rev primer | 0.06M |
| Probe | 0.06M |
| RNase H2 HotStart | 1 mU |
| Glycerol Free Titanium Taq | 1x |
| MMLV Reverse Transcriptase | 0.75 |

Figure 13:
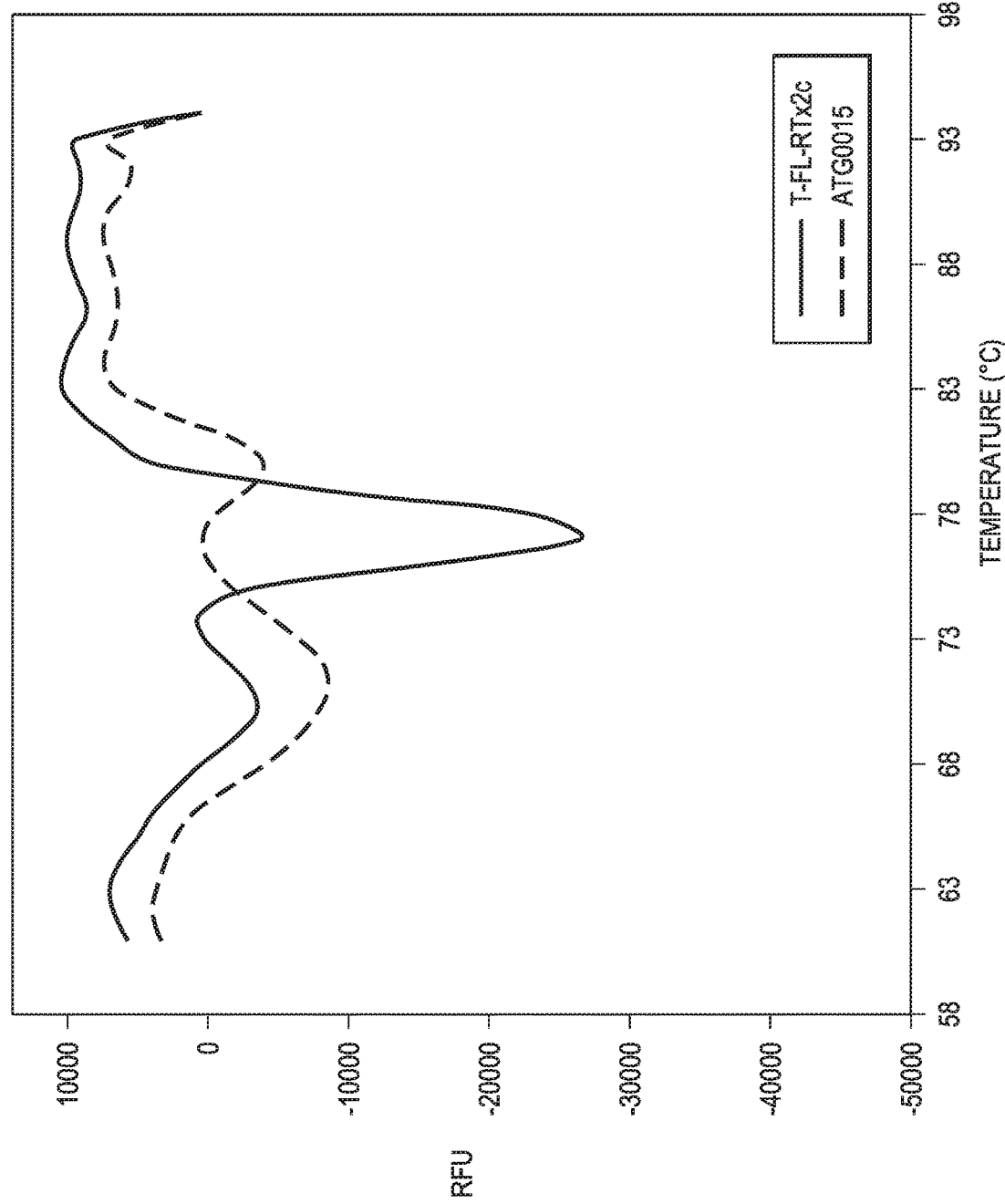
FIG. 13—A graph of the inverted derivative of data obtained during melt analysis.

FIG. 13 shows the inverted derivative of the data obtained during the melt analysis. A non-specific melt peak at 77° C. is present for the T-FL-RTx2c probe, which lacks the 3-carbon spacer in the loop region.

Without wishing to be bound by theory, it is thought that during the low temperature reverse transcriptase step at 50° C., the Rev primer in this case is hybridizing to the probe downstream of the loop region, which allows the primer to extend through the loop and incorporate a quencher across from the labeled isobase. This hybridization also causes the ribobase to be cleaved, allowing the probe to also extend along the primer. The double stranded product is amplified during the PCR reaction. The extension blocker prevents the non-specific extension of the primer across the loop region, which not only prevents the formation of a quencher/fluorophore pair, but also prevents a double stranded product with sufficient $T_m$ to be amplified during the 58° C. annealing steps in PCR.

Example 4—Multiplexing Using a Single Dye

This study demonstrated the ability to use multiple hairpin probes having the same fluorophore, but differing in the $T_m$ of the various extended hairpin probes. Three different probes specific for either Influenza A, Influenza B, or Adenovirus; having the same fluorophore (FAM), were tested together in the same PCR tube. Positive control samples containing extracted viral cultures of either Influenza A, Influenza B, or Adenovirus were placed in individual PCR tubes containing the multiplex PCR reaction components. These targets were tested at 1000 copies per reaction. The cleavable probe sequences are shown in Table 4.

TABLE 4

Probe Sequences

| Target Name | Cleavage Probe Sequence (5'- to 3') |
|---|---|
| FluB | /56-FAM//iMe-isodC/CAA AAA AAA GTCATGTTA CCAAAA(SEQ ID NO: 26)/iSpC3/AAACC TA ACATGAC rCATGAGACAGTATAGTAGCG (SEQ ID NO: 27)/3SpC3/ |
| FluA | /56-FAM//iMe-isodC/C ATA TCA TCA TCA TCT C ATTTTAGGC CCAAAA(SEQ ID NO: 28)/iSpC3/ AAACC GCCTAAAAT rCCCCTTAGTCAGAGGTGAC (SEQ ID NO: 29)/3SpC3/ |
| Adeno | /56-FAM//iMe-isodC/C TCC ATC CTC CTC CTC CTC TCT CTTCGAGA CCAAAA(SEQ ID NO: 30)/ iSpC3/AAACC TCT CGAAG rCGTCCTGTCCGGC (SEQ ID NO: 31)/3SpC3/ |

The below PCR master mix (Table 5) was created for a 25 µL reaction and run on an Life Technologies Quant Studio real-time PCR thermal cycler. The thermal profile included 50° C. hold for 5 m., 95° C. hold for 2 m. 20 s., 44 cycles of 95° C. for 10 s. and 57° C. for 23 s. The melt analysis included ramping from 60 to 95° C. and reading at every 0.5° C.

TABLE 5

PCR Master Mix

| Reagent | Final Concentration |
|---|---|
| Nuclease Free Water | |
| 10X ISOlution | 1x |
| 1M KCl | 0.05M |
| MgCl2 | 2.5 mM |
| Tris pH 8.0 | 10 mM |
| BisTrisPropane | 10 mM |
| Fwd primers | 0.48M |
| Rev primers | 0.12M |
| Probes | 0.02M |

TABLE 5-continued

PCR Master Mix

| Reagent | Final Concentration |
|---|---|
| RNase H2 HotStart (I.D.T) | 4 mU/µL |
| 50x Glycerol Free Titanium Taq (Clonetech) | 1x |
| MMLV Reverse Transcriptase (Promega) | 2 U/µl |

Figure 14:
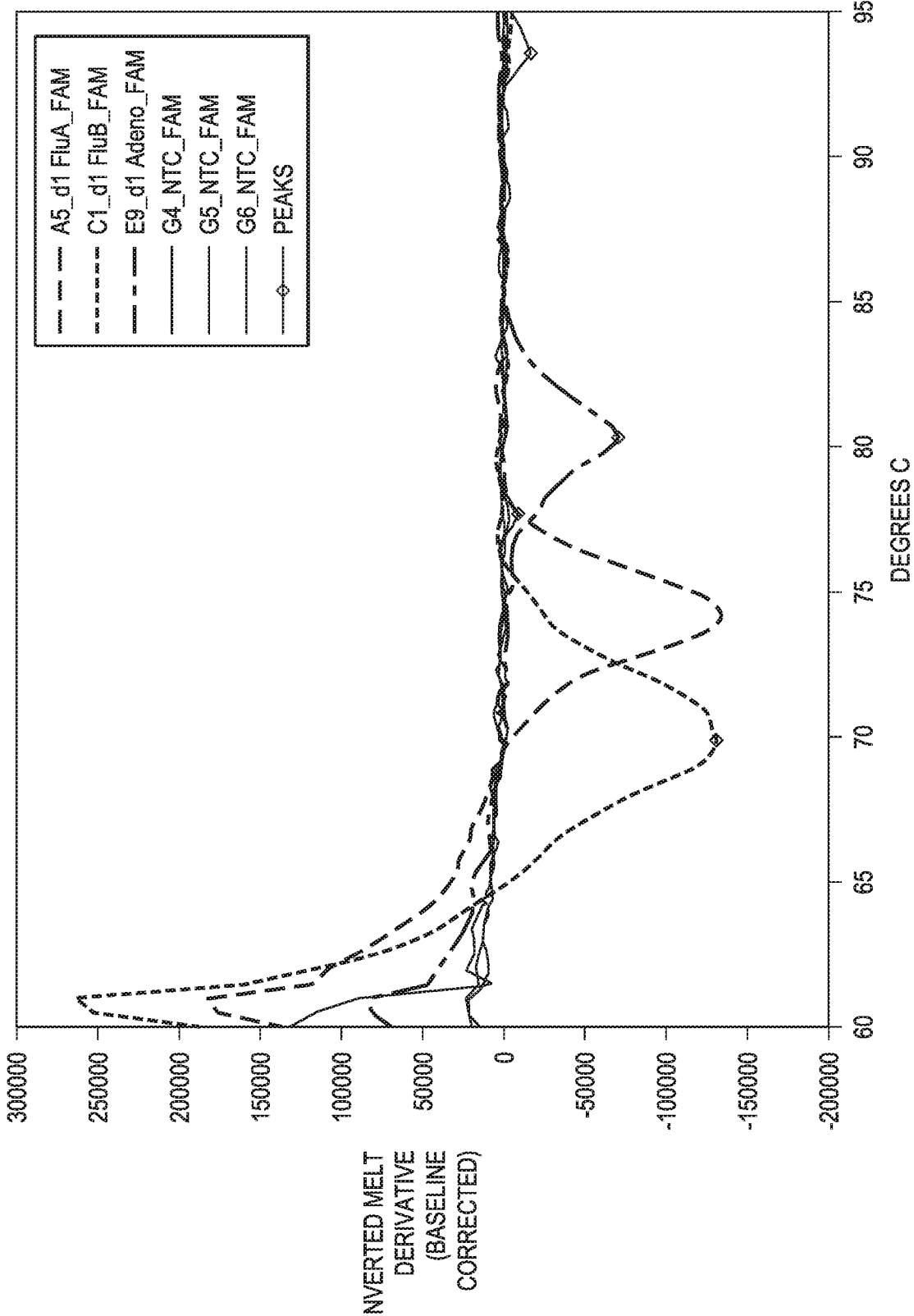
FIG. 14—Melt profile data for multiplex probes using the same fluorophore.

FIG. 14 shows melt profile data for 6 individual reactions (1 positive for each of the three targets at 1000 copies/reaction, and 3 No Template Control (NTC) samples) using the same multiplex PCR reaction mix. As can be seen in FIG. 14, each of the FluA, FluB, and Adeno-specific cleavable probes generated distinct melt profiles in the same fluorescence channel. Accordingly, in this example three different viruses were distinguished by melt profile when using the same fluorescent label.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. Nos. 4,942,124; 4,284,412; 4,989,977; 4,498,766; 5,478,722; 4,857,451; 4,774,189; 4,767,206; 4,714,682; 5,160,974; 4,661,913; 5,654,413; 5,656,493; 5,716,784; 5,736,330; 5,837,832; 5,837,860; 5,981,180; 5,994,056; 5,736,330; 5,981,180; 6,057,107; 6,030,787; 6,046,807; 6,057,107; 6,103,463; 6,139,800; 6,174,670; 6,268,222; 6,322,971; 6,366,354; 6,410,278; 6,411,904; 6,449,562; 6,514,295; 6,524,793; 6,528,165; 6,592,822; 6,939,720; 6,977,161; 7,226,737; 7,645,868; and 7,955,802

U.S. Published Publication Nos. 2005/0191625; 2008/0182312; and 2009/0148849

McMinn et al., *J. Am. Chem. Soc.*, 121:11585, 1999.

Ren et al., *J. Am. Chem. Soc.*, 118:1671, 1996.

Vogelstein et al., P.C.R. Digital, *Proc. Natl. Acad. Sci. USA*, 96:9236-9241, 1996.

Yan et al., "Isothermal Amplified Detection of DNA and RNA" *Mol. GioSyst.* 10:970-1003, 2014.

What is claimed is:

1. A method for detecting a target nucleic acid in a sample comprising:
   (a) partitioning the sample such that a majority of partitions will contain:
      (i) no more than one target nucleic acid molecule;
      (ii) reagents for amplifying the target nucleic acid molecule; and
      (iii) a cleavable probe, wherein the cleavable probe comprises a region that specifically hybridizes to the target nucleic acid molecule and hybridization of the cleavable probe to the target nucleic acid molecule or an amplicon thereof results in the cleavage of the cleavable probe;
   (b) amplifying the target nucleic acid molecule, if any, present in the partitions;
   (c) monitoring the partitions for a signal from a reporter associated with the cleavable probe while increasing or decreasing the temperature of the partitions to obtain a melt profile of the cleavable probe; and
   (d) detecting the presence of the target nucleic acid if the melt profile corresponds to that of the cleavable probe that has been cleaved, or detecting the absence of the target nucleic acid if the melt profile corresponds to that of the cleavable probe that is uncleaved.

2. The method of claim 1, wherein partitioning the sample comprises partitioning the sample into droplets in a non-aqueous continuous phase.

3. The method of claim 2, wherein the non-aqueous continuous phase comprises a fluorinated oil.

4. The method of claim 2, wherein the droplets are dispersed in a monolayer on a surface while monitoring the partitions for the signal from the reporter.

5. The method of claim 2, wherein amplifying the target nucleic acid comprises performing a polymerase chain reaction on the target nucleic acid in the droplet.

6. The method of claim 1, wherein partitioning the sample comprises partitioning the sample into wells in a microwell plate.

7. The method of claim 1, further comprising quantifying the target nucleic acid in the sample.

8. The method of claim 1, wherein the reagents for amplifying the target nucleic acid molecule comprise a polymerase with exonuclease activity.

9. The method of claim 1, wherein the signal from the reporter is a fluorescent signal.

10. The method of claim 1, wherein the cleavage of the cleavable probe is catalyzed by RNase H2.

11. The method of claim 1, wherein the cleavable probe is a hairpin probe.

12. The method of claim 1, wherein the cleavable probe comprises from 1 to 5 ribonucleotides.

13. The method of claim 1, wherein the reporter is a fluorophore.

14. The method of claim 1, wherein the reporter is a fluorophore and quencher pair.

15. A method for detecting a target nucleic acid in a sample comprising:
   (a) partitioning the sample into a plurality of partitions such that some of the partitions will contain zero target nucleic acid molecules and some of the partitions will contain one or more target nucleic acid molecules, wherein the plurality of partitions further comprise (i) reagents for amplifying the target nucleic acid molecule; and (ii) a cleavable probe, wherein the cleavable probe comprises a region that specifically hybridizes to the target nucleic acid molecule and hybridization of the cleavable probe to the target nucleic acid molecule or an amplicon thereof results in the cleavage of the cleavable probe;
   (b) amplifying the target nucleic acid molecule, if any, present in the partitions;

(c) monitoring the partitions for a signal from a reporter associated with the cleavable probe while increasing or decreasing the temperature of the partitions to obtain a melt profile of the cleavable probe; and (d) detecting the presence of the target nucleic acid if the melt profile corresponds to that of the cleavable probe that has been cleaved, or detecting the absence of the target nucleic acid if the melt profile corresponds to that of the cleavable probe that is uncleaved.

16. The method of claim 15, wherein partitioning the sample comprises partitioning the sample into droplets in a non-aqueous continuous phase.

17. The method of claim 16, wherein the non-aqueous continuous phase comprises a fluorinated oil.

18. The method of claim 16, wherein the droplets are dispersed in a monolayer on a surface while monitoring the partitions for the signal from the reporter.

19. The method of claim 16, wherein amplifying the target nucleic acid comprises performing a polymerase chain reaction on the target nucleic acid in the droplet.

20. The method of claim 15, wherein partitioning the sample comprises partitioning the sample into wells in a microwell plate.

21. The method of claim 15, further comprising quantifying the target nucleic acid in the sample.

22. The method of claim 15, wherein the reagents for amplifying the target nucleic acid molecule comprise a polymerase with exonuclease activity.

23. The method of claim 15, wherein the signal from the reporter is a fluorescent signal.

24. The method of claim 15, wherein the cleavage of the cleavable probe is catalyzed by RNase H2.

25. The method of claim 15, wherein the cleavable probe is a hairpin probe.

26. The method of claim 15, wherein the cleavable probe comprises from 1 to 5 ribonucleotides.

27. The method of claim 15, wherein the reporter is a fluorophore.

28. The method of claim 15, wherein the reporter is a fluorophore and quencher pair.

* * * * *

SEQUENCE LISTING

```
<160> NUMBER OF SEQ ID NOS: 31

<210> SEQ ID NO 1
<211> LENGTH: 29
<212> TYPE: DNA
<213> ORGANISM: Artificial Sequence
<220> FEATURE:
```

<223> OTHER INFORMATION: Synthetic probe

<400> SEQUENCE: 1
atatcagtca ttgcccaaac cgcaatgac                             29

<210> SEQ ID NO 2
<211> LENGTH: 34
<212> TYPE: DNA
<213> ORGANISM: Artificial Sequence
<220> FEATURE:
<223> OTHER INFORMATION: Synthetic probe

<400> SEQUENCE: 2
atatcagtca ttgcccaaaa aaaaccgcaa tgac                        34

<210> SEQ ID NO 3
<211> LENGTH: 27
<212> TYPE: DNA
<213> ORGANISM: Artificial Sequence
<220> FEATURE:
<223> OTHER INFORMATION: Synthetic probe

<400> SEQUENCE: 3
atatcagtct tgcccaaacc gcaagac                               27

<210> SEQ ID NO 4
<211> LENGTH: 32
<212> TYPE: DNA
<213> ORGANISM: Artificial Sequence
<220> FEATURE:
<223> OTHER INFORMATION: Synthetic probe

<400> SEQUENCE: 4
atatcagtct tgcccaaaaa aaaccgcaag ac                         32

<210> SEQ ID NO 5
<211> LENGTH: 31
<212> TYPE: DNA
<213> ORGANISM: Artificial Sequence
<220> FEATURE:
<223> OTHER INFORMATION: Synthetic probe

<400> SEQUENCE: 5
atatcagtca attgcccaaa ccgcaattga c                          31

<210> SEQ ID NO 6
<211> LENGTH: 36
<212> TYPE: DNA
<213> ORGANISM: Artificial Sequence
<220> FEATURE:
<223> OTHER INFORMATION: Synthetic probe

<400> SEQUENCE: 6
atatcagtca attgcccaaa aaaaaccgca attgac                     36

<210> SEQ ID NO 7
<211> LENGTH: 29
<212> TYPE: DNA
<213> ORGANISM: Artificial Sequence
<220> FEATURE:
<223> OTHER INFORMATION: Synthetic probe

<400> SEQUENCE: 7
atatcagtca agtgccaaac ccacttgac                             29

```
<210> SEQ ID NO 8
<211> LENGTH: 34
<212> TYPE: DNA
<213> ORGANISM: Artificial Sequence
<220> FEATURE:
<223> OTHER INFORMATION: Synthetic probe

<400> SEQUENCE: 8
atatcagtca agtgccaaaa aaaacccact tgac                                34

<210> SEQ ID NO 9
<211> LENGTH: 25
<212> TYPE: DNA
<213> ORGANISM: Artificial Sequence
<220> FEATURE:
<223> OTHER INFORMATION: Synthetic probe

<400> SEQUENCE: 9
atatcaggtc agccaaaccc tgacc                                          25

<210> SEQ ID NO 10
<211> LENGTH: 25
<212> TYPE: DNA
<213> ORGANISM: Artificial Sequence
<220> FEATURE:
<223> OTHER INFORMATION: Synthetic probe

<400> SEQUENCE: 10
atatcagtct gcccaaaccg cagac                                          25

<210> SEQ ID NO 11
<211> LENGTH: 23
<212> TYPE: DNA
<213> ORGANISM: Artificial Sequence
<220> FEATURE:
<223> OTHER INFORMATION: Synthetic probe

<400> SEQUENCE: 11
atatcagtcg cccaaaccgc gac                                            23

<210> SEQ ID NO 12
<211> LENGTH: 66
<212> TYPE: DNA
<213> ORGANISM: Artificial Sequence
<220> FEATURE:
<223> OTHER INFORMATION: Synthetic probe
<220> FEATURE:
<221> NAME/KEY: modified_base
<222> LOCATION: (42)..(42)
<223> OTHER INFORMATION: ribocytosine

<400> SEQUENCE: 12
atatcagtca ttgcccaaaa aaaaaaaaaa aaccgcaatg accatgagac agtatagtag   60
cgctga                                                               66

<210> SEQ ID NO 13
<211> LENGTH: 58
<212> TYPE: DNA
<213> ORGANISM: Artificial Sequence
<220> FEATURE:
<223> OTHER INFORMATION: Synthetic probe
<220> FEATURE:
<221> NAME/KEY: modified_base
<222> LOCATION: (35)..(35)
<223> OTHER INFORMATION: ribocytosine

<400> SEQUENCE: 13
```
atatcagtca ttgcccaaaa aaaaccgcaa tgaccatgag acagtatagt agcgctga      58

<210> SEQ ID NO 14
<211> LENGTH: 60
<212> TYPE: DNA
<213> ORGANISM: Artificial Sequence
<220> FEATURE:
<223> OTHER INFORMATION: Synthetic probe
<220> FEATURE:
<221> NAME/KEY: modified_base
<222> LOCATION: (37)..(37)
<223> OTHER INFORMATION: ribocytosine

<400> SEQUENCE: 14
atatcagtca tgtgcccaaa aaaaaccgca catgaccatg agacagtata gtagcgctga    60

<210> SEQ ID NO 15
<211> LENGTH: 60
<212> TYPE: DNA
<213> ORGANISM: Artificial Sequence
<220> FEATURE:
<223> OTHER INFORMATION: Synthetic probe
<220> FEATURE:
<221> NAME/KEY: modified_base
<222> LOCATION: (37)..(37)
<223> OTHER INFORMATION: ribocytosine

<400> SEQUENCE: 15
atatcagtca tttgcccaaa aaaaccgca aatgaccatg agacagtata gtagcgctga     60

<210> SEQ ID NO 16
<211> LENGTH: 60
<212> TYPE: DNA
<213> ORGANISM: Artificial Sequence
<220> FEATURE:
<223> OTHER INFORMATION: Synthetic probe
<220> FEATURE:
<221> NAME/KEY: modified_base
<222> LOCATION: (37)..(37)
<223> OTHER INFORMATION: ribocytosine

<400> SEQUENCE: 16
atatcagtca attgcccaaa aaaaccgca attgaccatg agacagtata gtagcgctga     60

<210> SEQ ID NO 17
<211> LENGTH: 58
<212> TYPE: DNA
<213> ORGANISM: Artificial Sequence
<220> FEATURE:
<223> OTHER INFORMATION: Synthetic probe
<220> FEATURE:
<221> NAME/KEY: modified_base
<222> LOCATION: (35)..(35)
<223> OTHER INFORMATION: ribocytosine

<400> SEQUENCE: 17
atatcagtca ttgaccaaaa aaaacctcaa tgaccatgag acagtatagt agcgctga      58

<210> SEQ ID NO 18
<211> LENGTH: 58
<212> TYPE: DNA
<213> ORGANISM: Artificial Sequence
<220> FEATURE:
<223> OTHER INFORMATION: Synthetic probe
<220> FEATURE:
<221> NAME/KEY: modified_base
<222> LOCATION: (35)..(35)
<223> OTHER INFORMATION: ribocytosine

<400> SEQUENCE: 18
atatcagtca ttacccaaaa aaaaccgtaa tgaccatgag acagtatagt agcgctga    58

<210> SEQ ID NO 19
<211> LENGTH: 60
<212> TYPE: DNA
<213> ORGANISM: Artificial Sequence
<220> FEATURE:
<223> OTHER INFORMATION: Synthetic probe
<220> FEATURE:
<221> NAME/KEY: modified_base
<222> LOCATION: (37)..(37)
<223> OTHER INFORMATION: ribocytosine

<400> SEQUENCE: 19
atatcagtca tgtacccaaa aaaaccgta catgaccatg agacagtata gtagcgctga    60

<210> SEQ ID NO 20
<211> LENGTH: 62
<212> TYPE: DNA
<213> ORGANISM: Artificial Sequence
<220> FEATURE:
<223> OTHER INFORMATION: Synthetic probe
<220> FEATURE:
<221> NAME/KEY: modified_base
<222> LOCATION: (39)..(39)
<223> OTHER INFORMATION: ribocytosine

<400> SEQUENCE: 20
atatcagtca ttgtacccaa aaaaaaccgt acaatgacca tgagacagta tagtagcgct    60
ga    62

<210> SEQ ID NO 21
<211> LENGTH: 70
<212> TYPE: DNA
<213> ORGANISM: Artificial Sequence
<220> FEATURE:
<223> OTHER INFORMATION: Synthetic probe
<220> FEATURE:
<221> NAME/KEY: modified_base
<222> LOCATION: (47)..(47)
<223> OTHER INFORMATION: ribocytosine

<400> SEQUENCE: 21
atatcagtca atgtgcccaa aaaaaaaaaa aaaaccgcac attgaccatg agacagtata    60
gtagcgctga    70

<210> SEQ ID NO 22
<211> LENGTH: 23
<212> TYPE: DNA
<213> ORGANISM: Artificial Sequence
<220> FEATURE:
<223> OTHER INFORMATION: Synthetic primer

<400> SEQUENCE: 22
gaagcatttg aaatagcaga agg    23

<210> SEQ ID NO 23
<211> LENGTH: 23
<212> TYPE: DNA
<213> ORGANISM: Artificial Sequence
<220> FEATURE:
<223> OTHER INFORMATION: Synthetic primer

<400> SEQUENCE: 23
cacagagcgt tcctagtttt act    23

<210> SEQ ID NO 24
<211> LENGTH: 21
<212> TYPE: DNA
<213> ORGANISM: Artificial Sequence
<220> FEATURE:
<223> OTHER INFORMATION: Synthetic probe

<400> SEQUENCE: 24
atatcagtca tttgcccaaa a                                              21

<210> SEQ ID NO 25
<211> LENGTH: 38
<212> TYPE: DNA
<213> ORGANISM: Artificial Sequence
<220> FEATURE:
<223> OTHER INFORMATION: Synthetic probe
<220> FEATURE:
<221> NAME/KEY: modified_base
<222> LOCATION: (15)..(15)
<223> OTHER INFORMATION: ribocytosine

<400> SEQUENCE: 25
aaaccgcaaa tgaccatgag acagtatagt agcgctga                            38

<210> SEQ ID NO 26
<211> LENGTH: 24
<212> TYPE: DNA
<213> ORGANISM: Artificial Sequence
<220> FEATURE:
<223> OTHER INFORMATION: Synthetic probe

<400> SEQUENCE: 26
caaaaaaaag tcatgttacc aaaa                                           24

<210> SEQ ID NO 27
<211> LENGTH: 34
<212> TYPE: DNA
<213> ORGANISM: Artificial Sequence
<220> FEATURE:
<223> OTHER INFORMATION: Synthetic probe
<220> FEATURE:
<221> NAME/KEY: modified_base
<222> LOCATION: (15)..(15)
<223> OTHER INFORMATION: ribocytosine

<400> SEQUENCE: 27
aaacctaaca tgaccatgag acagtatagt agcg                                34

<210> SEQ ID NO 28
<211> LENGTH: 32
<212> TYPE: DNA
<213> ORGANISM: Artificial Sequence
<220> FEATURE:
<223> OTHER INFORMATION: Synthetic probe

<400> SEQUENCE: 28
catatcatca tcatctcatt ttaggcccaa aa                                  32

<210> SEQ ID NO 29
<211> LENGTH: 33
<212> TYPE: DNA
<213> ORGANISM: Artificial Sequence
<220> FEATURE:
<223> OTHER INFORMATION: Synthetic probe
<220> FEATURE:
<221> NAME/KEY: modified_base
<222> LOCATION: (15)..(15)
<223> OTHER INFORMATION: ribocytosine

```
<400> SEQUENCE: 29
aaaccgccta aaatcccctt agtcagaggt gac                          33

<210> SEQ ID NO 30
<211> LENGTH: 36
<212> TYPE: DNA
<213> ORGANISM: Artificial Sequence
<220> FEATURE:
<223> OTHER INFORMATION: Synthetic probe

<400> SEQUENCE: 30
ctccatcctc ctcctcctct ctcttcgaga ccaaaa                       36

<210> SEQ ID NO 31
<211> LENGTH: 26
<212> TYPE: DNA
<213> ORGANISM: Artificial Sequence
<220> FEATURE:
<223> OTHER INFORMATION: Synthetic probe
<220> FEATURE:
<221> NAME/KEY: modified_base
<222> LOCATION: (14)..(14)
<223> OTHER INFORMATION: ribocytosine

<400> SEQUENCE: 31
aaacctctcg aagcgtcctg tccggc                                  26
```